US012577572B2

(12) United States Patent
Lynch et al.

(10) Patent No.: US 12,577,572 B2
(45) Date of Patent: Mar. 17, 2026

(54) COMPOSITIONS, SYSTEMS, AND METHODS FOR HIGH LEVEL EXPRESSION OF RECOMBINANT PROTEIN

(71) Applicant: Duke University, Durham, NC (US)

(72) Inventors: Michael Lynch, Durham, NC (US); Romel Menacho Melgar, Durham, NC (US); Zhixia Ye, Raleigh, NC (US); Eirik A. Moreb, Durham, NC (US)

(73) Assignee: Duke University, Durham, NC (US)

( * ) Notice: Subject to any disclaimer, the term of this patent is extended or adjusted under 35 U.S.C. 154(b) by 902 days.

(21) Appl. No.: 17/755,158

(22) PCT Filed: Oct. 23, 2020

(86) PCT No.: PCT/US2020/057062
§ 371 (c)(1),
(2) Date: Apr. 22, 2022

(87) PCT Pub. No.: WO2021/081325
PCT Pub. Date: Apr. 29, 2021

(65) Prior Publication Data
US 2022/0411806 A1     Dec. 29, 2022

Related U.S. Application Data

(60) Provisional application No. 62/924,898, filed on Oct. 23, 2019.

(51) Int. Cl.
| | |
|---|---|
| *C12N 15/70* | (2006.01) |
| *C12N 1/20* | (2006.01) |
| *C12N 15/63* | (2006.01) |
| *C12P 1/04* | (2006.01) |
| *C12P 21/00* | (2006.01) |

(52) U.S. Cl.
CPC ............ *C12N 15/635* (2013.01); *C12N 1/20* (2013.01); *C12N 15/70* (2013.01); *C12N 2500/14* (2013.01); *C12N 2500/16* (2013.01); *C12N 2500/24* (2013.01); *C12N 2500/42* (2013.01)

(58) Field of Classification Search
CPC .. C12P 7/42; C12P 13/06; C12P 21/00; C12P 1/02; C12P 1/04; C12N 2500/00; C12N 15/70
See application file for complete search history.

(56) References Cited

U.S. PATENT DOCUMENTS

| | | |
|---|---|---|
| 2010/0184162 A1 | 7/2010 | Imaizumi et al. |
| 2012/0129220 A1 | 5/2012 | Yanagihara et al. |
| 2017/0121707 A1 | 5/2017 | Lynch et al. |

FOREIGN PATENT DOCUMENTS

| | | |
|---|---|---|
| WO | 2018/156646 A1 | 8/2018 |
| WO | 2018/157150 A1 | 8/2018 |

OTHER PUBLICATIONS

International Search Report and Written Opinion issued by USPTO in PCT application No. PCT/US20/57062, mailing date Mar. 18, 2021.
Tao, Z., et al., "Yeast Extract: Characteristics, Production, Applications and Future Perspectives", J. Microbiol. Biotechnol. 2023. 33(2): 151-166.

*Primary Examiner* — Maryam Monshipouri
(74) *Attorney, Agent, or Firm* — Benesch Friedlander Coplan & Aronoff LLP

(57) ABSTRACT

Improved production of recombinant proteins in *E. coli*, reliant on tightly controlled autoinduction, triggered by phosphate depletion in stationary phase. The process also provides an optimized autoinduction media, enabling routine batch production at various culture volumes where cells densities routinely reach ~5-7 g cell dry weight per liter and offer protein titers above 2 g/L. The methodology has been validated with a set of diverse heterologous proteins and is of general use for the facile optimization of routine protein expression from high throughput screens to fed-batch fermentation.

15 Claims, 8 Drawing Sheets
Specification includes a Sequence Listing.

COMPOSITIONS, SYSTEMS, AND METHODS FOR HIGH LEVEL EXPRESSION OF RECOMBINANT PROTEIN

CROSS-REFERENCE TO RELATED APPLICATIONS

This application claims is a National Stage Entry of PCT/US20/57062 filed Oct. 23, 2020 which claim priority to U.S. Provisional Patent Application No. 62/924,898, filed Oct. 23, 2019, which is incorporated by reference herein in its entirety.

STATEMENT AS TO FEDERALLY SPONSORED RESEARCH

This invention was made with Government support under Federal Grant nos.: EAGER: #1445726 awarded by the National Science Foundation (NSF); HR0011-14-C-0075 awarded by the Defense Advanced Research Projects Agency (DARPA); YIP #12043956 awarded by the Office of Naval Research; EE0007563 awarded by the Department of Energy (DOE); and T32GM008555 awarded by the National Institutes of Health (NIH). The Federal Government has certain rights to this invention.

REFERENCE TO A SEQUENCE LISTING

The instant application contains a Sequence Listing which has been filed electronically in ASCII format as 47381-42_ST25.txt created on Oct. 22, 2020 and is 24,956 bytes in size and is hereby incorporated by reference in its entirety.

BACKGROUND

Heterologous protein expression is a standard workflow common in numerous fields of biology and *E. coli* is the workhorse microbe for routine protein production in academia and industry. *E. coli* based processes are used for the production of over 30% of protein based drugs that are on the market today, and pET based expression in *E. coli* strain BL21(DE3) and its derivatives is a mainstay of heterologous expression in many labs.

Standard protocols rely on easily prepared media (LB and or TB) but require culture monitoring to optimize induction in exponential phase. Auto-induction protocols removing the need for manual additions have been developed, most notably by Studier, and require the use of multiple carbon substrates, such as glucose and lactose. After glucose depletion the consumption of lactose induces heterologous expression. Significant recent work has been done in developing new protocols enabling auto-induction systems focused on using novel auto inducing promoters that respond to a variety of signals from cell density to oxygen limitation. Despite simplifying expression protocols, many of these approaches still result in relatively low biomass and protein levels and have not been validated in multiple culture systems including instrumented bioreactors. The use of BL21 and its derivatives can be further complicated by heterogeneous induction, resulting from lactose-based inducers, as well as the accumulation of acetic acid in fermentations with excess carbon source, which can have toxic effects on both cell growth and protein expression.

There remains a need for auto-inducible protein expression methods with tightly controlled expression, minimal overflow metabolism, and a high level of protein expression. Ideally new methods will be adaptable to numerous workflows and culture volumes, from high throughput screening approaches in microtiter plates to larger scale production in instrumented bioreactors, in commercially relevant media.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the development of a facile protocol for the routine high-level expression of proteins made by the inventors. In some aspects, the method relies on a promoter that is induced by phosphate depletion, where protein expression is induced at the entry into stationary phase. While the expression of heterologous proteins during stationary phase may seem counterintuitive and at odds with maximal production, stationary phase cells can maintain significant metabolic activity and produce high levels of protein. Specifically, phosphate depletion has been used routinely for heterologous protein expression. In addition, it has been shown that phosphate depletion can be used to amplify the expression of heterologous proteins using the pET based T7 promoters in *E. coli*. Phosphate dependent promoters are used in an engineered strain of *E. coli* with minimal acetate production, and near optimal growth rates and yields, offering tightly controlled expression. In some aspects, these strains and plasmids can be used in minimal media in instrumented bioreactors as well as with an optimized autoinduction broth enabling high level batch expression, in cultures as small as 20 µL in 384 well plates, to 100 mL in larger shake flasks. Hence, the present disclosure provides, in part, compositions, systems, and methods for high level expression of recombinant protein.

One aspect of the present disclosure provides a method of recombinant protein expression comprising, consisting of, or consisting essentially of: (i) Transforming a strain of *E. coli* with a plasmid containing a phoB regulated promoter which is induced upon phosphate depletion, wherein the promoter drives expression of at least one protein; (ii) Growing the strain from (i) in a batch media capable of enabling growth of the strain as well as autoinduction of protein expression upon phosphate depletion, in which the media of (ii) contains greater than 5.0 g/L and less than 15.0 g/L of any combination of Yeast extract and Casamino acids and less than 400 mM ammonium.

In one aspect, the media also contains yeast extract, casamino acids, iron, calcium, magnesium, ammonium, sulfate and phosphate and trace elements. In another aspect, the media also contains thiamine and citric acid. In another aspect, the recombinant expression is accomplished in a volume of 20 microliters to Liters.

Another aspect of the present disclosure provides compositions comprising, consisting of, or consisting essentially of transformed *E. coli* strain comprising a plasmid containing a phoB regulated promoter which is induced upon phosphate depletion as provided herein.

Another aspect of the present disclosure provides systems incorporating the compositions and methods provided herein for the high level of expression of recombinant proteins.

Yet another aspect of the present disclosure provides all that is described and illustrated herein.

Other methods, features and/or advantages is, or will become, apparent upon examination of the following figures and detailed description. It is intended that all such additional methods, features, and advantages be included within this description and are protected by the accompanying claims.

BRIEF DESCRIPTION OF DRAWINGS

The novel features of the invention are set forth with particularity in the claims. A better understanding of the features and advantages of the present invention will be obtained by reference to the following detailed description that sets forth illustrative aspects, in which the principles of the invention are used, and the accompanying drawings of which:

FIG. 5A-B are graphs showing the media development using Design of Experiment (DoE) methodology in accordance with one aspect of the present disclosure.

DETAILED DESCRIPTION

Figure 1:
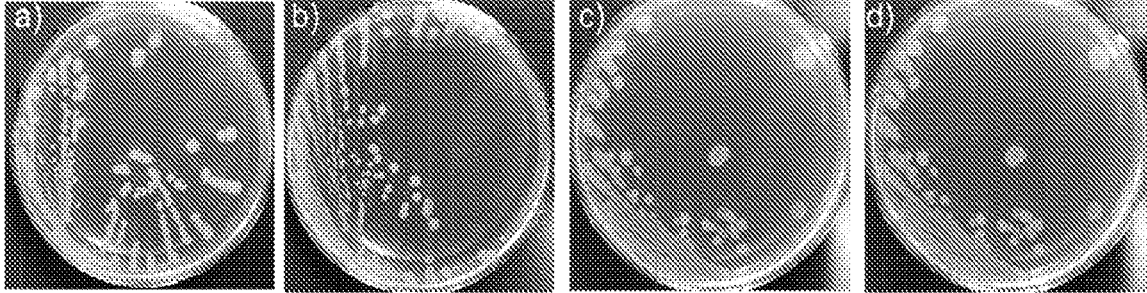
FIG. 1A-D are images showing the leaky expression of yibDp-GFPuv in BL21(DE3) in accordance with one aspect of the present disclosure
Figure 2:
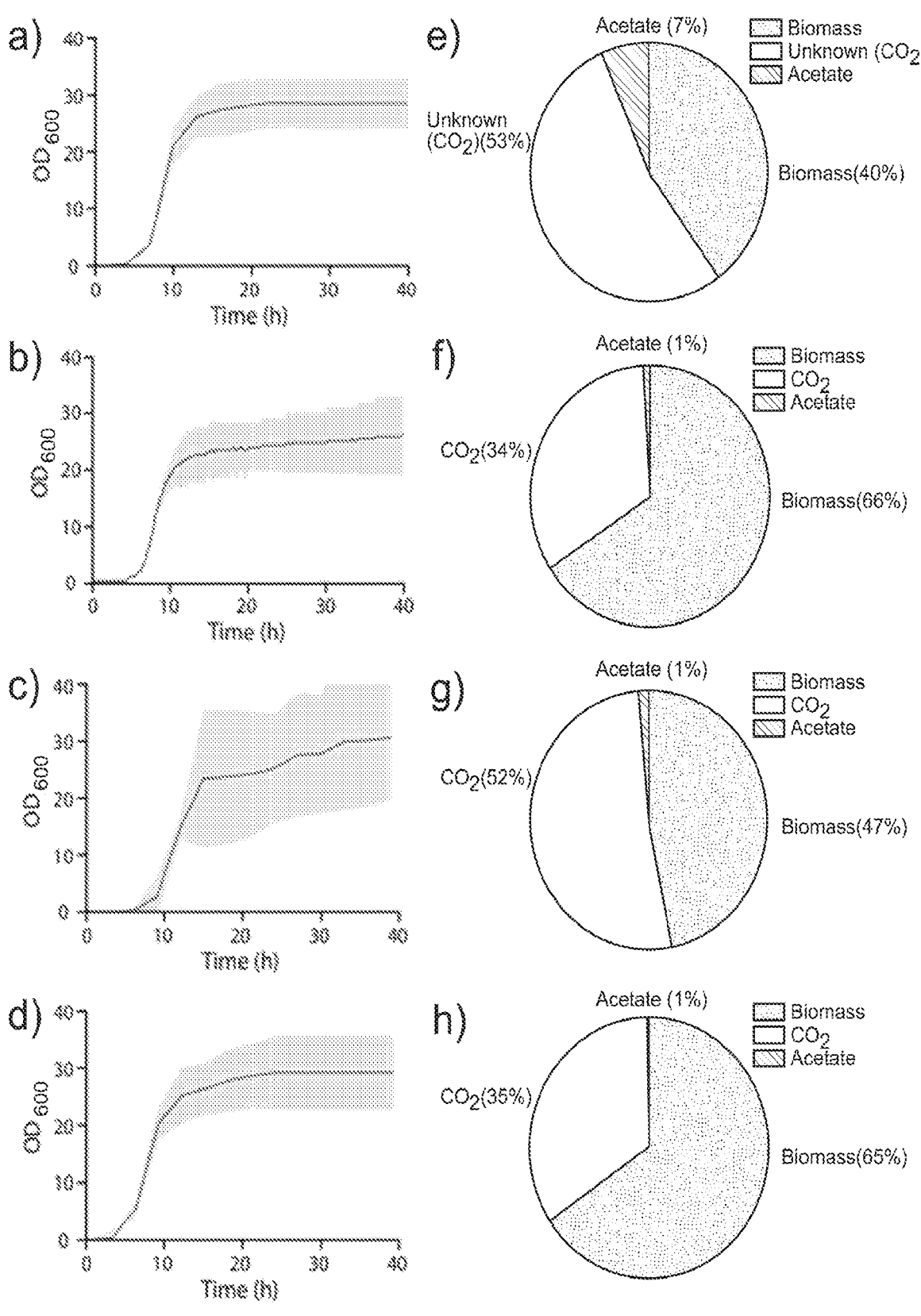
FIG. 2A-H are graphs showing the growth and byproduct formation of E. coli strains in minimal media fermentations in accordance with one aspect of the present disclosure.

We now describe the improved production of recombinant proteins in E. coli, reliant on tightly controlled autoinduction, triggered by phosphate depletion in stationary phase. The method, reliant on engineered strains and plasmids, enables improved protein expression across scales. Expression levels using this approach have reached as high as 55% of total cellular protein. Initial use of the method in instrumented fed batch fermentations enables cell densities of 10 grams dry cell weight (gCDW) per liter and protein titers up to $2.7+/-0.2$ g/L (270 mg/gCDW). The process has also been adapted to an optimized autoinduction media, enabling routine batch production at culture volumes of 20 μL (384 well plates), 100 μL (96 well plates), 20 mL and 100 mL. In batch cultures, cells densities routinely reach ~5-7 gCDW per liter, offering protein titers above 2 g/L. The methodology has been validated with a set of diverse heterologous proteins and is of general use for the facile optimization of routine protein expression from high throughput screens to fed-batch fermentation.

I. Definitions

Unless otherwise defined, all technical and scientific terms used herein have the same meaning as commonly understood by one of ordinary skill in the art to which this invention pertains. In case of conflict, the present specification, including definitions, will control.

Unless otherwise specified, "a," "an," "the," "one or more of," and "at least one" are used interchangeably. The singular forms "a", "an," and "the" are inclusive of their plural forms.

The recitations of numerical ranges by endpoints include all numbers subsumed within that range (e.g., 0.5 to 5 includes 1, 1.5, 2, 2.75, 3, 3.80, 4, 5, etc.).

The term "about," when referring to a value or to an amount of mass, weight, time, volume, concentration, or percentage is meant to encompass variations of ±10% from the specified amount. The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

Moreover, the present disclosure also contemplates that in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression. The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome). As used herein, chromosomal and native and endogenous refer to genetic material of the host microorganism.

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production, Micro-fermentation (microfermentation) or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a UniProt identification number, which would be well known to one skilled in the art. The UniProt database can be accessed at www.UniProt.org. When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "μL" or "uL" or "ul" means microliter(s), "mL" means milliliter(s), "L" means liter(s), "mm" means millimeter(s), "nm" means nanometers, "mM" means millimolar, "μM" or "uM" means micromolar, "M" means molar, "mmol" means millimole(s), "μmol" or "uMol" means micromole(s)", "g" means gram(s), "μg" or "ug" means microgram(s) and "ng" means nanogram(s), "PCR" means polymerase chain reaction, "OD" means optical density, "OD600" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-μ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

Overview of Invention Aspects

One aspect of the present disclosure provides a method of recombinant protein expression comprising, consisting of, or consisting essentially of: (i) Transforming a strain of E. coli with a plasmid containing a phoB regulated promoter which is induced upon phosphate depletion, wherein the promoter drives expression of at least one protein; (ii) Growing the strain from (i) in a batch media capable of enabling growth of the strain as well as autoinduction of protein expression upon phosphate depletion, in which the media of (ii) contains greater than 5.0 g/L and less than 15.0 g/L of any combination of Yeast extract and Casamino acids and less than 400 mM ammonium.

In one aspect, the media also contains yeast extract, casamino acids, iron, calcium, magnesium, ammonium, sulfate and phosphate and trace elements.

In another aspect, the media also contains thiamine and citric acid.

In another aspect, the recombinant expression is accomplished in a volume of 20 microliters to Liters.

Another of the present disclosure provides compositions comprising, consisting of, or consisting essentially of transformed E. coli strain comprising a plasmid containing a phoB regulated promoter which is induced upon phosphate depletion as provided herein.

Another aspect of the present disclosure provides systems incorporating the compositions and methods provided herein for the high level of expression of recombinant proteins.

In one aspect, a method of expression of a protein is provided. The method include a step of providing a genetically modified microorganism that is obtained by transforming a microorganism strain with a plasmid, the plasmid comprising a phoB regulated promoter operatively linked to a nucleic acid encoding the expressed protein; and subsequently growing the genetically modified microorganism in a batch media to obtain a biomass and express the protein. Of importance, the batch media enables growth of the genetically modified microorganism in the presence of phosphate in the batch media and autoinduction of protein expression upon depletion of phosphate from the batch media. The batch media may be characterized by greater than 5.0 g/L and less than 15.0 g/L of a combination of yeast extract and casamino acids, and the batch media contains from about 15 mM to about 400 mM ammonium ion. The methods are useful for expressing any protein from any species provide the nucleic acid for the protein has been identified and characterized so that it may be combined with the regulated promotor as described. Preferably the microorganism source for generation of a genetically modified microorganism is an *E. coli* microorganism, though the methods described herein are applicable to a wide variety of microorganism species.

In some aspects, the batch media may further be characterized by the presence of iron, calcium, magnesium, ammonium, sulfate and phosphate, trace elements, thiamine, citric acid, or surfactant. These components may be provided in any form (e.g. various salt, emulsions, dissociated ions, or the like) or concentration. As the phosphate source is significant to biomass growth and protein expression, the yeast extract and casamino acids may be the batch media phosphate source. Alternatively, inorganic phosphate may be added to the batch media.

In other aspects, the methods described are scalable to any amount between 20 microliters and many Liters and may reach a biomass level of about 10 gCDW/L. In another aspect, phosphate depletion from the batch media induces a stationary phase in genetically modified microorganism. In another aspect, the methods described are capable of producing expressed protein in an amount that is between about 10 and about 55% of the total cellular protein content of the genetically modified microorganism, or greater than 2 g/L.

In some aspects, the phoB regulated promoter or the plasmid that transforms a microorganism may be the yibDp promoter of the *E. coli* yibD (waaH) gene, or may comprise in whole or part the sequence of SEQ ID NO: 1.

In some aspects, the strain of *E. coli* that is transformed with a plasmid further comprises chromosomal deletion of genes selected from the group consisting of: ackA-pta, pflB, adhE, ldhA, poxB, iclR or arcA.

In some aspects the batch media may include yeast extract in an amount between 0625 g/L and 10 g/L; casamino acids in an amountbetween 0625 g/L and 11.5 g/L; or ammonium ion is present in an amount from 17 mM to 204 mM. In some aspects, the batch media comprises ammonium sulfate or an ammonium salt. In some aspects, the ammonium ion is present in the batch media in an amount from 17 mM to 204 mM. In some aspects, the batch media comprises 40.8 mM ammonium sulfate; 6.2 g/L yeast extract, and 3.5 g/L casamino acid. In some aspects, the batch media comprises 68 mM ammonium sulfate; 2.5 g/L yeast extract, and 2.5 g/L casamino acid.

Disclosed Aspects Are Non-Limiting

While various aspects of the present invention have been shown and described herein, it is emphasized that such aspects are provided by way of example only. Numerous variations, changes and substitutions may be made without departing from the invention herein in its various aspects. Specifically, and for whatever reason, for any grouping of compounds, nucleic acid sequences, polypeptides including specific proteins including functional enzymes, metabolic pathway enzymes or intemediates, elements, or other compositions, or concentrations stated or otherwise presented herein in a list, table, or other grouping unless clearly stated otherwise, it is intended that each such grouping provides the basis for and serves to identify various subset aspects, the subset aspects in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and aspects herein, there may be employed conventional molecular biology, cellular biology, microbiology, and recombinant DNA techniques within the skill of the art. Such techniques are explained fully in the literature. See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986. These published resources are incorporated by reference herein.

The following published resources are incorporated by reference herein for description useful in conjunction with the invention described herein, for example, methods of industrial bio-production of chemical product(s) from sugar sources, and also industrial systems that may be used to achieve such conversion (Biochemical Engineering Fundamentals, $2^{nd}$ Ed. J. E. Bailey and D. F. Ollis, McGraw Hill, New York, 1986, e.g. Chapter 9, pages 533-657 for biological reactor design; Unit Operations of Chemical Engineering, $5^{th}$ Ed., W. L. McCabe et al., McGraw Hill, New York 1993, e.g., for process and separation technologies analyses; Equilibrium Staged Separations, P. C. Wankat, Prentice Hall, Englewood Cliffs, NJ USA, 1988, e.g., for separation technologies teachings).

All publications, patents, and patent applications mentioned in this specification are entirely incorporated by reference.

Examples

For the purposes of promoting an understanding of the principles of the present disclosure, reference will now be made to preferred aspects and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

We described the development of a facile protocol for the routine high level expression of proteins. The method relies on a promoter that is induced by phosphate depletion, where protein expression is induced at the entry into stationary phase. While the expression of heterologous proteins during stationary phase may seem counterintuitive and at odds with maximal production, stationary phase cells can maintain significant metabolic activity and produce high levels of protein. Specifically, phosphate depletion has been used routinely for heterologous protein expression. In addition, it has been shown that phosphate depletion can be used to amplify the expression of heterologous proteins using the pET based T7 promoters in *E. coli*. Phosphate dependent promoters are used in an engineered strain of *E. coli* with minimal acetate production, and near optimal growth rates and yields, offering tightly controlled expression. These strains and plasmids can be used in minimal media in instrumented bioreactors as well as with an optimized auto-induction broth enabling high level batch expression, in cultures as small as 20 μL in 384 well plates, to 100 mL in larger shake flasks.

Initial Characterization of Phosphate Induction with the yibDp Gene Promoter.

To move from IPTG based induction to autoinduction via phosphate depletion, we leveraged a previously reported phoB regulated promoter, specifically the promoter of the *E. coli* yibD (waaH) gene, referred to herein as yibDp, and constructed a plasmid enabling the induction of mCherry upon phosphate depletion (pHCKan-yibDp-mCherry, Table 1 (below), Table 2 describes the promoter sequence.

TABLE 1

Plasmids and strain used in this study

| Plasmid | Insert | promoter | ori | Res | Addgene | Source |
|---|---|---|---|---|---|---|
| pSMART-HC-Kan | None | None | colE1 | Kan | NA | Lucigen |
| pLysS | T7 lysozyme | NA | p15a | Cm | NA | NEB |
| pHCKan-yibDp-GFPuv | GFPuv | yibDp | colE1 | Kan | 127078 | This study |
| pHCKan-yibDp-mCherry | 6xhis-mCherry | yibDp | colE1 | Kan | 127058 | This study |
| pETM6 | none | T7 (pET) | colE1 | Amp | 49795 | Jones et al. |
| pETM6-mCherry | mCherry | T7 (pET) | colE1 | Amp | 66534 | Jones et al. |
| pCDF | None | None | cloDF13 | Sm | 89596 | This study |
| pTCmc-yibDp-SBS-mCherry | SBS-mCherry | yibDp | p15a | Cm | 134598 | This study |
| pTKhc-yibDp-GFP-β20cp6 | GFP-β20-cp6 | yibD | colE1 | Kan | 127060 | This study |
| pTKhc-yibDp-GFP-cp6 | GFP-cp6 | yibD | colE1 | Kan | 134938 | This study |
| pCDF-yibDp-matB | matB | yibDp | cloDF13 | Sm | 134597 | This study |
| pSMART-Ala1 | AlaDh(D196A/L197R) | yibDp | colE1 | Kan | 65814 | This study |
| pCDF-yibDp-mdlC-his | mdlC-6xhis | yibDp | cloDF13 | Sm | 134590 | This study |
| pHCKan-yibDp-GST | GST-6xHis | yibD | colE1 | Kan | 134592 | This study |
| pHCKan-yibDp-Nef | Nef | yibD | colE1 | Kan | 134593 | This study |
| pTKhc-yibDp-cimA3.7 | cimA3.7 | yibDp | colE1 | Kan | 134595 | This study |
| pHCKan-yibDp-CBD-hGLY | hGLYAT2 | yibD | colE1 | Kan | 134596 | This study |

Strains used in this study

| Strain | Genotype | Source |
|---|---|---|
| BL21(DE3) | F– ompT gal dcm Lon hsdS$_B$(r$_B$-m$_B$-) λ(DE3 [lacI lacUV5-T7p07 ind1 sam7 nin5]) [malB$^+$]$_{k-12}$ (λ$^s$) | NEB |
| BWapldf | F–, λ–, Δ(araD-araB)567, lacZ4787(del)(::rrnB-3), rph-1, Δ(rhaD-rhaB)568, hsdR51, ΔackA-pta, ΔpoxB, ΔpflB, ΔldhA, ΔadhE | Jian, J et al. |
| DLF_R002 | BWapldf, ΔiclR, ΔarcA | This study |
| DLF_R003 | DLF_R002, ΔompT::apmR | This study |

NEB-New England BioLabs,

Res-resistance marker,

Sm-spectinomycin,

Cm-chloramphenicol,

Kan-kanamycin,

Amp-ampicillin

TABLE 2

| | yibDp Sequence | |
|---|---|---|
| Promoter Name | Sequence of promoter underlined, including example ribosomal binding site and start codon (bo[ld]]) | |
| yibDp | GTGCGTAATTGTGCTGATCTCTTATATAGCTGCTCT CATTATCTCTCTACCCTGAAGTGACTCTCTCACCTG TAAAAATAATATCTCACAGGCTTAATAGTTTCTTAA TACAAAGCCTGTAAAACGTCAGGATAACTTCTGTGT AGGAGGATAATCTATG (SEQ ID NO: 1]) | |

We initially evaluated the expression of this construct in BL21(DE3), BL21(DE3) with pLysS and a well character-ized *E. coli* K12 derivative: BW25113. The accessory plas-mid (pLysS) expressing T7 lysozyme, is routinely used to reduce leaky induction in pET based systems. Referring now to FIG. 1A-D: Leaky Expression of yibDp-GFPuv in BL21 (DE3). Agar plates with growth of plasmid pHCKan-yibDp-mcherry in a) BW25113, b) DLF_R002, c) BL21(DE3) and d) BL21(DE3) pLys. Unexpectedly, significant basal expres-sion was observed in BL21(DE3) (FIG. 1D). In contrast, no significant basal expression was observed in BW25113 (FIG. 1A). These results indicate the potential ability of T7 RNA polymerase to recognize this promoter, differential phoB regulation between these strains, or yet additional unknown regulatory differences.

Host Strain Engineering

With BL21(DE3) demonstrating baseline heterogeneous leaky expression with the yibDp promoter, and in light of other routine issues encountered in using BL21 and its derivatives, such as accumulation of acetic acid, we turned to engineering a BW25113 derivative for optimal growth and minimal byproduct formation. We began with a previ-ously reported derivative, strain BWapldf, with deletions in genes leading to common mixed acid fermentation products, such as lactic and acetic acid. BWapldf has deletions in the following genes: ackA-pta, pflB, adhE, ldhA, and poxB reducing the rates of production of acetate, formate, lactate and ethanol from overflow metabolites. Deletions of the two global regulators iclR and arcA were next incorporated into this strain. These mutations have been shown to improve biomass yield and reduce overflow metabolism in K12 derivatives. Together these mutations increase flux through the citric acid cycle and glyoxylate bypass and reduce overflow metabolism by increasing the rate of oxidation of excess carbon to carbon dioxide and increasing ATP supply.

These strains, as well as a BL21(DE3) pLysS control were initially evaluated in controlled fed batch fermentations, using a defined minimal media (FGM10 media, refer to Materials and Methods) wherein phosphate concentrations limit biomass levels. Growth rates, biomass and byproducts, including acetic acid, were measured. Results are given in FIG. 2A-H: Growth and byproduct formation of *E. coli* strains in minimal media fermentations. Biomass levels as a function of time for (a) BL21(DE3)pLys (b) BW25113, (c) BWapldf and (d) DLF_R002 respectively. (FIG. 2E-H) Distribution of glucose utilized during growth in minimal medium fermentations: (2E) BL21(DE3)pLys, (2F) BW25113, (2G) BWapldf and (2H) DLF_R002 respectively. Results are averages of duplicate fermentations. $CO_2$ was explicitly measured via off-gas analysis for strain BW25113, BWapldf and DLF_R002. In the case of BL21(DE3) pLys, $CO_2$ is included in unknown products required to account for glucose consumption.

Figure 3:
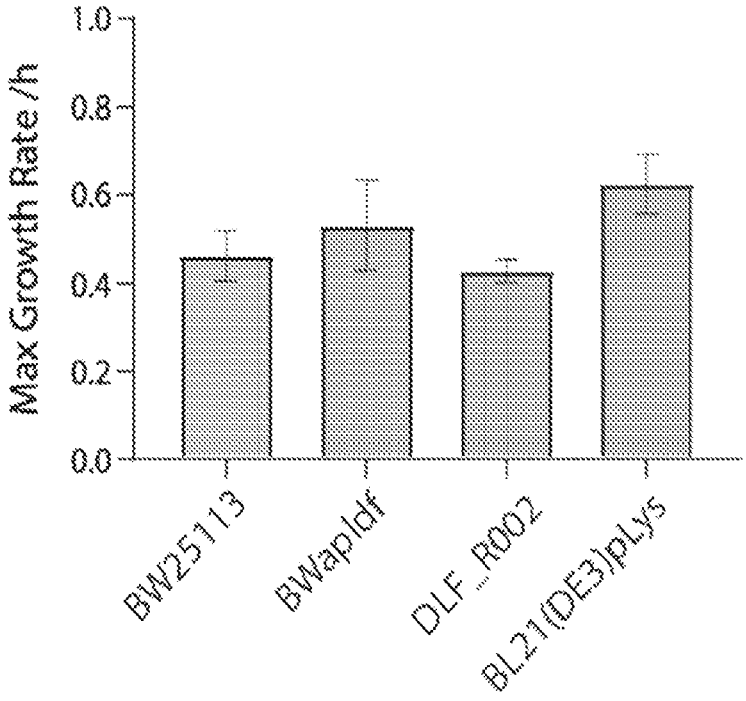
FIG. 3 is a graph showing maximal growth rates of E. coli strains in minimal media fermentations. Results are averages of duplicate fermentations in accordance with one aspect of the present disclosure.

In these studies organic acid byproducts, other than acetic acid were not observed. As expected, BL21(DE3) produced acetic acid during growth (FIG. 2E). Interestingly, strain BWapldf, despite having numerous deletions had a signifi-cantly decreased biomass yield and increased acetic acid production compared to BW25113 (FIGS. 2F-G). The dele-tion of the two global regulators, arcA and iclR, (strain DLF_R002) recovered biomass yield and virtually elimi-nated acetic acid production in this host (FIG. 2H). Refer to FIG. 3 for maximal growth rates of *E. coli* strains in minimal media fermentations. Results are averages of duplicate fer-mentations.

Figure 4:
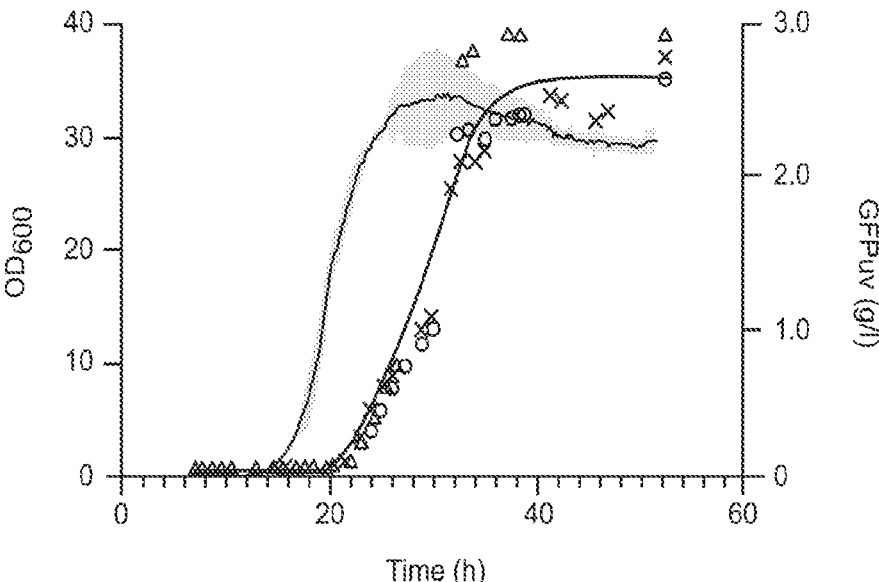
FIG. 4 is a graph showing the autoinduction of GPFuv expression in bioreactors in accordance with one aspect of the present disclosure.

Using strain DLF_R002 we next turned to evaluate pro-tein expression in bioreactors using FGM10 media. As mentioned biomass levels supported by FGM10 media are limited by phosphate, and phosphate depletion occurs when biomass levels reach an optical density of ~30-35 or ~10 gCDW/L. In this case we constructed an additional plasmid with GFPuv driven by the yibDp promoter (pHCKan-yibDp-GFPuv, Table 1. Results are given in FIG. 4: Auto-induction of GPFuv expression in bioreactors. Triplicate 1 L bioreactors, with FGM10 minimal media were inoculated with DLF_R002 bearing plasmid pHCKan-yibDp-GFPuv. Optical density (black lines) and GFPuv were measured over time. Shaded area is standard error of triplicate growth profiles. X's, triangles and circles are normalized GFPuv fluorescence units from each of the three fermentations. Green line is the best fit of these three expression profiles. Biomass levels reached ~10 gCDW/L producing final GFPuv titers of ~2.7 g/L or 270 mg/gCDW.

Development of Phosphate Limited Media for Auto-Induc-tion

We next turned to the optimization of media formulations for more routine autoinduction via phosphate depletion. Importantly, the fermentations discussed above (FIG. 2) were performed with defined minimal media, which while lower in cost in larger scale production, can lead to signifi-cant lags when cells transition from a richer cloning and propagation media such as LB. In order to overcome this, seed cultures are often used to adapt the cells to a more minimal media (as they were in this case, refer to Methods) prior to inoculation of bioreactors. For routine lab scale protein expression, media adaptation is not desirable, and rather protocols enabling direct inoculation of production flasks from overnight LB cultures is preferred. As a result, we developed batch autoinduction broth with more complex nutrient sources including yeast extract and casamino acids. Media formulations were developed using standard Design of Experiments methodology (DoE) and evaluated in 96 well plates. These experiments were performed using strain DLF_R002 bearing plasmid pHCKan-yibDp-GFPuv, described above. Briefly, overnight LB cultures were used to inoculate various media in 96 well plates. Biomass and GFPuv levels were measured after 24 hours. Importantly, no phosphate was added to these media, as adequate batch phosphate is supplied in the complex nutrient sources (yeast extract and casamino acids). Results are given in FIG. 5 and Table 3.

Figures 5, 6:
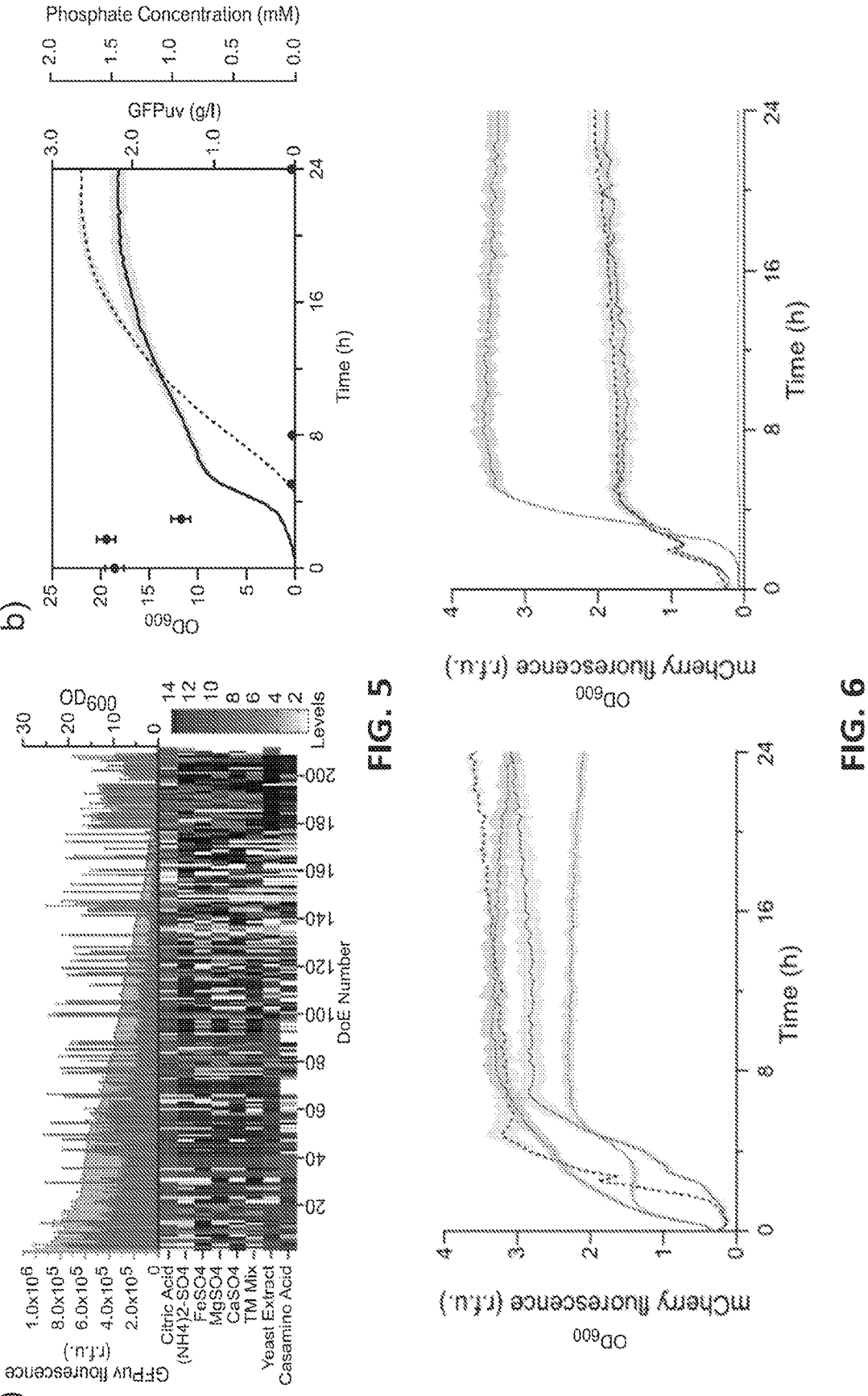
FIG. 6 are graphs showing Standard expression results using BL21(DE3). LB media with IPTG based induction in accordance with one aspect of the present disclosure.

Referring now to FIG. 5, 212 media formulations were evaluated for autoinduction based on phosphate depletion, each comprising different "levels" of casamino acids, yeast extract, trace metals (TM Mix), calcium sulfate (CaSO4), magnesium sulfate (MgSO4), iron(II) sulfate (FeSO4), ammonium sulfate ((NH4)2SO4) and citric acid. a) Upper panel: GFP (green bars) and OD600 nm (gray bars) rank ordered plot for all media formulations. Standard deviations are from triplicate experiments. Lower panel: Nutrient concentration levels for all media (Refer to Materials and methods Media Section). Strain DLF_R002 with plasmid pHCKan-yibDp-GFPuv was used for all experiments. b). GFP fluorescence (green line), phosphate levels (black circles) and OD600 nm (black line) for strain DLF_R002 with plasmid pHCKan-yibDp-GFPuv in media #36 (Autoinduction Broth, AB) media. Standard deviations (shaded regions) are from triplicate experiments.

Models built based on these results did not predict significant improvements in expression over the best performing experimentally tested formulations FIG. 5A. The media formulation producing the most GFPuv (as measured by relative fluorescence), was renamed AB (autoinduction broth) and used in subsequent studies. To evaluate the time course of growth, phosphate depletion and autoinduction in AB, DLF_R002 pHCKan-yibDp-GFPuv, was grown in AB in the Biolector™ Microreactor. Results are given in FIG. 5B.

TABLE 3

| DoE# | Citric Acid (g/L) | (NH4)2-SO4 (mM) | FeSO4 (mM) | MgSO4 (mM) | CaSO4 (mM) | TM Mix (X) | Yeast Extract (g/L) | Casamino Acid (g/L) | GFP_avg rfu |
|---|---|---|---|---|---|---|---|---|---|
| 35 | 0.08 | 22.67 | 0.48 | 3.33 | 0.1875 | 0.67 | 2.50 | 7.500 | 923080.00 |
| 131 | 0.25 | 40.8 | 0.096 | 8.7 | 0.0708 | 2.8 | 6.2 | 3.50 | 894636.67 |
| 11 | 0.0625 | 17 | 0.64 | 2.5 | 0.2500 | 0.5 | 2.5 | 10.000 | 869846.67 |
| 154 | 0.25 | 40.8 | 0.18 | 14.0 | 0.0375 | 2.8 | 3.5 | 3.50 | 833390.00 |
| 121 | 0.25 | 58.9 | 0.18 | 11.3 | 0.0875 | 1.2 | 6.2 | 3.50 | 809213.33 |
| 79 | 0.08 | 22.67 | 0.053 | 30.00 | 0.1875 | 0.67 | 7.50 | 0.833 | 804133.33 |
| 45 | 0.75 | 22.67 | 0.48 | 30.00 | 0.0208 | 2.00 | 7.50 | 0.833 | 792280.00 |
| 145 | 0.25 | 40.8 | 0.096 | 8.7 | 0.0375 | 1.2 | 3.5 | 8.833 | 770306.67 |
| 140 | 0.25 | 40.8 | 0.22 | 6.0 | 0.0375 | 2.3 | 3.5 | 3.500 | 769233.33 |
| 142 | 0.25 | 95.2 | 0.22 | 14.0 | 0.0875 | 1.2 | 3.5 | 6.167 | 757346.67 |
| 80 | 0.75 | 22.67 | 0.48 | 30.00 | 0.0208 | 2.00 | 7.50 | 0.833 | 751280.00 |
| 107 | 0.08 | 22.67 | 0.48 | 3.33 | 0.1875 | 0.67 | 2.50 | 7.500 | 750830.00 |
| 36 | 0.08 | 22.67 | 0.48 | 3.33 | 0.0208 | 6.00 | 7.50 | 2.500 | 748506.67 |
| 141 | 0.25 | 40.8 | 0.096 | 14.0 | 0.0875 | 1.7 | 3.5 | 3.500 | 740573.33 |
| 138 | 0.25 | 95.2 | 0.22 | 14.0 | 0.0875 | 2.8 | 3.5 | 3.50 | 736593.33 |
| 168 | 0.25 | 95.2 | 0.096 | 14.0 | 0.0375 | 1.2 | 3.5 | 3.500 | 735546.67 |
| 151 | 0.25 | 40.8 | 0.22 | 14.0 | 0.054 | 1.2 | 3.5 | 3.500 | 723266.67 |
| 129 | 0.25 | 40.8 | 0.18 | 6.0 | 0.0875 | 2.8 | 3.5 | 3.50 | 672653.33 |
| 152 | 0.25 | 95.2 | 0.096 | 6.0 | 0.0875 | 1.2 | 3.5 | 3.500 | 659113.33 |
| 144 | 0.25 | 95.2 | 0.096 | 6.0 | 0.0375 | 2.8 | 3.5 | 3.50 | 638486.67 |
| 6 | 1 | 17 | 0.64 | 40 | 0.0625 | 0.5 | 0.625 | 10.000 | 634900.00 |
| 103 | 0.75 | 22.67 | 0.48 | 30.00 | 0.06250 | 0.67 | 0.83 | 7.500 | 620180.00 |
| 41 | 0.08 | 22.67 | 0.053 | 30.00 | 0.0208 | 6.00 | 0.83 | 7.500 | 619766.67 |
| 28 | 0.25 | 68.00 | 0.160 | 10.00 | 0.06250 | 2.00 | 2.50 | 2.500 | 618400.00 |
| 66 | 0.50 | 136.00 | 0.32 | 20.00 | 0.1250 | 4.00 | 5.00 | 5.00 | 612493.33 |
| 18 | 0.25 | 68 | 0.160 | 10 | 0.0625 | 2 | 2.5 | 2.500 | 610520.00 |
| 30 | 0.75 | 22.67 | 0.48 | 30.00 | 0.06252 | 0.67 | 0.83 | 7.500 | 609706.67 |
| 4 | 0.25 | 68 | 0.160 | 10 | 0.0625 | 2 | 2.5 | 2.500 | 608533.33 |
| 44 | 0.75 | 22.67 | 0.053 | 10.00 | 0.1875 | 6.00 | 7.50 | 7.500 | 604673.33 |
| 106 | 0.08 | 22.67 | 0.053 | 30.00 | 0.0208 | 6.00 | 0.83 | 7.500 | 597006.67 |
| 17 | 0.0625 | 17 | 0.040 | 40 | 0.015625 | 8 | 0.625 | 10.000 | 595880.00 |
| 42 | 0.25 | 68.00 | 0.160 | 10.00 | 0.06250 | 2.00 | 2.50 | 2.500 | 593406.67 |
| 94 | 0.25 | 68.00 | 0.160 | 10.00 | 0.06250 | 2.00 | 2.50 | 2.500 | 592140.00 |
| 92 | 0.25 | 68.00 | 0.160 | 10.00 | 0.06250 | 2.00 | 2.50 | 2.500 | 591080.00 |
| 96 | 0.08 | 22.67 | 0.48 | 3.33 | 0.0208 | 6.00 | 7.50 | 2.500 | 581180.00 |
| 47 | 0.25 | 68.00 | 0.160 | 10.00 | 0.06252 | 2.00 | 2.50 | 2.500 | 580413.33 |
| 95 | 0.25 | 68.00 | 0.160 | 10.00 | 0.06250 | 2.00 | 2.50 | 2.500 | 577146.67 |
| 23 | 0.25 | 68 | 0.160 | 10 | 0.0625 | 2 | 2.5 | 2.500 | 576760.00 |
| 93 | 0.25 | 68.00 | 0.160 | 10.00 | 0.06250 | 2.00 | 2.50 | 2.500 | 568446.67 |
| 48 | 0.25 | 68.00 | 0.160 | 10.00 | 0.06250 | 2.00 | 2.50 | 2.500 | 562220.00 |
| 98 | 0.50 | 136.00 | 0.32 | 20.00 | 0.1250 | 4.00 | 5.00 | 5.00 | 560253.33 |
| 196 | 0.375 | 204 | 0.32 | 30 | 0.09375 | 3 | 7.5 | 0 | 560246.67 |
| 125 | 0.25 | 58.9 | 0.096 | 14.0 | 0.054 | 2.8 | 3.5 | 8.833 | 558153.33 |
| 100 | 0.50 | 136.00 | 0.32 | 20.00 | 0.1250 | 4.00 | 5.00 | 5.00 | 555846.67 |
| 24 | 0.25 | 68 | 0.160 | 10 | 0.0625 | 2 | 2.5 | 2.500 | 552273.33 |
| 101 | 0.50 | 136.00 | 0.32 | 20.00 | 0.1250 | 4.00 | 5.00 | 5.000 | 549346.67 |
| 21 | 1 | 17 | 0.64 | 40 | 0.015625 | 2 | 10 | 0.625 | 548126.67 |
| 71 | 0.50 | 136.00 | 0.32 | 20.00 | 0.1250 | 4.00 | 5.00 | 5.00 | 546046.67 |
| 110 | 0.75 | 22.67 | 0.053 | 10.00 | 0.1875 | 6.00 | 7.50 | 7.500 | 539300.00 |
| 99 | 0.50 | 136.00 | 0.32 | 20.00 | 0.1250 | 4.00 | 5.00 | 5.00 | 532993.33 |
| 206 | 0.375 | 102 | 0.48 | 15 | 0.09375 | 6 | 7.5 | 0 | 531020.00 |
| 25 | 0.08 | 22.67 | 0.053 | 30.00 | 0.1875 | 0.67 | 7.50 | 0.833 | 519413.33 |
| 201 | 0.75 | 102 | 0.48 | 30 | 0.09375 | 4 | 7.5 | 0 | 516300.00 |
| 158 | 0.25 | 40.8 | 0.22 | 6.0 | 0.0875 | 1.2 | 3.5 | 11.500 | 510960.00 |
| 197 | 0.75 | 102 | 0.24 | 20 | 0.1875 | 6 | 7.5 | 0 | 510473.33 |
| 52 | 0.50 | 136.00 | 0.32 | 20.00 | 0.1250 | 4.00 | 5.00 | 5.00 | 498526.67 |
| 72 | 0.50 | 136.00 | 0.32 | 20.00 | 0.1250 | 4.00 | 5.00 | 5.00 | 489853.33 |
| 124 | 0.25 | 95.2 | 0.22 | 6.0 | 0.0375 | 1.2 | 3.5 | 8.833 | 483866.67 |
| 38 | 0.75 | 204.00 | 0.48 | 3.33 | 0.1875 | 0.67 | 7.50 | 0.833 | 477746.67 |
| 1 | 0.0625 | 17 | 0.040 | 40 | 0.2500 | 0.5 | 10 | 0.625 | 468660.00 |

TABLE 3-continued

| DoE# | Citric Acid (g/L) | (NH4)2-SO4 (mM) | FeSO4 (mM) | MgSO4 (mM) | CaSO4 (mM) | TM Mix (X) | Yeast Extract (g/L) | Casamino Acid (g/L) | GFP_avg rfu |
|---|---|---|---|---|---|---|---|---|---|
| 208 | 0.375 | 102 | 0.24 | 30 | 0.1875 | 3 | 7.5 | 0 | 461880.00 |
| 78 | 0.75 | 204.00 | 0.48 | 3.33 | 0.1875 | 0.67 | 7.50 | 0.833 | 459120.00 |
| 81 | 0.08 | 204.00 | 0.053 | 3.33 | 0.06250 | 6.00 | 7.50 | 0.833 | 443886.67 |
| 186 | 0.0625 | 17 | 0.040 | 10 | 0.0625 | 0.5 | 2.5 | 0 | 441833.33 |
| 164 | 0.25 | 95.2 | 0.096 | 14.0 | 0.0875 | 2.8 | 8.8 | 3.50 | 441333.33 |
| 12 | 0.0625 | 17 | 0.64 | 2.5 | 0.015625 | 8 | 10 | 2.500 | 440173.33 |
| 200 | 0.375 | 204 | 0.24 | 15 | 0.125 | 6 | 7.5 | 0 | 437506.67 |
| 193 | 0.75 | 136 | 0.24 | 15 | 0.09375 | 3 | 7.5 | 0 | 434926.67 |
| 204 | 0.375 | 102 | 0.48 | 15 | 0.1875 | 3 | 5 | 0 | 432926.67 |
| 209 | 0.75 | 204 | 0.48 | 15 | 0.1875 | 3 | 7.5 | 0 | 432520.00 |
| 191 | 0.5 | 204 | 0.48 | 30 | 0.1875 | 6 | 7.5 | 0 | 431840.00 |
| 192 | 0.500 | 102 | 0.24 | 15 | 0.09375 | 3 | 3.75 | 0 | 427713.33 |
| 29 | 0.08 | 204.00 | 0.053 | 3.33 | 0.06250 | 6.00 | 7.50 | 0.833 | 420013.33 |
| 84 | 1.50 | 45.33 | 0.35 | 6.67 | 0.3750 | 12.00 | 1.67 | 1.667 | 408113.33 |
| 40 | 0.75 | 68.00 | 0.053 | 3.33 | 0.0208 | 0.67 | 7.50 | 7.500 | 405066.67 |
| 133 | 0.25 | 95.2 | 0.096 | 8.7 | 0.0875 | 2.8 | 3.5 | 11.500 | 404320.00 |
| 108 | 0.75 | 68.00 | 0.053 | 3.33 | 0.0208 | 0.67 | 7.50 | 7.500 | 401573.33 |
| 58 | 0.500 | 45.33 | 0.107 | 6.67 | 0.0417 | 1.33 | 1.67 | 1.667 | 396760.00 |
| 57 | 1.50 | 45.33 | 0.32 | 6.67 | 0.3750 | 12.00 | 1.67 | 1.667 | 390766.67 |
| 160 | 0.25 | 95.2 | 0.22 | 6.0 | 0.054 | 2.8 | 3.5 | 11.500 | 372053.33 |
| 82 | 0.500 | 45.33 | 0.107 | 6.67 | 0.0417 | 1.33 | 1.67 | 1.667 | 370346.67 |
| 161 | 0.25 | 40.8 | 0.096 | 6.0 | 0.0375 | 2.8 | 3.5 | 11.500 | 364473.33 |
| 203 | 0.75 | 204 | 0.24 | 30 | 0.09675 | 6 | 5 | 0 | 360973.33 |
| 174 | 0.0625 | 68 | 0.080 | 10 | 0.015625 | 0.5 | 2.5 | 0 | 352406.67 |
| 130 | 0.25 | 40.8 | 0.22 | 14.0 | 0.0875 | 2.8 | 3.5 | 11.50 | 352366.67 |
| 175 | 0.25 | 17 | 0.040 | 5 | 0.0625 | 2 | 2.5 | 0 | 344373.33 |
| 156 | 0.25 | 95.2 | 0.139 | 14.0 | 0.0375 | 1.7 | 3.5 | 11.500 | 340160.00 |
| 167 | 0.25 | 77.1 | 0.096 | 14.0 | 0.0708 | 1.2 | 3.5 | 11.500 | 339820.00 |
| 212 | 0.5 | 136 | 0.32 | 20 | 0.125 | 4 | 5 | 0 | 339093.33 |
| 169 | 0.125 | 68 | 0.160 | 10 | 0.0625 | 2 | 2.5 | 0 | 335173.33 |
| 199 | 0.75 | 102 | 0.48 | 30 | 0.125 | 3 | 3.75 | 0 | 335173.33 |
| 178 | 0.0625 | 68 | 0.040 | 2.5 | 0.03125 | 2 | 2.5 | 0 | 332113.33 |
| 50 | 1.50 | 408.00 | 0.107 | 60.00 | 0.0417 | 12.00 | 5.00 | 1.667 | 331033.33 |
| 211 | 0.5 | 136 | 0.32 | 20 | 0.125 | 4 | 5 | 0 | 328906.67 |
| 77 | 0.75 | 204.00 | 0.053 | 30.00 | 0.0208 | 6.00 | 2.50 | 0.833 | 319100.00 |
| 202 | 0.375 | 204 | 0.24 | 15 | 0.1875 | 4 | 3.75 | 0 | 312226.67 |
| 26 | 0.75 | 204.00 | 0.053 | 30.00 | 0.0208 | 6.00 | 2.50 | 0.833 | 311500.00 |
| 86 | 1.50 | 408.00 | 0.107 | 60.00 | 0.0417 | 12.00 | 5.00 | 1.667 | 304073.33 |
| 137 | 0.25 | 40.8 | 0.096 | 6.0 | 0.0375 | 1.2 | 11.5 | 3.50 | 301140.00 |
| 126 | 0.25 | 58.9 | 0.096 | 6.0 | 0.0875 | 2.8 | 11.5 | 3.50 | 300240.00 |
| 210 | 0.375 | 102 | 0.24 | 30 | 0.09375 | 6 | 3.75 | 0 | 297686.67 |
| 51 | 1.50 | 408.00 | 0.96 | 6.67 | 0.0417 | 12.00 | 1.67 | 15.00 | 297560.00 |
| 3 | 1 | 272 | 0.64 | 2.5 | 0.015625 | 8 | 0.625 | 10.000 | 287040.00 |
| 150 | 0.25 | 95.2 | 0.096 | 14.0 | 0.0875 | 1.2 | 11.5 | 3.50 | 286353.33 |
| 148 | 0.25 | 40.8 | 0.22 | 14.0 | 0.0375 | 1.2 | 3.5 | 11.500 | 282466.67 |
| 205 | 0.75 | 204 | 0.24 | 30 | 0.1875 | 3 | 3.75 | 0 | 281906.67 |
| 184 | 0.0625 | 17 | 0.160 | 2.5 | 0.015625 | 2 | 2.5 | 0 | 281560.00 |
| 105 | 0.75 | 204.00 | 0.48 | 3.33 | 0.0208 | 6.00 | 0.83 | 7.50 | 280600.00 |
| 198 | 0.375 | 204 | 0.48 | 20 | 0.09375 | 3 | 3.75 | 0 | 278360.00 |
| 39 | 0.08 | 204.00 | 0.053 | 3.33 | 0.1875 | 2.00 | 0.83 | 7.500 | 275633.33 |
| 27 | 0.75 | 204.00 | 0.48 | 3.33 | 0.0208 | 6.00 | 0.83 | 7.500 | 274700.00 |
| 111 | 0.25 | 204.00 | 0.48 | 30.00 | 0.1875 | 6.00 | 7.50 | 7.500 | 269800.00 |
| 194 | 0.375 | 136 | 0.48 | 30 | 0.1875 | 6 | 3.75 | 0 | 269540.00 |
| 207 | 0.75 | 204 | 0.48 | 15 | 0.06375 | 6 | 3.75 | 0 | 266620.00 |
| 104 | 0.08 | 204.00 | 0.053 | 3.33 | 0.1875 | 2.00 | 0.83 | 7.500 | 263860.00 |
| 122 | 0.25 | 77.1 | 0.096 | 11.3 | 0.0375 | 1.7 | 11.5 | 6.167 | 253373.33 |
| 65 | 0.17 | 45.33 | 0.107 | 60.00 | 0.0417 | 12.00 | 1.67 | 15.00 | 248406.67 |
| 195 | 0.75 | 102 | 0.32 | 15 | 0.1875 | 6 | 3.75 | 0 | 237800.00 |
| 146 | 0.25 | 40.8 | 0.22 | 6.0 | 0.0875 | 1.2 | 11.5 | 6.167 | 235120.00 |
| 2 | 1 | 272 | 0.040 | 40 | 0.015625 | 8 | 2.5 | 0.625 | 232480.00 |
| 15 | 0.0625 | 272 | 0.040 | 2.5 | 0.2500 | 2 | 0.625 | 10.000 | 232200.00 |
| 143 | 0.25 | 95.2 | 0.22 | 6.0 | 0.0375 | 2.8 | 11.5 | 3.50 | 229160.00 |
| 114 | 1.50 | 408.00 | 0.96 | 6.67 | 0.0417 | 12.00 | 1.67 | 15.00 | 229040.00 |
| 73 | 0.25 | 22.67 | 0.053 | 3.33 | 0.0208 | 0.67 | 0.83 | 0.833 | 217966.67 |
| 157 | 0.25 | 77.1 | 0.139 | 6.0 | 0.0708 | 2.3 | 8.8 | 8.833 | 217773.33 |
| 32 | 0.25 | 204.00 | 0.48 | 30.00 | 0.1875 | 6.00 | 7.50 | 7.500 | 213693.33 |
| 37 | 0.75 | 204.00 | 0.053 | 30.00 | 0.1875 | 0.67 | 0.83 | 2.500 | 206113.33 |
| 162 | 0.25 | 77.1 | 0.22 | 14.0 | 0.0375 | 2.8 | 8.8 | 11.500 | 202253.33 |
| 190 | 0.125 | 34 | 0.080 | 5 | 0.03125 | 1 | 1.25 | 0 | 199606.67 |
| 61 | 1.50 | 408.00 | 0.107 | 60.00 | 0.3750 | 1.33 | 1.67 | 5.00 | 194926.67 |
| 91 | 0.75 | 204.00 | 0.053 | 30.00 | 0.1875 | 0.67 | 0.83 | 2.500 | 193053.33 |
| 33 | 0.75 | 22.67 | 0.160 | 3.33 | 0.1875 | 6.00 | 0.83 | 0.833 | 192853.33 |
| 134 | 0.25 | 95.2 | 0.22 | 6.0 | 0.0875 | 1.2 | 11.5 | 3.50 | 189013.33 |
| 181 | 0.25 | 68 | 0.040 | 10 | 0.015625 | 2 | 1.25 | 0 | 187606.67 |
| 34 | 0.25 | 22.67 | 0.053 | 3.33 | 0.0208 | 0.67 | 0.83 | 0.833 | 183253.33 |
| 182 | 0.0625 | 17 | 0.160 | 2.5 | 0.0625 | 0.5 | 1.25 | 0 | 182566.67 |
| 189 | 0.125 | 34 | 0.080 | 5 | 0.03125 | 1 | 1.25 | 0 | 177126.67 |

TABLE 3-continued

| DoE# | Citric Acid (g/L) | (NH4)2-SO4 (mM) | FeSO4 (mM) | MgSO4 (mM) | CaSO4 (mM) | TM Mix (X) | Yeast Extract (g/L) | Casamino Acid (g/L) | GFP_avg rfu |
|---|---|---|---|---|---|---|---|---|---|
| 75 | 0.75 | 22.67 | 0.160 | 3.33 | 0.1875 | 6.00 | 0.83 | 0.833 | 175793.33 |
| 13 | 1 | 272 | 0.040 | 40 | 0.2500 | 0.5 | 0.625 | 2.500 | 167500.00 |
| 9 | 1 | 17 | 0.160 | 2.5 | 0.2500 | 8 | 0.625 | 0.625 | 162086.67 |
| 159 | 0.25 | 95.2 | 0.096 | 6.0 | 0.0875 | 1.7 | 6.2 | 11.500 | 157100.00 |
| 97 | 1.50 | 408.00 | 0.107 | 60.00 | 0.3750 | 1.33 | 1.67 | 5.00 | 154913.33 |
| 54 | 1.50 | 45.33 | 0.96 | 60.00 | 0.1250 | 1.33 | 1.67 | 15.00 | 152393.33 |
| 31 | 0.08 | 204.00 | 0.160 | 30.00 | 0.202 | 0.67 | 7.50 | 7.500 | 148880.00 |
| 149 | 0.25 | 95.2 | 0.22 | 14.0 | 0.0375 | 1.2 | 11.5 | 3.50 | 146846.67 |
| 59 | 0.17 | 45.33 | 0.96 | 6.67 | 0.3750 | 1.33 | 5.00 | 15.00 | 142466.67 |
| 115 | 0.17 | 45.33 | 0.107 | 60.00 | 0.0417 | 12.00 | 1.67 | 15.00 | 130160.00 |
| 170 | 0.125 | 17 | 0.040 | 2.5 | 0.015625 | 0.5 | 0.625 | 0 | 127993.33 |
| 74 | 0.08 | 204.00 | 0.48 | 10.00 | 0.0208 | 0.67 | 0.83 | 0.833 | 127760.00 |
| 10 | 0.25 | 17 | 0.040 | 2.5 | 0.015625 | 0.5 | 0.625 | 0.625 | 125726.67 |
| 136 | 0.25 | 95.2 | 0.18 | 14.0 | 0.0708 | 2.8 | 11.5 | 6.167 | 122813.33 |
| 177 | 0.25 | 17 | 0.160 | 10 | 0.03125 | 0.5 | 0.625 | 0 | 115800.00 |
| 43 | 0.08 | 204.00 | 0.48 | 10.00 | 0.0208 | 0.67 | 0.83 | 0.833 | 115033.33 |
| 116 | 0.17 | 45.33 | 0.96 | 6.67 | 0.3750 | 1.33 | 5.00 | 15.00 | 108586.67 |
| 173 | 0.25 | 17 | 0.080 | 2.5 | 0.0625 | 2 | 0.625 | 0 | 106286.67 |
| 76 | 0.08 | 68.00 | 0.48 | 30.00 | 0.1875 | 6.00 | 0.83 | 0.833 | 105486.67 |
| 172 | 0.0625 | 34 | 0.160 | 10 | 0.0625 | 2 | 0.625 | 1 | 101000.00 |
| 109 | 0.08 | 204.00 | 0.160 | 30.00 | 0.0208 | 0.67 | 7.50 | 7.500 | 100233.33 |
| 180 | 0.0625 | 68 | 0.040 | 2.5 | 0.0625 | 1 | 0.625 | 0 | 100066.67 |
| 5 | 0.0625 | 272 | 0.040 | 2.5 | 0.0625 | 8 | 10 | 0.625 | 98900.00 |
| 67 | 0.17 | 408.00 | 0.96 | 20.00 | 0.0417 | 1.33 | 1.67 | 1.667 | 97746.67 |
| 185 | 0.25 | 68 | 0.160 | 2.5 | 0.01563 | 2 | 0.625 | 0 | 93806.67 |
| 188 | 0.0625 | 17 | 0.040 | 10 | 0.01563 | 2 | 0.625 | 0 | 92373.33 |
| 113 | 0.17 | 408.00 | 0.107 | 6.67 | 0.3750 | 4.00 | 1.67 | 15.00 | 87893.33 |
| 49 | 0.17 | 45.33 | 0.107 | 60.00 | 0.3750 | 1.33 | 15.00 | 1.667 | 86640.00 |
| 112 | 1.50 | 45.33 | 0.96 | 60.00 | 0.1250 | 1.33 | 1.67 | 15.00 | 86366.67 |
| 70 | 0.17 | 136.00 | 0.96 | 60.00 | 0.3750 | 12.00 | 1.67 | 1.667 | 85626.67 |
| 183 | 0.25 | 68 | 0.040 | 10 | 0.0625 | 0.5 | 0.625 | 0 | 82486.67 |
| 14 | 1 | 272 | 0.64 | 2.5 | 0.2500 | 0.5 | 10 | 0.625 | 80993.33 |
| 85 | 0.17 | 136.00 | 0.96 | 60.00 | 0.3750 | 12.00 | 1.67 | 1.667 | 78486.67 |
| 176 | 0.0625 | 68 | 0.160 | 5 | 0.01563 | 0.5 | 0.625 | 0 | 74006.67 |
| 69 | 1.50 | 45.33 | 0.96 | 60.00 | 0.0417 | 4.00 | 15.00 | 1.667 | 72093.33 |
| 19 | 0.0625 | 272 | 0.64 | 10 | 0.01563 | 0.5 | 0.625 | 0.625 | 68033.33 |
| 83 | 0.17 | 408.00 | 0.96 | 20.00 | 0.0417 | 1.33 | 1.67 | 1.667 | 63906.67 |
| 88 | 0.17 | 45.33 | 0.107 | 60.00 | 0.3750 | 1.33 | 15.00 | 1.667 | 57546.67 |
| 63 | 0.17 | 408.00 | 0.107 | 6.67 | 0.3750 | 4.00 | 1.67 | 15.00 | 56766.67 |
| 46 | 0.08 | 68.00 | 0.48 | 30.00 | 0.1875 | 6.00 | 0.83 | 0.833 | 54626.67 |
| 89 | 1.50 | 45.33 | 0.96 | 60.00 | 0.0417 | 4.00 | 15.00 | 1.667 | 35573.33 |
| 127 | 0.25 | 95.2 | 0.096 | 6.0 | 0.0375 | 1.2 | 11.5 | 11.500 | 24613.33 |
| 102 | 0.17 | 45.33 | 0.96 | 6.67 | 0.0417 | 12.00 | 15.00 | 5.000 | 21280.00 |
| 135 | 0.25 | 40.8 | 0.22 | 6.0 | 0.0375 | 2.8 | 11.5 | 8.833 | 20753.33 |
| 20 | 1 | 17 | 0.040 | 10 | 0.2500 | 8 | 10 | 10.000 | 20433.33 |
| 132 | 0.25 | 95.2 | 0.096 | 14.0 | 0.0375 | 2.8 | 11.5 | 11.500 | 20400.00 |
| 165 | 0.25 | 58.9 | 0.22 | 6.0 | 0.0375 | 1.2 | 11.5 | 11.5800 | 20233.33 |
| 53 | 0.17 | 408.00 | 0.107 | 6.67 | 0.1250 | 12.00 | 15.00 | 1.667 | 20220.00 |
| 16 | 1 | 68 | 0.040 | 2.5 | 0.01563 | 0.5 | 10 | 10.000 | 19953.33 |
| 155 | 0.25 | 40.8 | 0.22 | 14.0 | 0.0875 | 2.8 | 11.5 | 3.50 | 19806.67 |
| 128 | 0.25 | 95.2 | 0.22 | 14.0 | 0.0875 | 1.2 | 11.5 | 11.500 | 19540.00 |
| 147 | 0.25 | 40.8 | 0.096 | 14.0 | 0.0375 | 2.8 | 11.5 | 3.50 | 1948.00 |
| 163 | 0.25 | 95.2 | 0.22 | 6.0 | 0.0875 | 2.8 | 11.5 | 11.500 | 19286.67 |
| 117 | 1.50 | 136.00 | 0.107 | 6.67 | 0.0417 | 1.33 | 15.00 | 15.00 | 18693.33 |
| 153 | 0.25 | 40.8 | 0.096 | 14.0 | 0.0375 | 1.2 | 11.5 | 11.500 | 18506.67 |
| 64 | 1.50 | 136.00 | 0.107 | 6.67 | 0.0417 | 1.33 | 15.00 | 15.00 | 18173.33 |
| 60 | 0.17 | 45.33 | 0.96 | 6.67 | 0.0417 | 12.00 | 15.00 | 5.000 | 17720.00 |
| 119 | 1.50 | 45.33 | 0.107 | 20.00 | 0.3750 | 12.00 | 15.00 | 15.00 | 17560.00 |
| 68 | 1.50 | 45.33 | 0.107 | 20.00 | 0.3750 | 12.00 | 15.00 | 15.00 | 17413.33 |
| 22 | 0.0625 | 68 | 0.64 | 40 | 0.2500 | 8 | 0.625 | 0.625 | 17353.33 |
| 90 | 0.17 | 408.00 | 0.107 | 6.67 | 0.1250 | 12.00 | 15.00 | 1.667 | 17193.33 |
| 55 | 0.17 | 408.00 | 0.32 | 60.00 | 0.0417 | 1.33 | 15.00 | 15.00 | 17093.33 |
| 62 | 1.50 | 408.00 | 0.96 | 6.67 | 0.3750 | 1.33 | 15.00 | 1.667 | 17046.67 |
| 87 | 1.50 | 408.00 | 0.96 | 6.67 | 0.9750 | 1.33 | 15.00 | 1.667 | 16920.00 |
| 139 | 0.25 | 40.8 | 0.096 | 6.0 | 0.0875 | 1.2 | 11.5 | 11.500 | 16886.67 |
| 120 | 0.50 | 408.00 | 0.96 | 60.00 | 0.3750 | 12.00 | 15.00 | 15.00 | 16273.33 |
| 7 | 0.0625 | 272 | 0.160 | 40 | 0.01563 | 0.5 | 10 | 10 | 15586.67 |
| 56 | 0.50 | 408.00 | 0.96 | 60.00 | 0.3750 | 12.00 | 15.00 | 15.00 | 15480.00 |
| 8 | 0.25 | 272 | 0.64 | 40 | 0.2500 | 8 | 10 | 10.000 | 14440.00 |
| 166 | 0.25 | 40.8 | 0.18 | 8.7 | 0.054 | 2.3 | 11.5 | 11.500 | 13440.00 |
| 123 | 0.25 | 40.8 | 0.096 | 14.0 | 0.0875 | 2.8 | 11.5 | 11.500 | 12126.67 |
| 118 | 0.17 | 408.00 | 0.32 | 60.00 | 0.0417 | 1.33 | 15.00 | 15.00 | 11933.33 |

TABLE 3-continued

| DoE# | Citric Acid (g/L) | (NH4)2-SO4 (mM) | FeSO4 (mM) | MgSO4 (mM) | CaSO4 (mM) | TM Mix (X) | Yeast Extract (g/L) | Casamino Acid (g/L) | GFP_avg rfu |
|---|---|---|---|---|---|---|---|---|---|
| 179 | 0.25 | 17 | 0.160 | 10 | 0.01563 | 1 | 2.5 | 0 | 5260.00 |
| 187 | 0.25 | 68 | 0.160 | 2.5 | 0.0625 | 0.5 | 2.5 | 0 | 5166.67 |
| 171 | 0.25 | 34 | 0.040 | 2.5 | 0.01563 | 0.5 | 2.5 | 0 | 4966.67 |

| DoE# | OD_avg | GFP_std | OD_std | | g/L (NH4)2(SO4) | Sum of Complex Nutrients (CA + YE) | Sum of YE & Casamino Acids (5-15 g/L) | (NH4)2(S)4 (<200 mM, <400 mM NH4) |
|---|---|---|---|---|---|---|---|---|
| 35 | 15.93 | 73732.20 | 1.13 | | 3.00 | 10.00 | 1 | 1 |
| 131 | 20.16 | 18453.05 | 0.33 | AB | 5.39 | 9.67 | 1 | 1 |
| 11 | 21.24 | 147932.00 | 0.51 | | 2.25 | 12.50 | 1 | 1 |
| 154 | 13.00 | 33939.92 | 0.89 | | 5.39 | 7.00 | 1 | 1 |
| 121 | 18.38 | 34964.54 | 0.87 | | 7.79 | 9.67 | 1 | 1 |
| 79 | 16.62 | 35830.77 | 0.17 | | 3.00 | 8.33 | 1 | 1 |
| 45 | 16.58 | 19996.13 | 0.60 | | 3.00 | 8.33 | 1 | 1 |
| 145 | 20.87 | 75600.60 | 0.73 | | 5.39 | 12.33 | 1 | 1 |
| 140 | 11.88 | 51000.84 | 0.80 | | 5.39 | 7.00 | 1 | 1 |
| 142 | 13.71 | 11806.85 | 0.91 | | 12.58 | 9.67 | 1 | 1 |
| 80 | 16.33 | 105765.33 | 1.40 | | 3.00 | 8.33 | 1 | 1 |
| 107 | 15.88 | 206983.51 | 0.65 | | 3.00 | 10.00 | 1 | 1 |
| 36 | 21.36 | 104866.79 | 0.11 | | 3.00 | 10.00 | 1 | 1 |
| 141 | 10.68 | 35788.01 | 0.52 | | 5.39 | 7.00 | 1 | 1 |
| 138 | 11.94 | 6399.45 | 0.46 | | 12.58 | 7.00 | 1 | 1 |
| 168 | 12.52 | 54167.72 | 0.57 | | 12.58 | 7.00 | 1 | 1 |
| 151 | 10.42 | 46086.76 | 0.84 | | 5.39 | 7.00 | 1 | 1 |
| 129 | 9.64 | 11410.81 | 0.40 | | 5.39 | 7.00 | 1 | 1 |
| 152 | 11.08 | 44277.49 | 0.45 | | 12.58 | 7.00 | 1 | 1 |
| 144 | 11.54 | 39910.05 | 1.08 | | 12.58 | 7.00 | 1 | 1 |
| 6 | 13.90 | 69559.25 | 0.38 | | 2.25 | 10.63 | 1 | 1 |
| 103 | 11.51 | 49098.71 | 0.87 | | 3.00 | 8.33 | 1 | 1 |
| 41 | 9.80 | 25844.99 | 0.71 | | 3.00 | 8.33 | 1 | 1 |
| 28 | 8.52 | 12533.75 | 0.49 | AB-C7 | 8.99 | 5.00 | 1 | 1 |
| 66 | 12.34 | 56046.80 | 1.53 | | 17.97 | 10.00 | 1 | 1 |
| 18 | 8.44 | 20927.65 | 0.24 | | 8.99 | 5.00 | 1 | 1 |
| 30 | 10.73 | 13373.41 | 0.99 | | 3.00 | 8.33 | 1 | 1 |
| 4 | 8.09 | 11715.40 | 0.65 | | 8.99 | 5.00 | 1 | 1 |
| 44 | 24.11 | 13662.46 | 1.13 | | 3.00 | 15.00 | 1 | 1 |
| 106 | 10.48 | 15660.53 | 0.19 | | 3.00 | 8.33 | 1 | 1 |
| 17 | 12.14 | 38348.81 | 0.48 | | 2.25 | 10.63 | 1 | 1 |
| 42 | 8.40 | 5286.68 | 0.53 | | 8.99 | 5.00 | 1 | 1 |
| 94 | 7.85 | 26018.39 | 0.81 | | 8.99 | 5.00 | 1 | 1 |
| 92 | 8.15 | 13464.50 | 0.65 | | 8.99 | 5.00 | 1 | 1 |
| 96 | 20.74 | 171796.68 | 0.58 | | 3.00 | 10.00 | 1 | 1 |
| 47 | 7.74 | 25400.48 | 0.28 | | 8.99 | 5.00 | 1 | 1 |
| 95 | 7.44 | 28359.88 | 0.54 | | 8.99 | 5.00 | 1 | 1 |
| 23 | 7.63 | 20550.69 | 0.48 | | 8.99 | 5.00 | 1 | 1 |
| 93 | 7.29 | 7078.20 | 0.20 | | 8.99 | 5.00 | 1 | 1 |
| 48 | 8.44 | 31286.54 | 0.14 | | 8.99 | 5.00 | 1 | 1 |
| 98 | 12.48 | 16950.94 | 0.56 | | 17.97 | 10.00 | 1 | 1 |
| 196 | 14.73 | 22490.62 | 1.48 | | 26.96 | 7.50 | 1 | 0 |
| 125 | 20.92 | 54014.70 | 0.55 | | 7.79 | 12.33 | 1 | 1 |
| 100 | 14.15 | 32526.18 | 0.67 | | 17.97 | 10.00 | 1 | 1 |
| 24 | 8.24 | 14496.79 | 0.31 | | 8.99 | 5.00 | 1 | 1 |
| 101 | 12.72 | 35540.45 | 0.85 | | 17.97 | 10.00 | 1 | 1 |
| 21 | 20.74 | 58465.63 | 0.52 | | 2.25 | 10.63 | 1 | 1 |
| 71 | 12.40 | 38057.75 | 0.72 | | 17.97 | 10.00 | 1 | 1 |
| 110 | 24.60 | 33872.30 | 0.85 | | 3.00 | 15 | 1 | 1 |
| 99 | 12.62 | 33774.74 | 0.37 | | 17.97 | 10.00 | 1 | 1 |
| 206 | 9.97 | 26721.77 | 0.94 | | 13.48 | 7.50 | 1 | 1 |
| 25 | 12.72 | 15615.69 | 1.03 | | 3.00 | 8.33 | 1 | 1 |
| 201 | 10.00 | 35257.29 | 0.55 | | 13.48 | 7.50 | 1 | 1 |
| 158 | 23.00 | 79700.11 | 0.71 | | 5.39 | 15.00 | 1 | 1 |
| 197 | 10.64 | 75909.29 | 2.83 | | 13.48 | 7.50 | 1 | 1 |
| 52 | 12.09 | 15664.55 | 0.75 | | 17.97 | 10.00 | 1 | 1 |
| 72 | 12.15 | 41303.58 | 0.68 | | 17.97 | 10.00 | 1 | 1 |
| 124 | 14.65 | 23844.31 | 0.47 | | 12.58 | 12.33 | 1 | 1 |
| 38 | 10.86 | 37552.67 | 0.80 | | 26.96 | 8.33 | 1 | 0 |
| 1 | 14.26 | 130033.54 | 0.03 | | 2.25 | 10.63 | 1 | 1 |
| 208 | 10.49 | 25440.79 | 0.33 | | 13.48 | 7.50 | 1 | 1 |
| 78 | 10.53 | 11963.06 | 0.24 | | 26.96 | 8.33 | 1 | 0 |
| 81 | 10.30 | 23621.25 | 0.58 | | 26.96 | 8.33 | 1 | 0 |
| 186 | 5.20 | 5788.41 | 0.26 | | 2.25 | 2.50 | 0 | 1 |
| 164 | 19.18 | 51948.96 | 1.58 | | 12.58 | 12.33 | 1 | 1 |
| 12 | 21.44 | 227247.72 | 3.26 | | 2.25 | 12.50 | 1 | 1 |
| 200 | 10.73 | 24499.42 | 0.98 | | 26.96 | 7.50 | 1 | 0 |
| 193 | 8.06 | 50554.54 | 0.47 | | 17.97 | 7.50 | 1 | 1 |

TABLE 3-continued

| DoE# | Citric Acid (g/L) | (NH4)2-SO4 (mM) | FeSO4 (mM) | MgSO4 (mM) | CaSO4 (mM) | TM Mix (X) | Yeast Extract (g/L) | Casamino Acid (g/L) | GFP_avg rfu |
|---|---|---|---|---|---|---|---|---|---|
| 204 | 6.34 | 22240.42 | 0.37 | | 13.48 | 5.00 | 1 | | 1 |
| 209 | 10.56 | 11505.95 | 0.51 | | 26.96 | 7.50 | 1 | | 0 |
| 191 | 11.75 | 29382.01 | 1.39 | | 26.96 | 7.50 | 1 | | 0 |
| 192 | 6.61 | 3579.96 | 0.20 | | 13.48 | 3.75 | 0 | | 1 |
| 29 | 11.13 | 39319.75 | 0.41 | | 26.96 | 8.33 | 1 | | 0 |
| 84 | 5.53 | 17849.53 | 1.23 | | 5.99 | 3.33 | 0 | | 1 |
| 40 | 20.44 | 14125.99 | 0.85 | | 8.99 | 15.00 | 1 | | 1 |
| 133 | 14.84 | 55662.10 | 0.22 | | 12.58 | 15.00 | 1 | | 1 |
| 108 | 21.16 | 13186.42 | 0.51 | | 8.99 | 15.00 | 1 | | 1 |
| 58 | 4.55 | 13234.09 | 0.18 | | 5.99 | 3.33 | 0 | | 1 |
| 57 | 4.59 | 12617.80 | 0.36 | | 5.99 | 3.33 | 0 | | 1 |
| 160 | 15.79 | 5770.28 | 1.42 | | 12.58 | 15.00 | 1 | | 1 |
| 82 | 4.21 | 18771.90 | 0.24 | | 5.99 | 3.33 | 0 | | 1 |
| 161 | 20.07 | 108110.14 | 1.91 | | 5.39 | 15.00 | 1 | | 1 |
| 203 | 5.34 | 17747.14 | 0.14 | | 26.96 | 5.00 | 1 | | 0 |
| 174 | 4.12 | 9087.41 | 0.23 | | 8.99 | 2.50 | 0 | | 1 |
| 130 | 20.21 | 13025.17 | 0.39 | | 5.39 | 15.00 | 1 | | 1 |
| 175 | 3.92 | 8666.82 | 0.34 | | 2.25 | 2.50 | 0 | | 1 |
| 156 | 18.11 | 70115.98 | 1.57 | | 12.58 | 15.00 | 1 | | 1 |
| 167 | 17.97 | 54494.21 | 1.32 | | 10.18 | 15.00 | 1 | | 1 |
| 212 | 4.94 | 12843.01 | 0.22 | | 17.97 | 5.00 | 1 | | 1 |
| 169 | 4.71 | 24713.09 | 1.37 | | 8.99 | 2.50 | 0 | | 1 |
| 199 | 4.35 | 22635.66 | 0.21 | | 13.48 | 3.75 | 0 | | 1 |
| 178 | 5.37 | 22782.88 | 2.73 | | 8.99 | 2.50 | 0 | | 1 |
| 50 | 4.92 | 11850.36 | 0.22 | | 53.91 | 6.67 | 1 | | 0 |
| 211 | 4.65 | 19766.06 | 0.32 | | 17.97 | 5.00 | 1 | | 1 |
| 77 | 3.612 | 5939.83 | 0.17 | | 26.96 | 3.33 | 0 | | 0 |
| 202 | 4.13 | 12345.30 | 0.15 | | 26.96 | 3.75 | 0 | | 0 |
| 26 | 3.45 | 6998.54 | 0.22 | | 26.96 | 3.33 | 0 | | 0 |
| 86 | 4.33 | 14648.66 | 0.19 | | 53.91 | 6.67 | 1 | | 0 |
| 137 | 22.84 | 71551.02 | 1.61 | | 5.39 | 15.00 | 1 | | 1 |
| 126 | 22.29 | 97758.45 | 1.08 | | 7.79 | 15.00 | 1 | | 1 |
| 210 | 3.78 | 17224.43 | 0.19 | | 13.48 | 3.75 | 0 | | 1 |
| 51 | 6.36 | 6057.03 | 0.98 | | 53.91 | 16.67 | 0 | | 0 |
| 3 | 4.78 | 11327.77 | 0.35 | | 35.94 | 10.63 | 1 | | 0 |
| 150 | 20.95 | 55369.36 | 1.81 | | 12.58 | 15.00 | 1 | | 1 |
| 148 | 19.85 | 14894.46 | 0.62 | | 5.39 | 15.00 | 1 | | 1 |
| 205 | 3.94 | 13356.59 | 0.23 | | 26.96 | 3.75 | 0 | | 0 |
| 184 | 3.72 | 19346.98 | 0.41 | | 2.25 | 2.50 | 0 | | 1 |
| 105 | 4.24 | 33635.04 | 0.68 | | 26.96 | 8.33 | 1 | | 1 |
| 198 | 3.93 | 13239.50 | 0.31 | | 26.96 | 3.75 | 0 | | 0 |
| 39 | 4.27 | 13883.66 | 0.23 | | 26.96 | 8.33 | 1 | | 0 |
| 27 | 4.36 | 6768.78 | 0.27 | | 26.96 | 8.33 | 1 | | 0 |
| 111 | 14.52 | 33056.05 | 0.80 | | 26.96 | 15.00 | 1 | | 0 |
| 194 | 3.55 | 3577.93 | 0.11 | | 17.97 | 3.75 | 0 | | 1 |
| 207 | 3.34 | 16581.77 | 0.24 | | 26.96 | 3.75 | 0 | | 0 |
| 104 | 4.85 | 11560.40 | 0.11 | | 26.96 | 8.33 | 1 | | 0 |
| 122 | 19.82 | 25049.55 | 0.40 | | 10.18 | 17.67 | 0 | | 1 |
| 65 | 16.26 | 10341.46 | 1.37 | | 5.99 | 16.67 | 0 | | 1 |
| 195 | 2.94 | 12880.05 | 0.02 | | 13.48 | 3.75 | 0 | | 1 |
| 146 | 20.54 | 29975.28 | 0.86 | | 5.39 | 17.67 | 0 | | 1 |
| 2 | 2.61 | 6112.15 | 0.04 | | 35.94 | 3.13 | 0 | | 0 |
| 15 | 3.77 | 16743.58 | 0.23 | | 35.94 | 10.63 | 1 | | 0 |
| 143 | 18.44 | 68003.91 | 1.02 | | 12.58 | 15.00 | 1 | | 1 |
| 114 | 5.76 | 35274.85 | 1.12 | | 53.91 | 16.67 | 0 | | 0 |
| 73 | 2.18 | 26181.92 | 0.10 | | 3.00 | 1.67 | 0 | | 1 |
| 157 | 17.51 | 38635.44 | 1.11 | | 10.18 | 17.67 | 0 | | 1 |
| 32 | 14.58 | 33351.85 | 0.55 | | 26.96 | 15.00 | 1 | | 0 |
| 37 | 2.55 | 3927.56 | 0.08 | | 26.96 | 3.33 | 0 | | 0 |
| 162 | 18.24 | 78067.80 | 0.47 | | 10.18 | 20.33 | 0 | | 1 |
| 190 | 1.99 | 13626.24 | 0.02 | | 4.49 | 1.25 | 0 | | 1 |
| 61 | 2.63 | 3264.37 | 0.10 | | 53.91 | 6.67 | 1 | | 0 |
| 91 | 2.39 | 6434.79 | 0.05 | | 26.96 | 3.33 | 0 | | 0 |
| 33 | 2.15 | 11098.11 | 0.07 | | 3.00 | 1.67 | 0 | | 1 |
| 134 | 19.76 | 72235.45 | 1.73 | | 12.58 | 15.00 | 1 | | 1 |
| 181 | 2.13 | 7210.00 | 0.55 | | 8.99 | 1.25 | 0 | | 1 |
| 34 | 2.05 | 17329.22 | 0.07 | | 3.00 | 1.67 | 0 | | 1 |
| 182 | 1.83 | 17076.19 | 0.16 | | 2.25 | 1.25 | 0 | | 1 |
| 189 | 1.73 | 11866.34 | 0.18 | | 4.49 | 1.25 | 0 | | 1 |
| 75 | 1.86 | 12388.48 | 0.05 | | 3.00 | 1.67 | 0 | | 1 |
| 13 | 1.96 | 9289.76 | 0.12 | | 35.94 | 3.13 | 0 | | 0 |
| 9 | 1.89 | 19387.03 | 0.61 | | 2.25 | 1.25 | 0 | | 1 |
| 159 | 16.50 | 18987.59 | 0.49 | | 12.58 | 17.67 | 0 | | 1 |
| 97 | 2.61 | 7350.27 | 0.11 | | 53.91 | 6.67 | 1 | | 0 |
| 54 | 15.40 | 27379.51 | 0.24 | | 5.99 | 16.67 | 0 | | 1 |
| 31 | 14.49 | 52704.39 | 1.12 | | 26.96 | 15.00 | 1 | | 0 |
| 149 | 13.33 | 125660.79 | 11.56 | | 12.58 | 15.00 | 1 | | 1 |

TABLE 3-continued

| DoE# | Citric Acid (g/L) | (NH4)2-SO4 (mM) | FeSO4 (mM) | MgSO4 (mM) | CaSO4 (mM) | TM Mix (X) | Yeast Extract (g/L) | Casamino Acid (g/L) | GFP_avg rfu |
|---|---|---|---|---|---|---|---|---|---|
| 59 | 17.48 | 11640.64 | 1.01 | | 5.99 | 20.00 | 0 | | 1 |
| 115 | 11.49 | 000500.14 | 10.03 | | 5.99 | 16.67 | 0 | | 1 |
| 170 | 1.10 | 10435.71 | 0.15 | | 2.25 | 0.63 | 0 | | 1 |
| 74 | 1.47 | 4647.62 | 0.17 | | 26.96 | 1.67 | 0 | | 0 |
| 10 | 1.25 | 13118.15 | 0.19 | | 2.25 | 1.25 | 0 | | 1 |
| 136 | 19.75 | 40682.15 | 1.26 | | 1258 | 17.67 | 0 | | 1 |
| 177 | 0.98 | 6389.49 | 0.06 | | 2.25 | 0.63 | 0 | | 1 |
| 43 | 1.37 | 7497.24 | 0.16 | | 26.96 | 1.67 | 0 | | 0 |
| 116 | 17.46 | 76917.27 | 1.96 | | 5.99 | 20.00 | 0 | | 1 |
| 173 | 0.92 | 6036.96 | 0.05 | | 2.25 | 0.63 | 0 | | 1 |
| 76 | 1.44 | 4807.34 | 0.07 | | 8.99 | 1.67 | 0 | | 1 |
| 172 | 1.02 | 4637.28 | 0.06 | | 4.69 | 0.63 | 0 | | 1 |
| 109 | 9.04 | 95625.44 | 7.93 | | 26.96 | 15.00 | 1 | | 0 |
| 180 | 0.84 | 10128.86 | 0.08 | | 8.99 | 0.63 | 0 | | 1 |
| 5 | 13.90 | 23678.57 | 1.43 | | 35.94 | 10.63 | 1 | | 0 |
| 67 | 1.35 | 960.07 | 0.07 | | 53.91 | 3.33 | 0 | | 0 |
| 185 | 0.78 | 7909.85 | 0.15 | | 8.99 | 0.63 | 0 | | 1 |
| 188 | 0.86 | 2322.10 | 0.06 | | 2.25 | 0.63 | 0 | | 1 |
| 113 | 2.58 | 6465.78 | 0.12 | | 53.91 | 16.67 | 0 | | 0 |
| 49 | 19.75 | 2643.63 | 0.82 | | 5.99 | 16.67 | 0 | | 1 |
| 112 | 9.95 | 72305.26 | 8.72 | | 5.99 | 16.67 | 0 | | 1 |
| 70 | 2.13 | 2922.01 | 0.11 | | 17.97 | 3.33 | 0 | | 1 |
| 183 | 0.70 | 1166.42 | 0.04 | | 8.99 | 0.63 | 0 | | 1 |
| 14 | 11.72 | 3126.81 | 0.28 | | 35.94 | 10.63 | 1 | | 0 |
| 85 | 1.90 | 2552.20 | 0.08 | | 17.97 | 3.33 | 0 | | 1 |
| 176 | 0.66 | 5472.63 | 0.07 | | 8.99 | 0.63 | 0 | | 1 |
| 69 | 19.16 | 25913.37 | 1.64 | | 5.99 | 16.67 | 0 | | 1 |
| 19 | 0.76 | 5498.59 | 0.12 | | 35.94 | 1.25 | 0 | | 0 |
| 83 | 0.99 | 2601.33 | 0.08 | | 53.91 | 3.33 | 0 | | 0 |
| 88 | 18.18 | 13893.23 | 2.31 | | 5.99 | 16.67 | 0 | | 1 |
| 63 | 2.66 | 6578.64 | 0.13 | | 53.91 | 16.67 | 0 | | 0 |
| 46 | 1.02 | 1516.09 | 0.06 | | 8.99 | 1.67 | 0 | | 1 |
| 89 | 14.62 | 11532.33 | 0.94 | | 5.99 | 16.67 | 0 | | 1 |
| 127 | 15.38 | 2055.76 | 1.48 | | 12.58 | 23.00 | 0 | | 1 |
| 102 | 12.04 | 3395.76 | 0.52 | | 5.99 | 20.00 | 0 | | 1 |
| 135 | 13.58 | 2243.42 | 1.20 | | 5.39 | 20.33 | 0 | | 1 |
| 20 | 13.98 | 3021.94 | 0.67 | | 2.25 | 20.00 | 0 | | 1 |
| 132 | 15.74 | 374.70 | 0.93 | | 12.58 | 23.00 | 0 | | 1 |
| 165 | 13.77 | 3880.02 | 0.83 | | 7.79 | 23.00 | 0 | | 1 |
| 53 | 8.43 | 495.18 | 1.80 | | 53.91 | 16.67 | 0 | | 0 |
| 16 | 9.17 | 14947.25 | 8.04 | | 8.99 | 20.00 | 0 | | 1 |
| 155 | 11.75 | 80.83 | 0.24 | | 5.39 | 15.00 | 1 | | 1 |
| 128 | 14.25 | 1386.94 | 0.99 | | 12.58 | 23.00 | 0 | | 1 |
| 147 | 11.59 | 399.50 | 0.65 | | 5.39 | 15.00 | 1 | | 1 |
| 163 | 12.59 | 600.44 | 0.23 | | 12.58 | 23.00 | 0 | | 1 |
| 117 | 11.73 | 873.00 | 0.44 | | 17.97 | 30.00 | 0 | | 1 |
| 153 | 15.17 | 3095.57 | 1.20 | | 5.39 | 23.00 | 0 | | 1 |
| 64 | 12.70 | 431.43 | 0.28 | | 17.97 | 30.00 | 0 | | 1 |
| 60 | 12.64 | 600.00 | 0.61 | | 5.99 | 20.00 | 0 | | 1 |
| 119 | 12.65 | 629.60 | 0.61 | | 5.99 | 30.00 | 0 | | 1 |
| 68 | 13.09 | 23.09 | 0.46 | | 5.99 | 30.00 | 0 | | 1 |
| 22 | 0.35 | 1206.70 | 0.02 | | 8.99 | 1.25 | 0 | | 1 |
| 90 | 8.11 | 613.30 | 0.37 | | 53.91 | 16.67 | 0 | | 0 |
| 55 | 6.29 | 391.07 | 0.213 | | 53.91 | 30.00 | 0 | | 0 |
| 62 | 7.49 | 391.07 | 0.04 | | 53.91 | 16.67 | 0 | | 0 |
| 87 | 7.80 | 360.56 | 0.47 | | 53.91 | 16.67 | 0 | | 0 |
| 139 | 14.43 | 732.76 | 0.34 | | 5.39 | 23.00 | 0 | | 1 |
| 120 | 7.63 | 1081.54 | 0.11 | | 53.91 | 30.00 | 0 | | 0 |
| 7 | 11.13 | 657.96 | 0.45 | | 35.94 | 20.00 | 0 | | 0 |
| 56 | 7.25 | 497.59 | 0.31 | | 53.91 | 30.00 | 0 | | 0 |
| 8 | 11.75 | 300.00 | 0.87 | | 35.94 | 20.00 | 0 | | 0 |
| 166 | 9.41 | 9895.88 | 8.29 | | 5.39 | 23.00 | 0 | | 1 |
| 123 | 10.19 | 8438.59 | 8.90 | | 5.39 | 23.00 | 0 | | 1 |
| 118 | 4.87 | 8245.39 | 4.29 | | 53.91 | 30.00 | 0 | | 0 |
| 179 | 0.04 | 552.45 | 0.04 | | 2.25 | 2.50 | 0 | | 1 |
| 187 | 0.06 | 382.80 | 0.06 | | 8.99 | 2.50 | 0 | | 1 |
| 171 | 0.02 | 408.57 | 0.05 | | 4.49 | 2.50 | 0 | | 1 |

Comparison with Current Approaches.

Figure 7:
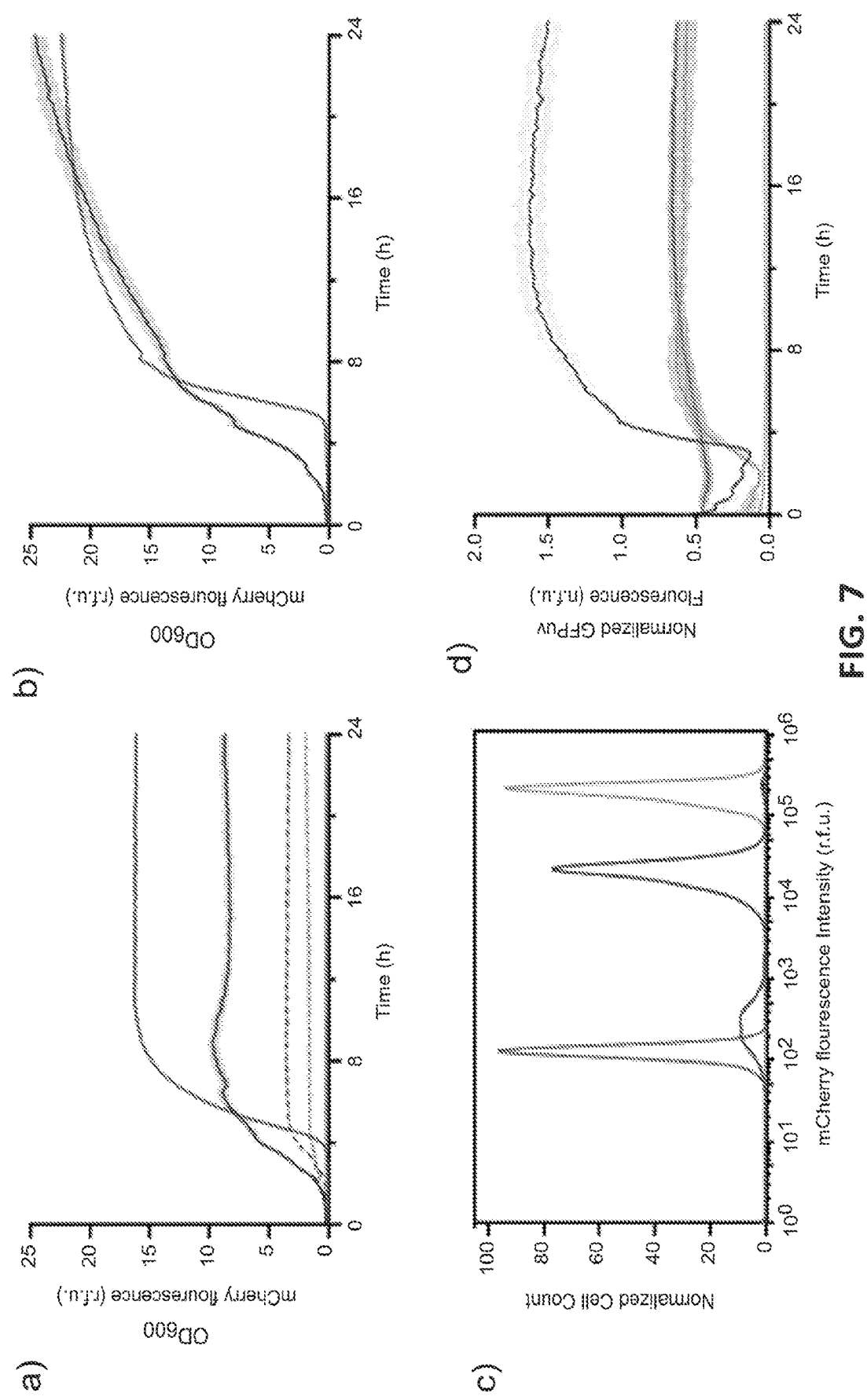
FIG. 7A-D are graphs showing head to head comparison of autoinduction via phosphate depletion with pET-based expression in BL21(DE3) in accordance with one aspect of the present disclosure.

With the successful development of an optimal autoinduction broth, we turned to a head to head comparison of this approach with the traditional protocols based in LB media as well as the lactose based autoinduction system as developed by Studier. Due to the availability of a pET-mCherry plasmid (Table 1) mCherry was used as the reporter for this comparison. Specifically, induction of mCherry in BL21 (DE3) with pLysS and pETM6-mCherry, using either IPTG based induction in LB media, or lactose autoinduction media was compared to strain DLF_R002 with plasmid pHCKan-yibDp-mCherry in AB. To monitor not only endpoint expression but the dynamics of growth and auto-induction, these studies were performed in the Biolector™. Results are shown in FIGS. 6 and 7. Referring first to FIG. 6, Standard expression results using BL21(DE3), LB media with IPTG based induction. mCherry total fluorescence (colored lines, red induced, blue uninduced) and OD600 (black lines, solid induced, dashed uninduced) are plotted overtime. IPTG was added at inoculation. LEFT: BL21(DE3) grown in LB media with IPTG based induction. RIGHT: BL21(DE3) with pLys grown in LB media with IPTG based induction.

Referring now to FIG. 7: a head to head comparison of autoinduction via phosphate depletion with pET based expression in BL21(DE3). a) pET based mCherry expression in BL21(DE3) with pLysS. mCherry (red lines) and biomass levels (OD600 nm, black lines) over time. Solid lines-lactose based autoinduction. Dashed lines-IPTG induction in LB media. b) yibDp based mCherry expression in DLF_R002 in AB media mCherry (red lines) and biomass levels (OD600 nm, black lines). c) Cytometry of induced populations (gray-empty vector control, red-pET-mCherry in BL21(DE3)+pLysS, green–yibDp-mCherry in DLF_R002). d) expression of the Lon substrate (GFP-$\beta$20-cp6) in BL21(DE3) and DLF_R002. Normalized fluorescence is relative fluorescence normalized to optical density. Black line-GFP control (non Lon substrate) in DLF_R002. Red line—BL21(DE3) expressing GFP-$\beta$20-cp6. Green line—DLF_R002 expressing GFP-$\beta$20-cp6. Shaded areas are standard deviations of at least three replicates.

As expected, using *E. coli* BL21(DE3) and pET based expression, lactose based autoinduction media enabled higher cell densities and higher expression levels of mCherry than induction with IPTG (FIG. 7A). Phosphate based autoinduction using strain DLF_R002 enabled a further 40% increase in final mCherry levels at 24 hrs over BL21(DE3) (FIG. 7B). Cytometry was used to further characterize these two expression systems (FIG. 7C). Phosphate based autoinduction not only had more homogeneous induction but also more expression per cell. Additionally, one of the major potential reported advantages of BL21 (DE3) and related strains is reduction in Lon protease activity. To investigate the impact of Lon activity in these strains, a previously reported fluorescent Lon substrate was used to monitor the impact of this protease. Specifically, a circular permutation variant of GFP with a Lon degradation tag (GFP-$\beta$20-cp6) was used. Results are given in FIG. 7D. The expression level of the Lon substrate was significantly reduced compared to a non-Lon substrate for both strains, but at least with this specific reporter, no significant difference in cell specific Lon activity was observed between BL21(DE3) and DLF_R002.

Optimization of High Throughput Expression Protocols

Figure 8:
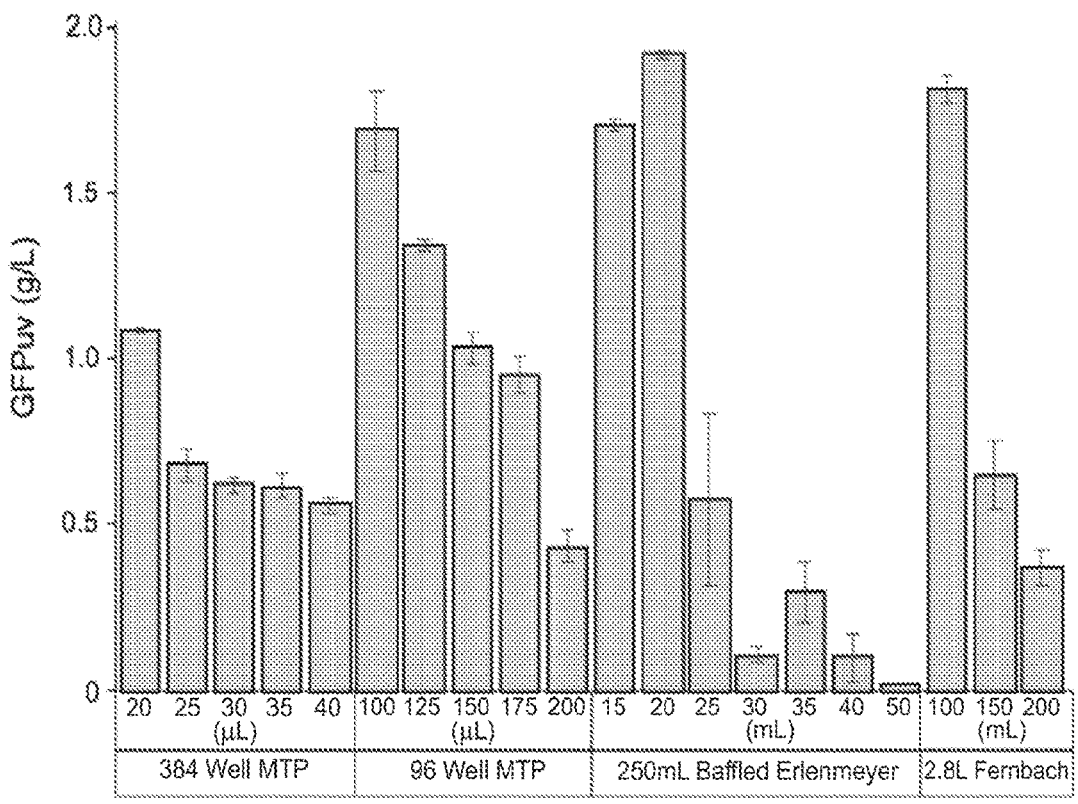
FIG. 8 is a graph showing the optimization of autoinduction in batch cultures at various scales in accordance with one aspect of the present disclosure.

The results discussed above were generated in 96 well plates using high shaking speeds in combination with the Duetz system, which utilizes a series of specialty plate covers to minimize evaporative volume loss, while enabling adequate aeration. As rapid growth and expression are not only a function of media, but culture aeration, we sought to evaluate the optimal aeration conditions for microtiter plate based expression (96 and 384 well plates). In addition to orbital shaking speed and orbit diameter, culture volume (impacting the surface area to volume ratio) can have a significant impact on oxygen transfer and in this case protein expression as shown in FIG. 8: Optimization of autoinduction in batch cultures at various scales. Impact of various fill volumes on expression in AB. Varying fill volumes in 384 and 96 well plates as well as 250 mL baffled Erlenmeyer and 2.8 L Fernbach flasks. When using 384 well plates, 0.05% polypropylene glycol (2000 MW) was added to the media. DLF_R002 with plasmid pHCKan-yibDp-GFPuv was used for all experiments.

Figure 9:
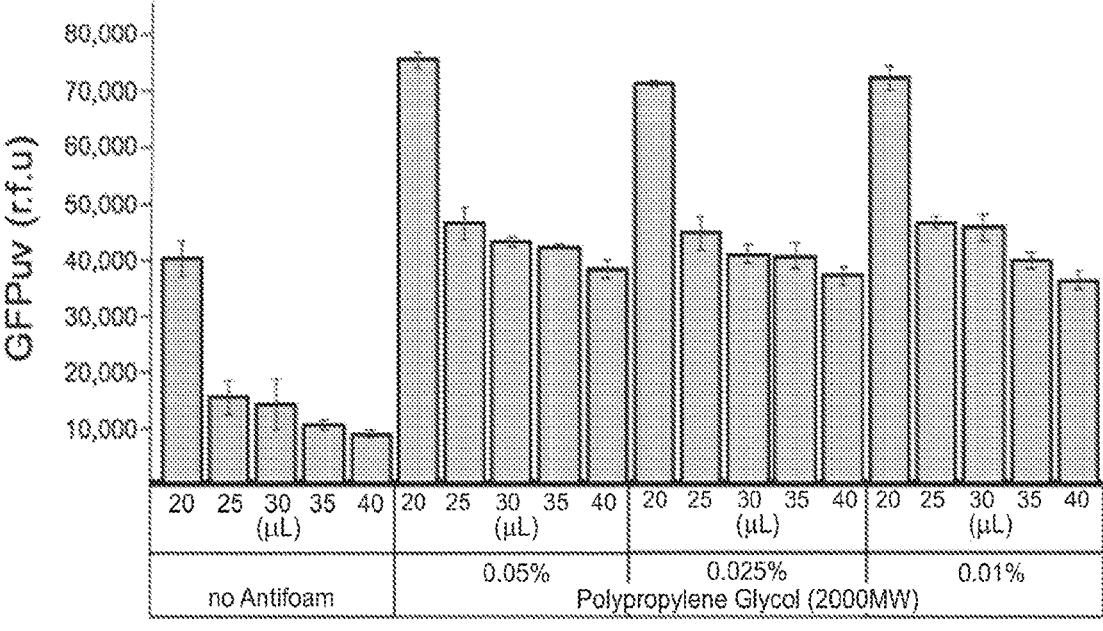
FIG. 9 is a graph showing the impact of surfactants on expression in 384 well plates in accordance with one aspect of the present disclosure.
Figure 10:
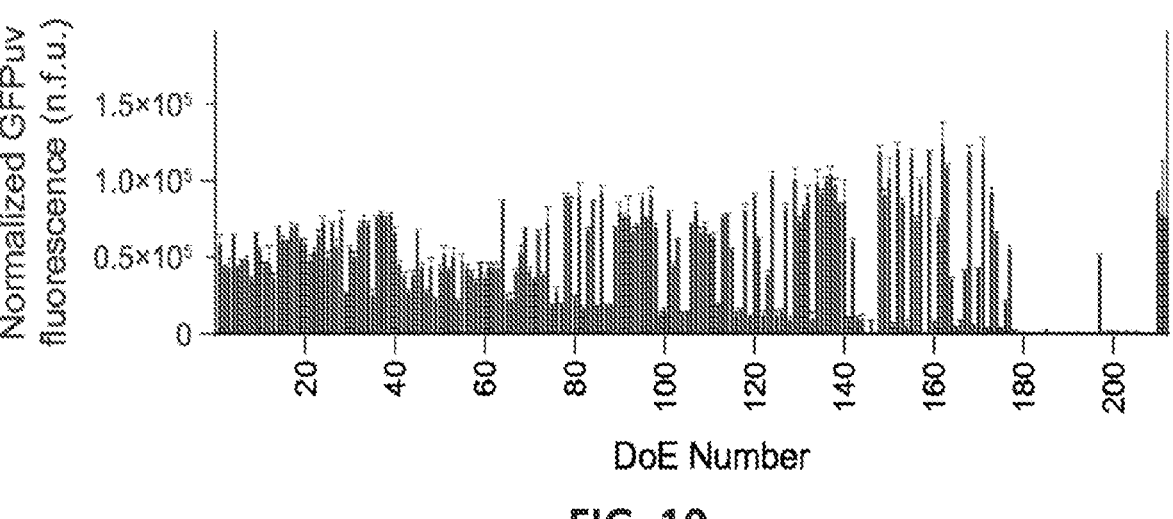
FIG. 10 is a graph showing normalized GFP/OD600 nm for DoE studies. Normalized fluorescence units (n.f.u) for each media formulation is given, which is the relative fluorescence (r.f.u) divided by the optical density at 600 nm in accordance with one aspect of the present disclosure.
Figure 11:
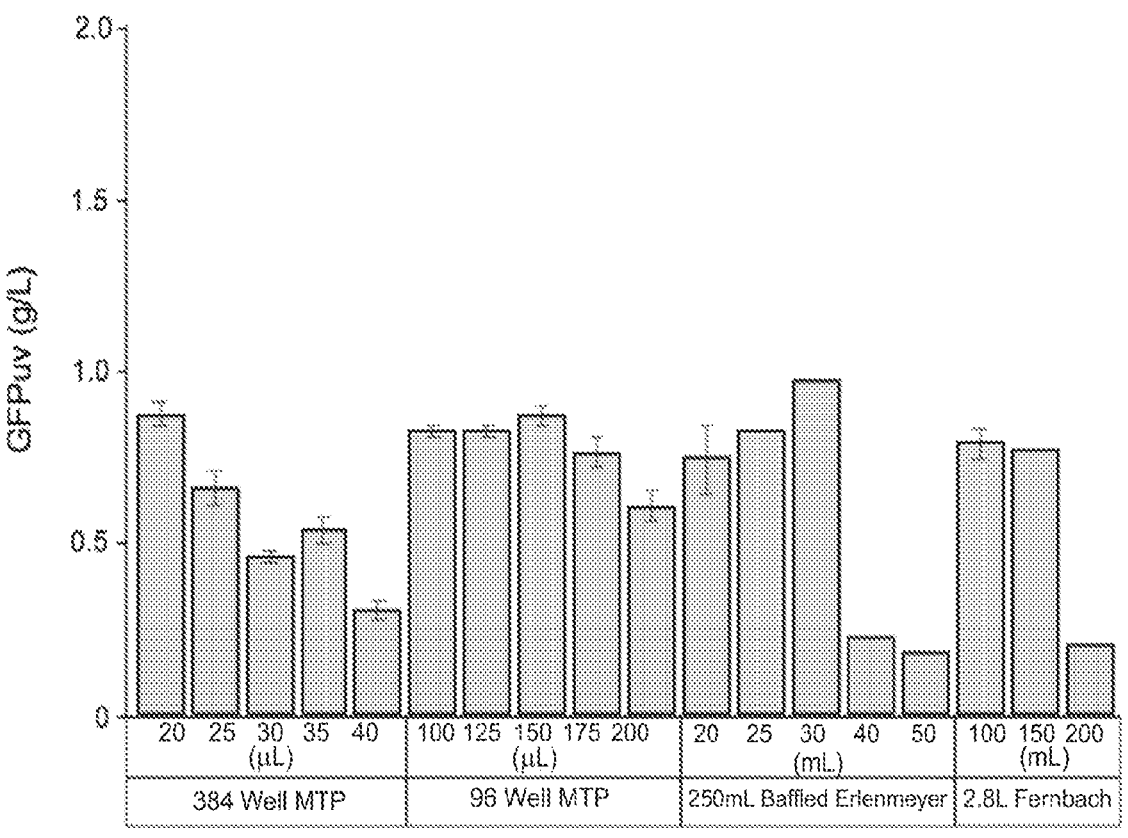
FIG. 11 is a graph showing the autoinduction in batch cultures at various scales using AB-C7 media with lower supported biomass levels (~3 gCDW/L) in accordance with one aspect of the present disclosure.

In standard 96 well plates, volumes less than 100 $\mu$L gave optimal expression. As 384 well plates have a very small area, the surface tension at the culture meniscus can limit mixing. As a result, small amounts of surfactant (commercial antifoam) were added to improve aeration in 384 well plates, FIG. 9. FIG. 9 demonstrates the impact of surfactants on expression in 384 well plates. Relative GFPuv levels in AB as a function of filling volume and antifoam concentration. Polypropylene glycol (MW of 2000) was used. % are in volume (v/v %). DLF_R002 with plasmid pHCKan-yibDp-GFPuv was used for all experiments. In 384 well cultures volumes less than 20 $\mu$L gave optimal expression with AB media. As can be seen in FIG. 8, expression levels, using AB in 384 well plates, did not reach levels observed in the 96 well plates or other culture systems. We hypothesized this was due to remaining mass transfer limitations. We tested this hypothesis by evaluating an autoinduction media identified in the DoE results (AB-C7) that yielded reduced biomass and expression levels, but as a result would have a lower maximal aeration requirement. With lowered biomass levels, and aeration demands, expression levels in 384 well plates reached that of other culture systems using this media (FIGS. 10 and 11). Although total protein levels are higher in AB media, the use of AB-C7 media may be preferred when using 384 well plates in order to minimize oxygen limitations.

Referring now to FIG. 10, Normalized GFP/OD$_{600\ nm}$ for DoE studies are demonstrated. Normalized fluorescence units (n.f.u) for each media formulation is given, which is the relative fluorescence (r.f.u) divided by the optical density at 600 nm. The data order is the same rank order as in FIG. 3 in the main text. Media AB-C7 is highlighted in red, and reaches final optical densities from 7-10, or ~3 gCDW/L.I DLF_R002 with plasmid pHCKan-yibDp-GFPuv was used for all experiments. In FIG. 11, autoinduction in batch cultures at various scales using AB-C7 media with lower supported biomass levels (~3 gCDW/L) is demonstrated. Varying fill volumes in 384 and 96 well plates as well as 250 mL baffled Erlenmeyer and 2.8 L Fernbach flasks. When using 384 well plates, 0.042% polypropylene glycol (2000 MW) was added to the media. DLF_R002 with plasmid pHCKan-yibDp-GFPuv was used for all experiments. Where error bars are present, data are averages of at least triplicate experiments, when absent data are from single studies.

Development of Shake Flask Protocols

For any expression protocol to be widely applicable, it cannot rely on controlled bioreactors and/or specialty plate systems, but be accessible to the average laboratory. Toward this goal, we turned to the optimization of the protocol in shake flask cultures. As mentioned above, one primary difference between bioreactor experiments and shake flask cultivation is oxygen transfer. While instrumented bioreactors and micro-reactors such as the Biolector™ can easily meet these mass transfer targets, standard shake flask have reported oxygen transfer rates anywhere from 20 mmoles/ L-hr (for unbaffled flasks) to 120 mmoles/L-hr for baffled glassware. A key potential consequence of shake flasks is oxygen limitation and reduced growth rates and expression. As a consequence we sought to evaluate the optimal culture conditions to achieve maximal expression in shake flask cultures with a focus on baffled 250 mL Erlenmeyer flasks and 2.8 L Fernbach flasks. As seen in FIG. 5, again culture volume plays a key role in optimal protein expression, with 20 mL or lower being optimal in baffled 250 mL Erlenmeyer flasks and 100 mL or lower being optimal in 2.8 L Fernbach flasks. These results were obtained in shakers where an adhesive mat is used to hold flasks and shaking speeds are limited to 150 rpm. Using clamps, higher shaking speeds may enable optimal expression using larger shake flask fill volumes.

Utility with a Diverse Group of Recombinant Proteins

Figure 12:
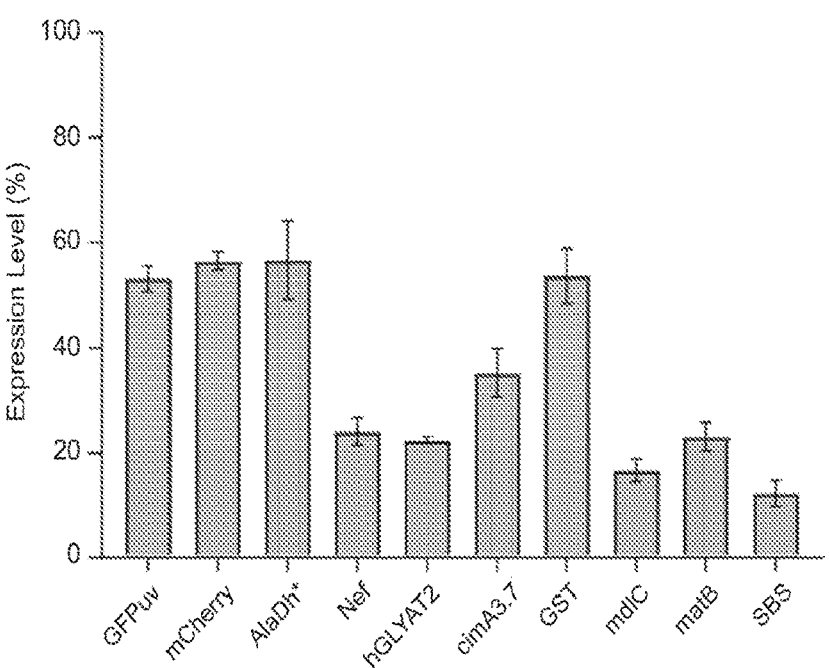
FIG. 12 is a graph showing the autoinduction in AB in 96 well plates for a diverse set of recombinant proteins including: GFPuv, mCherry, AlaDh* (a mutant alanine dehydrogenase), Nef (HIV-1 Nef protein), hGLYAT2 (human glycine acyltransferase-2 an N-terminal chitin binding tag), cimA3.7 (a mutant citramalate synthase), GST, mdlC (benzylformate decarboxylase), matB (malonyl-CoA synthetase), and SBS (bornyl-diphosphate synthase with a C-terminal mCherry tag) in accordance with one aspect of the present disclosure.
Figure 13:
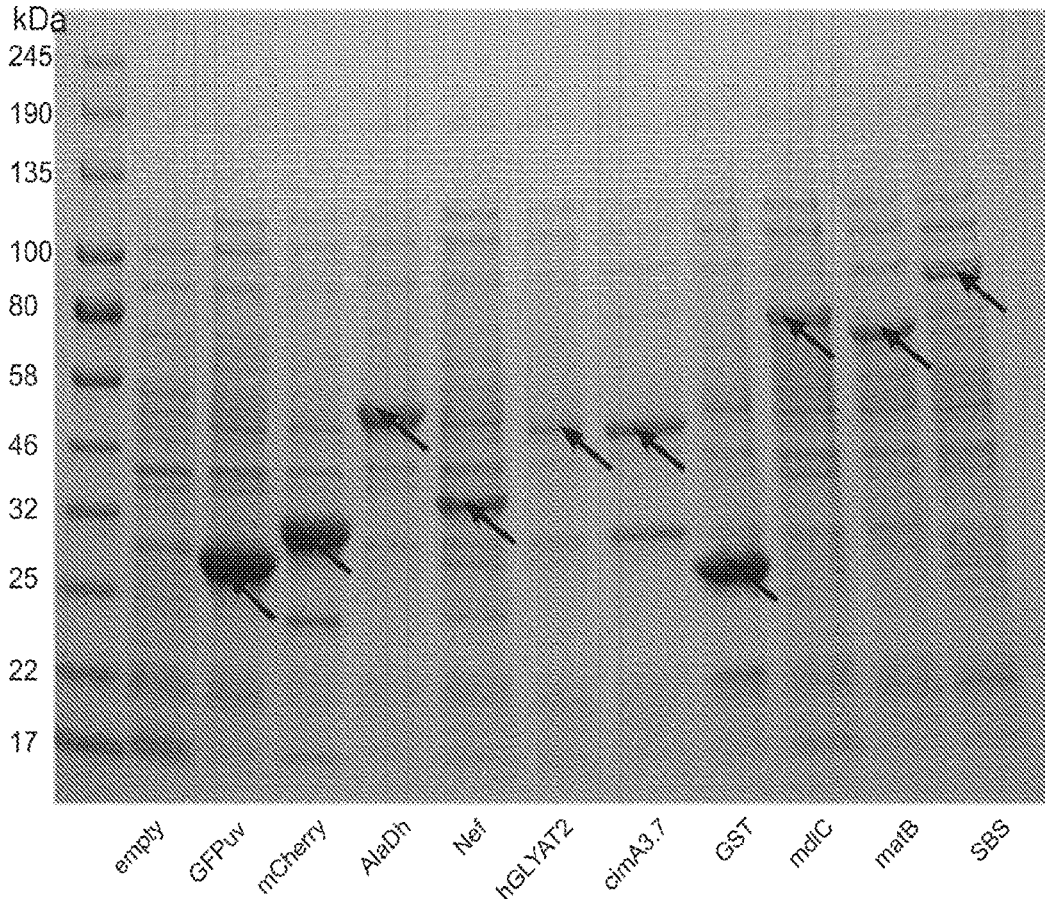
FIG. 13 is an SDS-PAGE showing results for a diverse set of proteins. Samples taken after autoinduction in AB media using strain DLF_R002 and the appropriate plasmid from Table 1 in accordance with one aspect of the present disclosure.

All results discussed to this point relied on easily quantified reporter proteins (GFPuv and mCherry), which are easily expressed to high levels in most expression hosts. In order to evaluate the broader applicability of the approach, the expression of a group of other diverse proteins was evaluated in several vector backbone contexts in the phosphate autoinduction protocol. These included: a borneol diphosphate synthase, a terpene synthase with a C-terminal mCherry tag, a mutant alanine dehydrogenase, a malonyl-CoA synthetase, a benzoylformate decarboxylase, glutathione S-transferase, HIV-1 nef protein, a mutant citramalate synthase, and a human glycine acyltransferase with an N-terminal chitin binding tag (Refer to Table 1). As can be seen in FIGS. 12 and 13, expression levels ranged from ~10% of total protein for a large terpene synthase to 55% in the case of alanine dehydrogenase, achieving maximal protein concentrations of 275 mg/gCDW in the best case.

In FIG. 12, autoinduction in AB in 96 well plates for a diverse set of recombinant proteins including: GFPuv, mCherry, AlaDh* (a mutant alanine dehydrogenase), Nef (HIV-1 Nef protein), hGLYAT2 (human glycine acyltransferase-2 an N-terminal chitin binding tag), cimA3.7 (a mutant citramalate synthase), GST, mdlC (benzylformate decarboxylase), matB (malonyl-CoA synthetase), and SBS (bornyl-diphosphate synthase with a C-terminal mCherry tag). Percent of total expression is given for three replicates. FIG. 13 is an example SDS-PAGE result. In particular, SDS PAGE Results for a diverse set of proteins. Samples taken after autoinduction in AB media using strain DLF_R002 and the appropriate plasmid from Table 1. Expression was performed in 96 well plates. Expression levels range from 10% in the case of SBS (a terpene synthase) to 55% in the case of GFPuv, mCherry, alanine dehydrogenase (AlaDh) and GST.

Two-stage expression induced upon phosphate depletion enables a facile and versatile approach to routine high level recombinant protein production. In the case of GFPuv, protein titers approaching 2 g/L in batch microtiter plates and shake flasks. These titers correspond to protein yields of 20 μg of protein per well in 384 well plates, 170 μg per well in 96 well plates, and 40 mg and 180 mg of protein in 250 mL Erlenmeyer and Fernbach flasks, respectively. Importantly, current results also support homogenous expression using phosphate depletion. Expression levels will of course vary as a function of the protein and expression construct, but initial testing with additional proteins supports expression levels from 10 to 63 percent of total cellular protein, which at the high end is ~275 mg/gCDW of recombinant protein and represents significant improvements in heterologous protein expression in E. coli. More work is needed to better understand the mechanisms unexpectedly high expression levels observed in this system. Initial adaptation to instrumented bioreactors, enabled GFP titers as high as 2.7 g/L, 270 mg/gCDW and 55% expression. Further optimization of bioreactor protocols may enable much higher cell density cultures. If truly high cell density fermentations (from 50-100 gCDW/L of biomass) can be developed with equivalent expression levels, protein titers in the range of 15-30 g/L or higher in some cases can be expected.

In the existing protocol, firstly, proteins of interest must be cloned into a plasmid with the yibDp promoter. Screening of additional phosphate (phoB) regulated promoters may yield improved or varied expression. Adaptation of the system for use with existing pET based plasmids would also be of utility for proteins that are already cloned into these standard vectors. Secondly, preparation of AB media is more complicated than making routine LB media.

Despite these important criteria, the development of strains, plasmids and protocols for autoinduction based on phosphate depletion not only enables improved expression, with impressive protein titers, but also a scalable methodology. A single host and plasmid can be used in high throughput screening of initial expression constructs or mutant variants all the way through to instrumented bioreactors. These results support the biosynthetic potential of phosphate depleted stationary phase cultures of E. coli. Decoupling growth from production also has the potential to enable future studies focused on key remaining limitations in protein biosynthesis in this well characterized host.

Materials & Methods

Microorganisms

Features as described and claimed herein may be provided in a microorganism selected from the listing herein, or another suitable microorganism, that also comprises one or more natural, introduced, or enhanced product bio-production pathways. Thus, in some aspects the microorganism(s) comprise an endogenous product production pathway (which may, in some such aspects, be enhanced), whereas in other aspects the microorganism does not comprise an endogenous product production pathway.

More particularly, based on the various criteria described herein, suitable microbial hosts for the bio-production of a chemical product generally may include, but are not limited to the organisms described herein.

The host microorganism or the source microorganism for any gene or protein described here may be selected from the following list of microorganisms: Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces, and Pseudomonas. In some aspects the host microorganism is an E. coli microorganism.

Genetic Modifications, Nucleotide Sequences, and Amino Acid Sequences

Aspects of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host.

Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various aspects of the invention the genetic manipulations may include a manipulation directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected culture conditions. Genetic manipulation of nucleic acid sequences may increase copy number and/or comprise use of mutants of an enzyme related to product production. Specific methodologies and approaches to achieve such genetic modification are well known to one skilled in the art.

In various aspects, to function more efficiently, a microorganism may comprise one or more synthetic metabolic valves, composed of enzymes targeted for controlled proteolysis, expression silencing or a combination of both controlled proteolysis and expression silencing. For all nucleic acid and amino acid sequences provided herein, it is appreciated that conservatively modified variants of these sequences are included, and are within the scope of the invention in its various aspects. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various aspects of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

Reagents and Media: Unless otherwise stated, all materials and reagents were of the highest grade possible and purchased from Sigma (St. Louis, MO). Luria Broth, lennox formulation with lower salt was used for routine strain and plasmid propagation and construction and is referred to as LB below. All media formulations including stock solutions are described in the following Media Formulations section. Working antibiotic concentrations were as follows: kanamycin (35 µg/mL), chloramphenicol (35 µg/mL), ampicillin (100 µg/mL), tetracycline (5 µg/mL), apramycin (100 µg/mL). Polypropylene glycol (MW of 2000) and casamino acids were obtained from VWR international (Suwanee, GA), product numbers E278-500G and 90001-740, respectively. Yeast extract and MOPS (3-(N-morpholino)propanesulfonic acid) were obtained from Biobasic (Amherst, NY), product numbers G0961 and MB0360, respectively.

Media Stock Solutions: 10× concentrated Ammonium-Citrate 30 salts (1 L) by mixing 30 g of (NH4)2SO4 and 1.5 g Citric Acid in water with stirring, adjust pH to 7.5 with NaOH. Autoclave and store at room temperature (RT). 10× concentrated Ammonium-Citrate 90 salts (1 L) by mixing 90 g of (NH4)2SO4 and 2.5 g Citric Acid in water with stirring, adjust pH to 7.5 with NaOH. Autoclave and store at RT. 3 M Ammonium sulfate solution in water. Autoclave and store at RT. 100 g/L citric acid in water. Autoclave and store at RT. 1 M Potassium 3-(N-morpholino) propanesulfonic Acid (MOPS), adjust to pH 7.4 with KOH. Filter sterilize (0.2 µm) and store at RT. 0.5 M potassium phosphate buffer, pH 6.8 by mixing 248.5 mL of 1.0 M K2HPO4 and 251.5 mL of 1.0 M KH2PO4 and adjust to a final volume of 1000 mL with ultrapure water. Filter sterilize (0.2 µm) and store at RT. 2 M MgSO4 and 10 mM CaSO4 solutions. Filter sterilize (0.2 µm) and store at RT. 50 g/L solution of thiamine-HCl. Filter sterilize (0.2 µm) and store at 4° C. 500 g/L solution of glucose, dissolving by stirring with mild heat. Cool, filter sterilize (0.2 µm), and store at RT. 100 g/L yeast extract, autoclave, and store at RT. 100 g/L casamino acid, autoclave, and store at RT. 500× Trace Metal Stock: Prepare a solution of micronutrients in 1000 mL of water containing 10 mL of concentrated H2SO4, 0.6 g CoSO4·7H2O, 5.0 g CuSO4·5H2O, 0.6 g ZnSO4·7H2O, 0.2 g Na2MoO4·2H2O, 0.1 g H3BO3, and 0.3 g MnSO4·H2O. Filter sterilize (0.2 µm) and store at RT in the dark. Prepare a fresh solution of 40 mM ferric sulfate heptahydrate in water, filter sterilize (0.2 µm) before preparing media each time.

Media Formulations: Prepare the final working medium by aseptically mixing stock solutions based on Tables 4 and 5 in the order written to minimize precipitation, then filter sterilize (with a 0.2 µm filter).

TABLE 4

| Ingredient | Concentration Stock | | Volume in 1 L (mL) | Final Concentration | |
|---|---|---|---|---|---|
| Media Formulations | | | | | |
| SM10+ Seed Media, pH 6.8: | | | | | |
| Ammonium-Citrate 90 Salts, pH 7.5 | 10 | X | 100.0 | 1 | X |
| Phosphate Buffer, pH 6.8 | 500 | mM | 10.0 | 5.00 | mM |
| Trace Metals | 500 | X | 4.0 | 2 | X |
| Fe (II) Sulfate | 40 | mM | 4.0 | 0.16 | mM |
| MgSO$_4$ | 2 | M | 1.25 | 2.50 | mM |
| CaSO$_4$ | 10 | mM | 6.25 | 0.0625 | mM |
| Glucose | 500 | g/L | 90.0 | 45.0 | g/L |
| MOPS | 1 | M | 200.0 | 200 | mM |
| Thiamine-HCl | 50 | g/L | 0.2 | 0.01 | g/L |
| Yeast Extract | 100 | g/L | 10.0 | 1.0 | g/L |
| Casamino Acids | 100 | g/L | 0 | 0 | |
| FGM10 Media, pH 6.8: | | | | | |
| Ammonium-Citrate 90 Salts, pH 7.5 | 10 | X | 100.0 | 1 | X |
| Phosphate Buffer, pH 6.8 | 500 | mM | 10.0 | 5.00 | mM |
| Trace Metals | 500 | X | 4.0 | 2 | X |
| Fe (II) Sulfate | 40 | mM | 4.0 | 0.16 | mM |
| MgSO$_4$ | 2 | M | 1.25 | 2.50 | mM |
| CaSO$_4$ | 10 | mM | 6.25 | 0.06 | mM |
| Glucose | 500 | g/L | 50.0 | 25.0 | g/L |
| Thiamine-HCl | 50 | g/L | 0.2 | 0.01 | g/L |
| Yeast Extract | 100 | g/L | 0 | 0 | |
| Casamino Acids | 100 | g/L | 0 | 0 | |
| AB Autoinduction Broth (aka Awesome Broth): | | | | | |
| Ammonium sulfate | 3 | M | 13.6 | 40.8 | mM |
| Citric acid | 100 | g/L | 2.5 | 0.25 | g/L |
| Trace Metals | 500 | X | 5.6 | 2.8 | X |
| Fe (II) Sulfate | 40 | mM | 2.4 | 0.096 | mM |
| MgSO$_4$ | 2 | M | 4.35 | 8.7 | mM |
| CaSO$_4$ | 10 | mM | 7.08 | 0.0708 | mM |
| Glucose | 500 | g/L | 90.0 | 45.0 | g/L |
| MOPS | 1 | M | 200.0 | 200 | mM |
| Thiamine-HCl | 50 | g/L | 0.2 | 0.01 | g/L |
| Yeast Extract | 100 | g/L | 62 | 6.2 | g/L |
| Casamino Acids | 100 | g/L | 35 | 3.5 | g/L |
| Autoinduction C7 Media | | | | | |
| Ammonium sulfate | 3 | M | 22.67 | 68 | mM |
| Citric acid | 100 | g/L | 2.5 | 0.25 | g/L |
| Trace Metals | 500 | X | 4 | 2 | X |
| Fe (II) Sulfate | 40 | mM | 4 | 0.160 | mM |
| MgSO$_4$ | 2 | M | 5 | 10 | mM |
| CaSO$_4$ | 10 | mM | 6.25 | 0.0625 | mM |
| Glucose | 500 | g/L | 90.0 | 45.0 | g/L |
| MOPS | 1 | M | 200.0 | 200 | mM |
| Thiamine-HCl | 50 | g/L | 0.2 | 0.01 | g/L |
| Yeast Extract | 100 | g/L | 25 | 2.5 | g/L |
| Casamino Acids | 100 | g/L | 25 | 2.5 | g/L |

TABLE 5

| | Nutrient Levels used in the media DoE experiment: | | | | | | | |
| Levels | Citric Acid (g/L) | (NH₄)₂SO₄ (mM) | FeSO₄ (mM) | MgSO₄ (mM) | CaSO₄ (mM) | TM Mix (X) | Yeast Extract (g/L) | Casamino Acid (g/L) |
|---|---|---|---|---|---|---|---|---|
| 1 | 0.0625 | 17 | 0.040 | 2.5 | 0.016 | 0.5 | 0.625 | 0 |
| 2 | 0.08 | 22.67 | 0.053 | 3.33 | 0.021 | 0.67 | 0.83 | 0.625 |
| 3 | 0.125 | 34 | 0.080 | 5 | 0.031 | 1 | 1.25 | 0.83 |
| 4 | 0.17 | 40.8 | 0.096 | 6.0 | 0.038 | 1.2 | 1.67 | 1.67 |
| 5 | 0.25 | 45.33 | 0.107 | 6.67 | 0.042 | 1.33 | 2.5 | 2.5 |
| 6 | 0.375 | 58.9 | 0.139 | 8.7 | 0.054 | 1.7 | 3.5 | 3.5 |
| 7 | 0.500 | 68 | 0.160 | 10 | 0.063 | 2 | 3.75 | 5.00 |
| 8 | 0.75 | 77.1 | 0.18 | 11.3 | 0.071 | 2.3 | 5.00 | 6.2 |
| 9 | 1 | 95.2 | 0.22 | 14.0 | 0.088 | 2.8 | 6.2 | 7.50 |
| 10 | 1.50 | 102 | 0.24 | 15 | 0.094 | 3 | 7.50 | 8.8 |
| 11 | | 136.00 | 0.32 | 20.00 | 0.125 | 4.00 | 8.8 | 10 |
| 12 | | 204.00 | 0.48 | 30.00 | 0.188 | 6.00 | 10 | 11.5 |
| 13 | | 272 | 0.64 | 40 | 0.250 | 8 | 11.5 | 15.00 |
| 14 | | 408.00 | 0.96 | 60.00 | 0.375 | 12.00 | 15.00 | |

Strains and Strain Construction: *E. coli* strains BL21 (DE3) (Catalogue #C2527) and BL21(DE3) pLysS (Catalogue #C3010) were obtained from New England BioLabs, Ipswich, MA. Strain BW25113 was obtained from the Yale *E. coli* Genetic Stock Center (cgs c.biology.yale.edu). Strain BWapldf was a gift from George Chen (Tsinghua University). Chromosomal modifications were made using standard recombineering methodologies through scarless tet-sacB selection and counters election, strictly following the protocols of Li et al. The recombineering plasmid pSIM5 and the tet-sacB selection/counterselection marker cassette were kind gifts from Donald Court (NCI, redrecombineering.ncifcrf.gov/court-lab.html). Briefly, the tet-sacB selection/counterselection cassette was amplified using the appropriate oligos supplying ~50 bp flanking homology sequences using Econotaq (Lucigen Middleton, WI) according to manufacturer's instructions, with an initial 10 minutes denaturation at 94° C., followed by 35 cycles of 94° C., for 15 seconds, 52° C. for 15 seconds, and 72° C. for 5 minutes. Cassettes used for "curing" of the tet-sacB cassette were obtained as gBlocks from (Integrated DNA Technologies, Coralville, Iowa, USA). The ompT protease gene was deleted using standard recombineering methods by selection for an apramycin selectable marker obtained from the pMDIA plasmid. pMDIAI was a gift from Sheng Yang (Addgene plasmid #51655; n2t.net/addgene:51655; RRID: Addgene_51655). Primers and DNA sequences are given in Table 6. Chromosomal modifications were confirmed by PCR amplification and sequencing (Genewiz, NC) using paired oligonucleotides, either flanking the entire region.

Plasmids: pETM6, and pETM6-mCherry was a gift from Mattheos Koffas (Addgene plasmids ##49795 and #66534). pLysS was obtained from New England Biolabs (NEB, Ipswich, MA). Plasmids made in this study were constructed using G-blocks™ and/or PCR products and assembled using NEBuilder® HiFi DNA Assembly Master Mix following manufacturer's protocol (NEB, Ipswich, MA). Polymerase chain reactions were performed with Q5 DNA Polymerase (NEB, Ipswich, MA). pSMART-HC-Kan (Lucigen, WI), pTWIST-Chlor-Medium Copy (Twist Biosciences San Francisco, CA), pTWIST-Kan-High Copy (Twist Biosciences San Francisco, CA) and pCDF (derived from pCDF-1b, EMD Millipore, Burlington, MA) were used as a backbone vectors in these studies. Sequences of all oligos and synthetic DNA are given in Table 6. All plasmid sequences were confirmed by DNA sequencing (Genewiz, NC). Sequences and maps are available with Addgene. Refer to Table 1 for Addgene numbers. pCDF was constructed from pCDF-1b by first amplifying the vector with primers pCDF-1b-ampl1 and pCDF-1b-ampl2, to remove the lacI gene, followed by DNA assembly with pCDF-MCS. All genes were codon optimized for expression in *E. coli* using IDT's codon optimization tool (www.idtdna.com/CodonOpt). pHCKan-yibDp-GFPuv, pHCKan-yibDp-mCherry, pSMART-Ala1, pHCKan-yibDp-GFP and pHCKan-yibDp-GST were constructed by DNA assembly with linearized pSMART-HC-Kan obtained from lucigen with yibDp-GFPuv, yibDp-mCherry, yibDp-ald*, yibDp-GFP, yibDp-GST and yibDp-GFP-β20cp6 G-blocks™ respectively. pCDF-yibDp-matB was obtained by DNA assembly of a G-block™ (yibDp-matB) with pCDF-ev which was amplified by PCR with SR2_rc and SL1_rc. pCDF-yibDp-mdlC-his was constructed from the assembly of 2 synthetic G-blocks™ yibDp-mdlC-his1 and yibDp-mdlC-his2. pTCmc-yibDp-SBS-mCherry, pTKhcan-yibDp-cimA3.7, pHCKan-yibDp-GFP6β2ncp6 and pHCKan-yibDp-Nef were constructed at TWIST Biosciences (San Francisco, CA) using the pTWIST-Chlor-Medium-Copy, pSMART-HC-Kan, pSMART-HC-Kan and pTWIST-Kan-High-Copy vectors respectively. pHCKan-yibDp-GFP-cp6 was constructed by Q5 mutagenesis or "Around the World" PCR of plasmid pHCKan-yibDp-GFP-β320cp6, to remove the Lon degron tag, with primers GFP_cp6_F and GFP_cp6_R followed by DpnI treatment phosphorylation and self ligation, using KLD reaction mix obtained from NEB. (Ipswich, MA). pHCKan-yibDp-CBD-hGLY was constructed by DNA assembly with 2 PCR products amplified from (i) a plasmid coding hGLY under a T7 promoter (pHCKan-T7-CBD-hGLY, Addgene #134940, constructed at TWIST Biosciences) using primers pS-yibD-hGLY_F and pS-yibD-hGLY_R; and (ii) a plasmid containing the yibDp promoter, (pHCKan-yibDp-ald*-alaE, Addgene #134939) using primers pS-yibDp-FOR and pS-yibDp-REV).

TABLE 6

| Name | Sequence |
|---|---|
| | Table 6: Synthetic DNA and Oligos used for strain construction |
| tet-sacB Cassette | TCCTAATTTTTGTTGACACTCTATCATTGATAGAGTTATTTTACCACTCCCTATCAGTGATA GAGAAAAGTGAAATGAATAGTTCGACAAAGATCGCATTGGTAATTACGTTACTCGATGCCA TGGGGATTGGCCTTATCATGCCAGTCTTGCCAACGTTATTACGTGAATTTATTGCTTCGGAA GATATCGCTAACCACTTTGGCGTATTGCTTGCACTTTATGCGTTAATGCAGGTTATCTTTGC TCCTTGGCTTGGAAAAATGTCTGACCGATTTGGTCGGCGCCCAGTGCTGTTGTTGTCATTAA TAGGCGCATCGCTGGATTACTTATTGCTGGCTTTTTCAAGTGCGCTTTGGATGCTGTATTTA GGCCGTTTGCTTTCAGGGATCACAGGAGCTACTGGGGCTGTCGCGGCATCGGTCATTGCCGA TACCACCTCAGCTTCTCAACGCGTGAAGTGGTTCGGTTGGTTAGGGGCAAGTTTTGGGCTTG GTTTAATAGCGGGGCCTATTATTGGTGGTTTTGCAGGAGAGATTTCACCGCATAGTCCCTTT TTTATCGCTGCGTTGCTAAATATTGTCACTTTCCTTGTGGTTATGTTTTGGTTCCGTGAAAC CAAAAATACACGTGATAATACAGATACCGAAGTAGGGGTTGAGACGCAATCGAATTCGGTA TACATCACTTTATTTAAAACGATGCCCATTTTGTTGATTATTTATTTTTCAGCGCAATTGAT AGGCCAAATTCCCGCAACGGTGTGGGTGCTATTTACCGAAAATCGTTTTGGATGGAATAGCA TGATGGTTGGCTTTTCATTAGCGGGTCTTGGTCTTTTACACTCAGTATTCCAAGCCTTTGTG GCAGGAAGAATAGCCACTAAATGGGGCGAAAAAACGGCAGTACTGCTCGGATTTATTGCAG ATAGTAGTGCATTTGCCTTTTTAGCGTTTATATCTGAAGGTTGGTTAGTTTTCCCTGTTTTA ATTTTATTGGCTGGTGGTGGGATCGCTTTACCTGCATTACAGGGAGTGATGTCTATCCAAAC AAAGAGTCATCAGCAAGGTGCTTTACAGGGATTATTGGTGAGCCTTACCAATGCAACCGGTG TTATTGGCCCATTACTGTTTGCTGTTATTTATAATCATTCACTACCAATTTGGGATGGCTGG ATTTGGATTATTGGTTTAGCGTTTTACTGTATTATTATCCTGCTATCGATGACCTTCATGTT AACCCCTCAAGCTCAGGGGAGTAAACAGGAGACAAGTGCTTAGTTATTTCGTCACCAAATGA TGTTATTCCGCGAAATATAATGACCCTCTTGATAACCCAAGAGCATCACATATACCTGCCGT TCACTATTATTTAGTGAAATGAGATATTATGATATTTTCTGAATTGTGATTAAAAAGGCAA CTTTATGCCCATGCAACAGAAACTATAAAAAATACAGAGAATGAAAAGAAACAGATAGATT TTTTAGTTCTTTAGGCCCGTAGTCTGCAAATCCTTTTATGATTTTCTATCAAACAAAAGAGG AAAATAGACCAGTTGCAATCCAAACGAGAGTCTAATAGAATGAGGTCGAAAAGTAAATCGC GCGGGTTTGTTACTGATAAAGCAGGCAAGACCTAAAATGTGTAAAGGGCAAAGTGTATACT TTGGCGTCACCCCTTACATATTTTAGGTCTTTTTTTATTGTGCGTAACTAACTTGCCATCTT CAAACAGGAGGGCTGGAAGAAGCAGACCGCTAACACAGTACATAAAAAAGGAGACATGAAC GATGAACATCAAAAAGTTTGCAAAACAAGCAACAGTATTAACCTTTACTACCGCACTGCTGG CAGGAGGCGCAACTCAAGCGTTTGCGAAAGAAACGAACCAAAAGCCATATAAGGAAACATA CGGCATTTCCCATATTACACGCCATGATATGCTGCAAATCCCTGAACAGCAAAAAAATGAAA AATATCAAGTTCCTGAGTTCGATTCGTCCACAATTAAAAATATCTCTTCTGCAAAAGGCCTG GACGTTTGGGACAGCTGGCCATTACAAAACGCTGACGGCACTGTCGCAAACTATCACGGCTA CCACATCGTCTTTGCATTAGCCGGAGATCCTAAAAATGCGGATGACACATCGATTTACATGT TCTATCAAAAAGTCGGCGAAACTTCTATTGACAGCTGGAAAAACGCTGGCCGCGTCTTTAAA GACAGCGACAAATTCGATGCAAATGATTCTATCCTAAAAGACCAAACACAAGAATGGTCAG GTTCAGCCACATTTACATCTGACGGAAAAATCCGTTTATTCTCACTGATTTCTCCGGTAAA CATTACGGCAAACAAACACTGACAACTGCACAAGTTAACGTATCAGCATCAGACAGCTCTTT GAACATCAACGGTGTAGAGGATTATAAATCAATCTTTGACGGTGACGGAAAAACGTATCAA AATGTACAGCAGTTCATCGATGAAGGCAACTACAGCTCAGGCGACAACCATACGCTGAGAGA TCCTCACTACGTAGAAGATAAAGGCCACAAATACTTAGTATTTGAAGCAAACACTGGAACTG AAGATGGCTACCAAGGCGAAGAATCTTTATTTAACAAAGCATACTATGGCAAAAGCACATC ATTCTTCCGTCAAGAAAGTCAAAAACTTCTGCAAAGCGATAAAAAACGCACGGCTGAGTTAG CAAACGGCGCTCTCGGTATGATTGAGCTAAACGATGATTACACACTGAAAAAAGTGATGAA ACCGCTGATTGCATCTAACACAGTAACAGATGAAATTGAACGCGCGAACGTCTTTAAAATGA ACGGCAAATGGTACCTGTTCACTGACTCCCGCGGATCAAAAATGACGATTGACGGCATTACG TCTAACGATATTTACATGCTTGGTTATGTTTCTAATTCTTTAACTGGCCCATACAAGCCGCT GAACAAAACTGGCCTTGTGTTAAAAATGGATCTTGATCCTAACGATGTAACCTTTACTTACT CACACTTCGCTGTACCTCAAGCGAAAGGAAACAATGTCGTGATTACAAGCTATATGACAAAC AGAGGATTCTACGCAGACAAACAATCAACGTTTGCGCCAAGCTTCCTGCTGAACATCAAAGG CAAGAAAACATCTGTTGTCAAAGACAGCATCCTTGAACAAGGACAATTAACAGTTAACAAA TAAAAACGCAAAAGAAAATGCCGATATTGACTACCGGAAGCAGTGTGACCGTGTGCTTCTCA AATGCCTGATTCAGGCTGTCTATGTGTGACTGTTGAGCTGTAACAAGTTGTCTCAGGTGTTC AATTTCATGTTCTAGTTGCTTTGTTTTACTGGTTTCACCTGTTCTATTAGGTTGTTACATGCT GTTCATCTGTTACATTGTCGATCTGTTCATGGTGAACAGCTTTAAATGCACCAAAAACTCGT AAAAGCTCTGATGTATCTATCTTTTTTACACCGTTTTCATCTGTGCATATGGACAGTTTTCC CTTTGAT (SEQ ID NO: 2]) |
| ΔilcR_cure | AAATGATTTCCACGATACAGAAAAAAGAGACTGTCATGGGCAGAATATTGCCTCTGCCCG CCAGAAAAAG (SEQ ID NO: 3]) |
| ΔarcA_cure | CTGTTTCGATTTAGTTGGCAATTTAGGTAGCAAACTCGGCTTTACCACCGTCAAAAAAAAC GGCGCTTTT (SEQ ID NO: 4]) |
| ilcR-tetA-F | TAACAATAAAAATGAAATGATTTCCACGATACAGAAAAAAGAGACTGT CATCCTAATTTTTGTTGACACTCTATC (SEQ ID NO: 5]) |
| ilcR_sacB_R | TGCCACTCAGGTATGATGGGCAGAATATTGCCTCTGCCCGCCAGAAAAA GATCAAAGGGAAAACTGTCCATATGC (SEQ ID NO: 6]) |
| iclR_500up | CCGACAGGGA TTCCA TCTG (SEQ ID NO: 7]) |
| iclR_500dn | TATGACGACCATTTTGTCTACAGTTC (SEQ ID NO: 8) |

TABLE 6-continued

| Name | Sequence |
|------|----------|
| arcA-tetA-F | GGACTTTTGTACTTCCTGTTTCGATTTAGTTGGCAATTTAGGTAGCAAACT CCTAATTTTTGTTGACACTCTATC (SEQ ID NO: 9]) |
| arcA_sacB_R | ATAAAAACGGCGCTAAAAAGCGCCGTTTTTTTTGACGGTGGTAAAGCCG AATCAAAGGGAAAACTGTCCATATGC (SEQ ID NO: 10]) |
| arcA_500up | CCTGACTGTACTAACGGTTGAG (SEQ ID NO: 11]) |
| arcA_500dn | TGACTTTTATGGCGTTCTTTGTTTTTG (SEQ ID NO: 12]) |
| OmpTKO_AprR_ F | AGATATAAAAAATACATATTCAATCATTAAAACGATTGAATGGAGAACTTTTGGCTGACGC CGTTGGATAC (SEQ ID NO: 13)] |
| OmpTKO_AprR_ R | TTTAAGGGTTAATTGTTACATTGAAATGGCTAGTTATTCCCCGGGGCGATTCAGCCAATCGA CTGGCGAG (SEQ ID NO: 14]) |
| OmpT_up | CCTCATGCTATTTTCGCTTATATGC (SEQ ID NO: 15]) |
| OmpT_dn | GATTATTATGGTGTCACGCCATCTC (SEQ ID NO: 16]) |

Table 5.1: Synthetic DNA and Oligos used for plasmid construction

| | |
|------|----------|
| pCDF-1b_ampl1 | GTCATCGTGGCCGGATCTTG (SEQ ID NO: 17]) |
| pCDF-1b_ampl2 | ATTAATGCAGCTGGCACGACAG (SEQ ID NO: 18]) |
| pCDF-MCS | CTGTCGTGCCAGCTGCATTAATCAGTCCAGTTACGCTGGAGTCCAGTCCAGTTACGCTGG AGTCTGAGGCTCGTCCTGAATGATATCAAGCTTGAATTCGTTGACGAATTCTCTAGATAT CGCTCAATACTGACCATTTAAATCATACCTGACCGTCATCGTGGCCGGATCTTG (SEQ ID NO: 19]) |
| yibDp-GFPuv | TGAGGCTCGTCCTGAATGATATCAAGCTTGAATTCGTTGTGCGTAATTGTGCTGATCTCT TATATAGCTGCTCTCATTATCTCTCTACCCTGAAGTGACTCTCTCACCTGTAAAAATAAT ATCTCACAGGCTTAATAGTTTCTTAATACAAAGCCTGTAAAACGTCAGGATAACTTCTTG TAGGAGGATAATCTATGGCTAGCAAAGGAGAAGAACTTTTCACTGGAGTTGTCCCAATTC TTGTTGAATTAGATGGTGATGTTAATGGGCACAAATTTTCTGTCAGTGGAGAGGGTGAA GGTGATGCTACATACGGAAAGCTTACCCTTAAATTTATTTGCACTACTGGAAAACTACCT GTTCCATGGCCAACACTTGTCACTACTTTCTCTTATGGTGTTCAATGCTTTTCCCGTTATC CGGATCATATGAAACGGCATGACTTTTTCAAGAGTGCCATGCCCGAAGGTTATGTACAGG AACGCACTATATCTTTCAAAGATGACGGGAACTACAAGACGCGTGCTGAAGTCAAGTTTG AAGGTGATACCCTTGTTAATCGTATCGAGTTAAAAGGTATTGATTTTAAAGAAGATGGA AACATTCTCGGACACAAACTCGAGTACAACTATAACTCACACAATGTATACATCACGGCA GACAAACAAAGAATGGAATCAAAGCTAACTTCAAAATTCGCCACAACATTGAAGATGG ATCCGTTCAACTAGCAGACCATTATCAACAAAATACTCCAATTGGCGATGGCCCTGTCCT TTTACCAGACAACCATTACCTGTCGACACAATCTGCCCTTTCGAAAGATCCCAACGAAAA GCGTGACCACATGGTCCTTCTTGAGTTTGTAACTGCTGCTGGGATTACACATGGCATGGA TGAGCTCTACAAATAATGAGGATCCCCGGCTTATCGGTCAGTTTCACCTGATTTACGTAA AAACCCGCTTCGGCGGGTTTTTGCTTTTGGAGGGGCAGAAAGATGAATGACTGTCCACGA CGCTATACCCAAAAGAAAGACGAATTCTCTAGATATCGCTCAATACTGA (SEQ ID NO: 20]) |
| yibDp-mCherry | GTCTGAGGCTCGTCCTGAATGATATCAAGCTTGAATTCGTTCGTGCGTAATTGTGCTGAT CTCTTATATAGCTGCTCTCATTATCTCTCTACCCTGAAGTGACTCTCTCACCTGTAAAAA TAATATCTCACAGGCTTAATAGTTTCTTAATACAAAGCCTGTAAAACGTCAGGATAACTT CTGTGTAGGAGGATAATCTATGGTATCAAAAGGAGAGGAAGATAACATGGCTATTATCA AAGAATTTATGCGCTTCAAAGTTCACATGGAAGGTAGCGTGAACGGTCACGAGTTCGAG ATTGAAGGTGAAGGTGAAGGGCGTCCGTACGAAGGTACACAGACCGCTAAACTGAAGGT GACGAAAGGTGGCCCTCTTCCATTTGCGTGGGATATTCTTAGTCCGCAATTTATGTATGG ATCTAAGGCGTATGTCAAGCACCCGGCTGACATCCCAGATTACTTAAAACTTAGCTTCCC AGAGGGATTCAAATGGGAGCGCGTTATGAATTTCGAGGACGGCGGTGTAGTGACCGTCAC TCAGGATTCATCACTTCAAGATGGCGAATTTATCTACAAGGTCAAGCTGCGTGGGACAAA TTTTCCGTCGGATGGGCCTGTCATGCAGAAGAAGACAATGGGCTGGGAAGCGTCGTCAGA GCGTATGTATCCAGAGGACGGAGCGTTAAAAGGGGAAATTAAGCAGCGCCTGAAGTTGA AGGATGGCGGGCATTATGACGCAGAGGTTAAAACCACTTATAAAGCGAAAAAGCCAGTC CAATTGCCAGGAGCCTACAATGTCAATATCAAATTAGATATCACAAGTCATAACGAGGAT TACACGATCGTCGAACAATATGAGCGCGCAGAAGGTCGCCATAGTACAGGAGGAATGGAC GAACTGTACAAATAATGACTCGAGtctggtaaaactagcatTCGACCTAGCATAACCCCGCGGG GCCTCTTCGGGGGTCTCGCGGGGTTTTTTGCTGAAAGAAGCTTCAAATAAAACGAAAGGC TCAGTCGAAAGACTGGGCCTTTCGTTTTATCTGTTGTTTGTCGGTGAACGCTCTCTACTAGAGT ATGATTTAAATGGTCAGTAACGGGTCTTGAGGGGTTTTTTGCAATGGGTTCATCCCGTGG GGACGAATTCTCTAGATATCGCTCAATACTGA (SEQ ID NO: 21]) |
| yibDp-matB | TGCCCAGGCATCAAATAAAACGAAAGGCTCAGTCGAAAGACTGGGCCTTTCGTTTTATCT GTTGTTTGTCGGTGAACGCTCTCTACTAGAGTCACACTGGCTCACCTTCGGGTGGGCCTT TCTGCGTTTATACACAGCTAACACCACGTCGTCCCTATCTGCTGCCCTAGGTCTATGAGT GGTTGCTGGATAACGTGCGTAATTGTGCTGATCTCTTATATAGCTGCTCTCATTATCTCT CTACCCTGAAGTGACTCTCTCACCTGTAAAAATAATATCTCACAGGCTTAATAGTTTCTT AATACAAAGCCTGTAAAACGTCAGGATAACTTCTATATTCAGGGAGACCACAACGGTTTC |

TABLE 6-continued

| Name | Sequence |
|---|---|
| | CCTCTACAAATAATTTTGTTTAACTTTGGAAAAAGGAGATATACCATGCATCATCATCAT |
| | CATCACTCCAACCATTTATTCGATGCGATGCGTGCCGCGGCGCCTGGGAATGCGCCGTTC |
| | ATCCGCATCGACAATACACGCCACCTGGACCTACGACGATGCCTTTGCCTTGAGTGGTCGC |
| | ATTGCGTCAGCTATGGACGCACTCGGCATTCGCCCGGGAGACCGCGTGGCCGTGCAGGTG |
| | GAGAAATCTGCCGAAGCACTGATTCTGTATCTTGCGTGTCTGCGTAGCGGTGCCGTATAT |
| | TTGCCACTGAACACTGCTTATACACTTGCGGAACTGGACTACTTTATTGGTGATGCCGAA |
| | CCGCGCCTCGTTGTTGTAGCGTCATCCGCCCGTGCAGGTGTGGAAACCATTGCGAAACCG |
| | CGCGGGGCCATTGTAGAAACTCTGGATGCAGCTGGCAGCGGAAGCTTGCTGGACTTGGCG |
| | CGCGATGAGCCTGCTGATTTCGTGGACGCTAGTCGCTCGGCGGACGATCTGGCGGCAATT |
| | CTTTATACAAGTGGGACGACAGGGCGTTCTAAGGGGGCAATGCTGACACACGGCAACCTG |
| | CTTTCTAACGCGCTTACATTGCGTGATTTCTGGCGTGTAACCGCAGGCGATCGTCTGATT |
| | CATGCGTTACCGATTTTTCATACACATGGCCTGTTTGTCGCTACTAATGTCACATTACTG |
| | GCCGGGGCCTCTATGTTTCTGTTAAGCAAATTTGATCCGGAAGAGATCCTGTCTTTGATG |
| | CCGCAGGCTACCATGCTGATGGGCGTACCGACCTTCTATGTTCGCTTGCTGCAATCACCGC |
| | GCCTGGATAAACAGGCAGTAGCGAATATTCGCCTGTTTATTAGTGGGTCCGCACCACTGC |
| | TGGCAGAGACACACACTGAATTTCAAGCGCGTACCGGCCATGCCATTCTGGAACGCTACG |
| | GAATGACCGAGACCAACATGAACACCTCAAATCCGTATGAGGGTAAACGTATTGCGGGTA |
| | CTGTGGGCTTTCCTCTCCCGGATGTCACTGTTCGTGTTACCGACCCGGCAACCGGTCTCGC |
| | CTTACCTCCGGAACAGACGGGAATGATCGAAATTAAAGGTCCGAACGTGTTTAAGGGCTA |
| | TTGGCGCATGCCCGAGAAGACCGCTGCCGAATTCACCGCCGATGGTTTCTTTATCAGTGG |
| | TGATTTAGGTAAAATCGATCGCGATGGATACGTTCATATTGTGGGGCGCGGGAAAGATC |
| | TGGTTATTTCAGGAGGCTATAATATTTATCCGAAAGAAGTTGAGGGGGAAATTGACCAG |
| | ATTGAAGGGGTGGTTGAATCAGCAGTGATCGGCGTTCCGCACCCGGATTTTGGTGAAGGT |
| | GTCACAGCGGTTGTGGTTCGCAAACCAGGGGCGGCTCTGGATGAAAAAGCGATCGTCTCT |
| | GCTCTGCAGGACCGTCTGGCTCGTTATAAACAACCGAAACGCATCATTTTTGCTGAAGAT |
| | CTGCCGCGTAACACAATGGGTAAAGTCCAGAAAAACATCTTGCGCCAGCAGTATGCAGAC |
| | TTATATACTCGTACGTAGTAAGACGAATTCTCTAGATATCGCTCAATACTG |
| | (SEQ ID NO: 22]) |
| yibDp-mdlC-his1 | CCTGACGTTTTACAGGCTTTGTATTAAGAAACTATTAAGCCTGTGAGATATTATTTTTAC |
| | AGGTGAGAGAGTCACTTCAGGGTAGAGAGATAATGAGAGCAGCTATATAAGAGATCAGC |
| | ACAATTACGCACTTATTTGCCGACTACCTTGGTGATCTCGCCTTTCACGTAGTGGACAAA |
| | TTCTTCCAACTGATCTGCGCGCGAGGCCAAGCGATCTTCTTCTTGTCCAAGATAAGCCTG |
| | TCTAGCTTCAAGTATGACGGGCTGATACTGGGCCGGCAGGCGCTCCATTGCCCAGTCGGC |
| | AGCGACATCCTTCGGCGCGATTTTGCCGGTTACTGCGCTGTACCAAATGCGGGACAACGT |
| | AAGCACTACATTTCGCTCATCGCCAGCCCAGTCGGGCGGCGAGTTCCATAGCGTTAAGGT |
| | TTCATTTAGCGCCTCAAATAGATCCTGTTCAGGAACCGGATCAAAGAGTTCCTCCGCCGC |
| | TGGACCTACCAAGGCAACGCTATGTTCTCTTGCTTTTGTCAGCAAGATAGCGAGATCAAT |
| | GTCGATCGTGGCTGGCTCGAAGATACCTGCAAGAATGTCATTGCGCTGCCATTCTCCAAA |
| | TTGCAGTTCGCGCTTAGCTGGATAACGCCACGGAATGATGTCGTCGTGCACAACAATGGT |
| | GACTTCTACAGCGCGGAGAATCTCGCTCTCTCCAGGGGAAGCCGAAGTTTCCAAAAGGTC |
| | GTTGATCAAAGCTCGCCGCGTTGTTTCATCAAGCCTTACGGTCACCGTAACCAGCAAATC |
| | AATATCACTGTGTGGCTTCAGGCCGCCATCCACTGCGGAGCCGTACAAATGTACGGCCAG |
| | CAACGTCGGTTCGAGATGGCGCTCGATGACGCCAACTACCTCTGATAGTTGAGTCGATAC |
| | TTCGGCGATCACCGCTTCCCTCATACTCTTCCTTTTTCAATATTATTGAAGCATTTATCA |
| | GGGTTATTGTCTCATGAGCGGATACATATTTGAATGTATTTAGAAAAATAAACAAATAG |
| | CTAGCTCACTCGGTCGCTACGCTCCGGGCGTGAGACTGCGGCGGGCGCTGCGGACACATA |
| | GAAAGTTACCCACAGATTCGGTGGATAAGCAGGGGACTAACATGTGAGGCAAAACAGCA |
| | GGGCCGCGCCGGTGGCGTTTTTCCATAGGCTCCGCCCTCCTGCCAGAGTTCACATAAACA |
| | GACGCTTTTCCGGTGCATCTGTGGGAGCCGTGAGGCTCAACCATGAATCTGACAGTACGG |
| | GCGAAACCCGACAGGACTTAAAGATCCCCACCGTTTCCGGCGGGTCGCTCCCTCTTGCGCT |
| | CTCCTGTTCCGACCCTGCCGTTTACCGGATACCTGTTCCGCCTTTCTCCCTTACGGGAAGT |
| | GTGGCGCTTTCTCATAGCTCACACACTGGTATCTCGGCTCGGTGTAGGTCGTTCGCTCCA |
| | AGCTGGGCTGTAAGCAAGAACTCCCCGTTCAGCCCGACTGCTGCGCCTTATCCGGTAACT |
| | GTTCACTTGAGTCCAACCCGGAAAAGCACGGTAAAACGCCACTGGCAGCAGCCATTGGTA |
| | ACTGGGAGTTCGCAGAGGATTTGTTTAGCTAAACACGCGGTTGCTCTTGAAGTGTGCGCC |
| | AAAGTCCGGCTACACTGGAAGGACAGATTTGGTTGCTGTGCTCTGCGAAAGCCAGTTACC |
| | ACGGTTAAGCAGTTCCCCAACTGACTTAACCTTCGATCAAACCACCTCCCCAGGTGGTTT |
| | TTTCGTTTACGGGCAAAAGATTACGCGCAGAAAAAAAGGATCTCAAGAAGATCCTTTG |
| | ATCTTTTCTACTGAACCGCTCTGC (SEQ ID NO: 23]) |
| yibDp-mdlC-his2 | AGCCTGTAAAACGTCAGGATAACTTCTATATTCAGGGAGACCACAACGGTTTCCCTCTAC |
| | AAATAATTTTGTTTAACTTTCGTGTGTAGGAGGATAATCTATGTATACGGTGGGGGACT |
| | ACTTGCTTGATCGCCTGCACGAGTTAGGCATCGAGGAAATTTTTGGTGTACCCGGGGACT |
| | ATAACCTCCAGTTCCTTGATCAGATCATTTCACGTGAGGATATGAAATGGATTGGGAACG |
| | CCAATGAACTTAACGCATCATATATGGCGGATGGATATGCTCGCACAAAAAAAGCCGCGG |
| | CTTTTCTTACAACTTTCGGCGTGGGGGAGTTAAGTGCTATCAATGGATTGGCCGGCTCGT |
| | ATGCTGAAAATCTGCCCGTTGTAGAAATCGTAGGTAGCCCAACCTCCAAGGTCCAGAACG |
| | ACGGTAAATTCGTCCACCACACTTTAGCAGATGGCGATTTTAAGCACTTCATGAAGATCC |
| | ATGAACCGGTGACAGCTGCCCGCACTCTTTTGACCGCCGAGAATGCGACTTATGAAATTG |
| | ATCGTGTCTTAAGTCAACTGCTGAAGGAACGTAAACCAGTTTACATTAACTTACCCGTCG |
| | ATGTCGCGGCAGCTAAGGCAGAGAAACCAGCCTTGAGTTTGGAGAAGGAAAGTTCAACC |
| | ACAAACACCACCGAGCAAGTTATTCTTTCAAAGATTGAAGAGTCCTTGAAGAACGCCCAA |
| | AAACCAGTCGTTATTGCCGGTCATGAGGTTATCAGTTTCGGGCTTGAGAAAACAGTCACG |
| | CAATTCGTCTCCGAGACCAAACTTCCAATCAGAACGCTGAATTTCGGCAAGTCTGCCGGTC |
| | GATGAATCATTACCTTCGTTTTTGGGGATCTATAATGGTAAACTGAGTGAGATCTCTCTT |
| | AAAAACTTTGTCGAATCAGCCGATTTTATCTTAATGCTTGGCGTGAAATTAACGGACTCA |
| | TCTACTGGCGCTTTTACCCATCATTGGATGAAAATAAAATGATTTCTCTTAATATCGAT |

TABLE 6-continued

| Name | Sequence |
|---|---|
| | GAGGGTATTATTTTCAATAAGGTGGTAGAGGATTTCGATTTTCGCGCAGTTGTCTCGTCA<br>TTATCAGAACTTAAAGGTATTGAGTACGAAGGACAATATATGGATAAACAGTACGAAGA<br>GTTTATCCCGAGCAGCGCACCACTTTCTCAAGATCGCTTATGGCAAGCAGTGGAGAGCCT<br>GACTCAGTCAAATGAAACTATTGTCGCTGAACAAGGAACGTCTTTTTTTGGTGCCTCTAC<br>TATCTTCCTTAAAAGCAACTCGCGTTTCATCGGCCAACCACTGTGGGGGTCAATCGGGTA<br>CACGTTCCCCGCTGCTCTTGGGTCTCAGATTGCCGACAAGGAGAGTCGCCATCTGTTATT<br>CATTGGTGACGGGTCCCTTCAACTGACTGTTCAGGAGTTAGGCCTGTCTATCCGCGAAAA<br>ATTGAATCCAATCTGTTTTATCATTAATAATGACGGTTATACCGTGGAGCGCGAGATCCA<br>TGGGCCAACACAAAGCTACAACGACATTCCCATGTGGAATTATTCGAAGCTTCCGGAAAC<br>TTTTGGAGCAACAGAGGACCGTGTTGTAAGCAAGATCGTTCGCACGGAGAATGAGTTCGT<br>ATCCGTTATGAAGGAAGCTCAAGCGGACGTTAACCGTATGTATTGGATTGAACTGGTTTT<br>GGAAAAAGAGGATGCCCCCAAGTTATTGAAAAAAATGGGAAAATTGTTCGCGGAGCAGA<br>ATAAGCATCATCACCACCACCACTGATGTTGACCGCAAAAAACCCCGCTTCGGCGGGGTT<br>TTTTCGCAGAGCGGTTCAGTAGAAA (SEQ ID NO: 24]) |
| yibDp-GST | TGAGGCTCGTCCTGAATGATATCAAGCTTGAATTCGTTTGCCCAGGCATCAAATAAAACG<br>AAAGGCTCAGTCGAAAGACTGGGCCTTTCGTTTTATCTGTTGTTTGTCGGTGAACGCTCT<br>CTACTAGAGTCACACTGGCTCACCTTCGGGTGGGCCTTTCTGCGTTTATACACAGCTAAC<br>ACCACGTCGTCCCTATCTGCTGCCCTAGGTCTATGAGTGGTTGCTGGATAACGTGCGTAA<br>TTGTGCTGATCTCTTATATAGCTGCTCTCATTATCTCTCTACCCTGAAGTGACTCTCTCAC<br>CTGTAAAAATAATATCTCACAGGCTTAATAGTTTCTTAATACAAAGCCTGTAAAACGTCA<br>GGATAACTTCTATATTCAGGGAGACCACAACGGTTTCCCTCTACAAATAATTTTGTTTAA<br>CTTTAAAGAGGAGAAATACTAGATGGGGAACGCAGCATCTGCGCGCCGCATGTCCCCGAT<br>CCTGGGTTACTGGAAAATCAAAGGGTTAGTGCAGCCAACCCGTCTGTTATTAGAATACCT<br>GGAGGAAAAATACGAGGAACACCTGTACGAGCGCGATGAAGGCGATAAATGGCGCAATA<br>AAAAATTCGAACTCGGGCTGGAATTCCCAAACTTACCCTATTATATTGATGGAGATGTTA<br>AATTGACCCAGTCTATGGCAATCATTCGCTATATTGCAGATAAACATAACATGTTGGGCG<br>GCTGTCCTAAGGAGCGCGCGGAAATTAGTATGCTGGAAGGCGCGGTGCTGGATATCCGCT<br>ATGGTGTTAGCCGCATTGCGTACTCGAAAGATTTTGAGACGCTCAAAGTTGATTTTCTGA<br>GTAAACTGCCTGAAATGTTAAAGATGTTTGAAGATCGCTTGTGTCACAAAACGTATTTA<br>AATGGTGATCATGTCACCCATCCAGACTTTATGCTGTATGATGCGCTTGATGTGGTTTTG<br>TACATGGATCCGATGTGCCTGGATGCCTTTCCGAAGCTGGTCTGTTTCAAAAAACGCATC<br>GAGGCTATTCCGCAAATCGACAAATATCTCAAATCTAGTAAATACATCGCGTGGCCTCTG<br>CAGGGCTGGCAAGCGACCTTTGGTGGGGGCGATCATCCGCCAAATGATAAGACGAATTC<br>TCTAGATATCGCTCAATACTGA (SEQ ID NO: 25]) |
| pHCKan-T7-CBD-<br>hGLY | CATTGCATAATACGACTCACTATAGGGAGACCACAACGGTTTCCCACTAGAAATAATTTT<br>GTTTAACTTTAAGAAGGAGATATACATAAAGAGGAGAAATACTAGATGACAAATCCTGG<br>TGTAAGTGCCTGGCAAGTTAATACCGCATATACCGCTGGGCAGTTAGTCACTTATAACGG<br>CAAGACCTACAAGTGCTTGCAGCCTCACACATCCTTGGCAGGTTGGGAACCGTCCAATGT<br>ACCCGCCCTTTGGCAACTTCAGGGCTCTGCCGGTAGTGCGGCGGGTTCCGGTGAATTTAT<br>GCTGGTTCTGCACAACAGCCAAAAACTGCAAATTCTGTACAAATCTCTGGAAAAATCTAT<br>TCCTGAAAGCATTAAAGTTTATGGTGCGATCTTCAACATCAAGGATAAAAACCCTTTCAA<br>TATGGAGGTGCTGGTCGACGCGTGGCCTGATTACCAAATCGTCATCACCCGTCCGCAGAA<br>GCAAGAAATGAAAGATGACCAGGACCACTATACTAACCACCTACCACATCTTCACTAAAGC<br>GCCGGACAAACTGGAAGAAGTTCTGAGCTACTCCAATGTTATCTCCTGGGAACAAACGCT<br>GCAGATTCAAGGTTGCCAGGAAGGTCTGGATGAGGCGATTCGTAAGGTCGCTACCTCTAA<br>GTCCGTTCAAGTCGATTACATGAAAAACCATCCTGTTTATCCCGGAGCTGCCGAAGAAACA<br>CAAAACCTCCTCTAACGACAAGATGGAGCTGTTCGAAGTAGACGATGACAACAAAGAGG<br>GTAACTTTTCCAATATGTTCCTGGACGCCTCCCACGCCGGTCTGGTTAATGAGCACTGGG<br>CGTTCGGTAAAAACGAACGCTCCCTGAAGTACATTGAGCGTTGTCTGCAGGATTTTCTGG<br>GTTTTGGTGTCCTGGGTCCAGAGGGTCAACTGGTCTCTTGGATCGTTATGGAACAGTCTT<br>GTGAACTGCGTATGGGTTATACTGTGCCAAAATACCGTCACCAAGGTAATATGCTGCAAA<br>TCGGTTATCATCTGGAGAAGTACCTGAGCCAGAAGGAAATCCCGTTCTATTTCCATGTTG<br>CCGATAATAACGAAAAGAGCCTGCAAGCCCTGAACAATCTGGGCTTCAAGATCTGCCCTT<br>GCGGTTGGCACCAGTGGAAGTGCACGCCTAAAAAGTACTGTGGCGGTGGCCATCATCACC<br>ATCACCATTAATGA (SEQ ID NO: 26]) |
| SL1_rc | ACTCCAGCGTAACTGGACTG (SEQ ID NO: 27]) |
| SR2_rc | ACTGACCATTTAAATCATACCTGACC (SEQ ID NO: 28]) |
| GFP_cp6_F | AGCAGCCATCACCCATC (SEQ ID NO: 29]) |
| GFP_cp6_R | GCCCATATGTATATCTCCTTCTTAAAG (SEQ ID NO: 30]) |
| pS-yibD-hGLY_F | CTGGAAAAAGGAGATATACCATGACAAATCCTGGTGTAAGTGCC (SEQ ID NO: 31]] |
| pS-yibD-hGLY_R | GTGAGTCGTATTAGAAGAGCTCATTAATGGTGATGGTGATGATGGC (SEQ ID NO: 32]) |
| pS-yibDp-FOR | TAATGAGCTCTTCTAATACGACTCACTATAGGG (SEQ ID NO: 33]) |
| pS-yibDp-REV | CATGGTATATCTCCTTTTTCCAGAAGTG (SEQ ID NO: 34]] |

BioLector™ Experiments: Growth and fluorescence measurements were obtained in a Biolector (m2p labs, 11 Baesweiler, Germany) using a high mass transfer Flower-Plate (CAT #: MTP-48-B, m2p-labs, Biolector settings are as follows: RFP gain=40, GFP gain=20, Biomass gain 20, shaking speed 1300 rpm, temperature 37° C., humidity 85%. Single colonies of each strain were inoculated into 5 mL LB with appropriate antibiotics and cultured at 37° C., 150 rpm overnight. Overnight cultures OD600 nm was measured and normalized to OD600 nm=25.8 μL of normalized overnight culture was inoculated into 792 μL of the appropriate medium with appropriate antibiotics and transferred into wells of the FlowerPlate. Every strain was analyzed in triplicate.

Microtiter Plate Based Growth and Expression: Plasmids were transformed into host strains using standard protocols. Glycerol stocks were prepared for each strain plate by adding equal volume of overnight LB culture with sterile 20% glycerol. 3 μL of glycerol stocks were used to inoculate overnight culture in 150 μL LB medium with appropriate antibiotics. 96 well and 384 well plates used in these studies were obtained from Genesee Scientific (San Diego, CA, Cat #: 25-104) and VWR ((Suwanee, GA, Cat #: 10814-224). Plates were covered with sandwich covers (Model #CR1596, 96 well plates) (Model #CR1384, 384 well plates) obtained from EnzyScreen, Haarlam, The Netherlands). These covers ensured minimal evaporative loss during incubation. Microtiter plates were cultured at 37° C., 300 rpm for 16 hours, shaker orbit is 50 mm. This combination of orbit and minimal shaking speed is required to obtain needed mass transfer coefficient and enable adequate culture oxygenation. After 16 hours of growth, a 1% volume of overnight culture was inoculated into autoinduction media plus the appropriate antibiotics. Plates were again covered with sandwich covers and grown at 37° C., 300 rpm for 24 hours at which point samples were harvested for analysis, ie SDS-PAGE, fluorescence and optical density readings. To test the expression level of the protein panel, a volume of 100 μL of AB media per well was used.

Autoinduction Media Development

The autoinduction media was developed using DoE definitive screening designs and JMP software (SAS, Cary, NC). 1× trace metal mix contains 0.01 mL/L of concentrated H2SO4, 0.0012 g/L CoSO4*7H2O, 0.001 g/L CuSO4*5H2O, 0.0012 g/L ZnSO4*7H2O, 0.0004 g/L Na2MoO4*2H2O, 0.0002 g/L H3B03, and 0.0006 g/L MnSO4*H2O. 0.25 g/L citric acid, 68 mM (NH4)2SO4, 0.16 mM FeSO4, 10 mM MgSO4, 0.0625 mM CaSO4, 2× trace metal mix, 2.5 g/L yeast extract, and 2.5 g/L casamino acid were used as the starting center point, 4× and 1/4× of the center point values were used as the upper and lower concentration ranges. Definitive screening design was performed in 5 iterations. Center point, upper and lower concentration ranges for future iterations were determined based on DoE results from the previous iteration. For testing all 212 media from the DoE, one mL of each media was prepared in deep well 96-well plates. Media were prepared from sterilized liquid stocks: (NH4)2SO4 (3 M), Citric Acid (25 g/L), FeSO4 (20 mM), MgSO4 (1 M), CaSO4 (5 mM), Trace Metals (250×), Yeast Extract (100 g/L), Casamino Acids (100 g/L), Thiamine HCl (50 g/L), MOPS (1 M), and glucose (500 g/L). As all media contained equal amounts of Thiamine HCl, MOPS, glucose, and Kanamycin, these were added to each media first, followed by water. Then worklists were prepared to add the remaining media components using Tecan Evo for liquid handling. In between addition of media components, plates were shaken in a Benchmark Incu- Mixer™ MP at 1500 rpm to ensure proper mixing and prevent media precipitation. Once completed, 148.5 uL of media was distributed to triplicate 96 well plates and each well was inoculated with 1.5 uL of overnight LB culture. The plates were covered with EnzyScreen covers and shaken at 300 rpm at 37° C. After 24 hours, OD and fluorescence were measured.

Shake Flask Growth and Expression: Glycerol stocks were used to inoculate overnight cultures in 5 mL of LB media, with appropriate antibiotics. After 16 hours of growth, a 1% volume of overnight culture was inoculated into autoinduction media plus the appropriate antibiotics. Flasks cultures were grown at 37° C., 150 rpm in baffled 250 ml Erlenmeyer flasks for 24 hours at which point samples were harvested for analysis.

Fermentation Seeds: Single colony from transformation plate was inoculated into 5 mL LB with appropriate antibiotics and cultured at 37° C., 150 rpm for 16 hours. 200 μL of the LB culture was inoculated into 20 mL SM10+ media with appropriate antibiotics in 250 ml shaker flasks. The culture was incubated at 37° C. with a shaking speed of 150 rpm for 16 hours, atwhich time OD600 nm is usually between 6 and 10. The culture was harvested by centrifugation at 4000 rpm for 15 min, the supernatant was discarded and the cell culture was normalized to OD600 nm=10 using FGM10 media. Seed vials were prepared by adding 1.5 mL of 50% glycerol to 6.5 mL of normalized OD600 nm=10 culture in cryovials, and stored at −60° C. [00109]1 L Fermentations: An Infors-HT Multifors (Laurel, MD, USA) parallel bioreactor system was used to perform 1 L fermentations. Vessels used had a total volume of 1400 mL and a working volume of up to 1 L. Online pH and β02 monitoring and control were accomplished with Hamilton probes. Offgas analysis was accomplished with a multiplexed Blue-in-One BlueSens gas analyzer (BlueSens. Northbrook, IL, USA). Culture densities were continually monitored using Optek 225 mm OD probes, (Optek, Germantown, WI, USA). The system used was running IrisV6.0 command and control software and integrated with a Segflow automated sampling system (Flownamics, Rodeo, CA, USA), including FISP cell free sampling probes, a Segmod 4800 and FlowFraction 96 well plate fraction collector. Tanks were filled with 800 mL of FGM10 medium, which has enough phosphate to target a final *E. coli* biomass concentration ~10 gCDW/L. Antibiotics were added as appropriate. Phosphate, glucose, thiamine and antibiotics were added after cooling the tank vessel containing the rest of FGM10 media components. Frozen seed vials were thawed on ice and 7.5 mL of seed culture was used to inoculate the tanks. After inoculation, tanks were controlled at 37° C. and pH 6.8 using 10 M ammonium hydroxide and 1 M hydrochloric acid as titrants. The following oxygen control scheme was used to maintain the desired dissolved oxygen set point. First air flow rate was set to 1 vvm. In order to maintain a dissolved oxygen concentration of 25%, agitation was increased from a minimum of 300 rpm to a maximum of 1000 rpm, and then airflow was increased up to 2 vvm. Starting batch glucose concentration was 25 g/L. A constant concentrated sterile filtered glucose feed (500 g/L) was added to the tanks at 1 g/h once dissolved oxygen concentration dropped from 100% to 80% and ramped up to 2 g/h, once agitation cells reached mid exponential phase (OD600 nm 1.5-7).

Organic Acid Quantification: Two orthogonal methods were used to quantify organic acids including lactate, acetate, succinate, fumarate, pyruvate, malate and others. The first method was a reverse phase UPLC method. Chromatographic separation was performed using a Restek Ultra AQ C18 column (150 mm×2.1 i.d., 3 μm; CAT #: 9178362, Restek Corporation, Bellefonte, PA) at 30° C. 20 mM phosphoric acid was used as the eluent. The isocratic elution rate was at 0.8 mL/min, run time was 1.25 min. Sample injection volume was 10 μL. Absorbance was monitored at 210 nm. The second method relied on ion exchange chromatography and refractive index detection. A Phenomenex Rezex™ ROA-Organic Acid H+(8%) (30×4.6 mm; CAT #: 00A-0138-E0, Phenomenex, Torrance, CA) was used for a 30 minute isocratic separation using a mobile phase of 5 mM H2SO4, at a flow rate of 0.5 mL/min. Again sample injections were 10 μL. Organic acid elution times were as follows: Pyruvate 13.3 min, Citramalate 13.75 min, Citrate 10.9 min, Lactate 17.5 min and Acetate 20.3 min.

Glucose Quantification: Similarly two methods were used to quantify glucose. The first was identical to the second organic acid method, utilizing the Resex column for ion exchange linked to refractive discussed above, wherein glucose eluted at 12.5 minutes. The second method was a similar UPLC method also relying on ion exchange and refractive index detection. Chromatographic separation was performed using a Bio-Rad Fast Acid Analysis HPLC Column (100×7.8 mm, 9 μm particle size; CAT #: #1250100, Bio-Rad Laboratories, Inc., Hercules, CA) at 65° C. 5 mM sulfuric acid was used as the eluent. The isocratic elution was as follows: 0-0.1 min, flow rate increased from 0.4 mL/min to 0.42 mL/min, 0.1-12 min flow rate at 0.48 mL/min. Sample injection volume was 10 μL.

Determination of Strain Dry Weight: Culture samples (5 ml, n=3) were taken and washed 2× with deionized water via centrifugation and resuspension. After wash steps the OD of the samples were determined at 600 nm. Subsequently, samples were filtered over pre-weighed nitrocellulose filters (pore size, 0.45 μm). Filters were washed extensively with demineralized water and dried in a microwave oven for 2 min and weighed to determine correlation of OD600 nm and gDCW, which was 0.35.

Phosphate Quantification: Phosphate concentrations were determined using the BioMOL Green colorimetric assay from Enzo Life Sciences (Farmingdale, NY) according to manufacturer's instructions.

Fluorescence measurements: Optical densities and fluorescent were measured using a Tecan Infinite 200 plate reader. Measurements were performed using 200 uL in black 96 well plates (Greiner Bio-One, Reference Number: 655087). Optical density was read at 600 nm (Filter from Omega Optical, Part Number: 3019445) and adjusted by subtracting a blank, followed by correction for pathlength and dilutions. For GFP fluorescence, samples were excited at 412 nm (Omega Optical, Part Number: 3024970) and emission was read at 530 nm (Omega Optical, Part Number: 3032166) using a gain of 60. Fluorescence readings were then adjusted for dilution.

SDS-PAGE and GFP quantification: The OD600 nm of culture samples to be analyzed was measured before harvesting the cells by centrifugation, which was done at 4000 rpm for 15 minutes. The cells were resuspended in 50 μl of phosphate-buffered saline with protease inhibitors (ThermoFisher Scientific, MA, product number A32965) and 5 mM EDTA. 25 μl of the resuspended cells were mixed with 25 μl of 2× Laemmli sample buffer (Biorad, CA) and boiled for 5 minutes at 95° C. The boiled samples were centrifuged at 14,000 rpm for 10 minutes and 20 μg of total protein per sample was then loaded into a 4-15% gradient Mini-Protean TGX precast protein gel (Biorad, CA) and ran at 140 V. The volume loaded per sample was calculated as volume=100/OD600 nm. The gels were stained using Coomassie Brilliant Blue R-250. Gels were imaged using a UVP PhotoDoc-It™ Imaging System (Analytik Jena, CA) and expression levels were quantified using ImageJ (NIH, MD). To correlate GFPuv fluorescence with grams of GFPuv, samples were taken wherein both (i) fluorescence was measured as described above and (ii) expression level was calculated as described above. Total cellular protein was estimated at 500 mg/gDCW or 50% of dry cell weight. In these comparison, 3.24 e 9 relative fluorescent units corresponded to 1 gram of GFPuv. This correlation was also used to calculate GFPuv titers across all experiments.

Cytometry: BL21(DE3) pLys bearing pETM6 (negative control) or pETM6-mCherry as well as DLF_R002 bearing pSMART-HC-Kan (negative control) or pHCKan-yibDp-mCherry were grown in 5 ml of LB overnight at 37° C., 150 rpm. After 16 hours, 1% volume of overnight BL21(DE3) pLys or DLF_R002 cultures were used to inoculate 20 ml of LB or AB media in 250 baffled Erlenmeyer and incubated at 37° C., 150 rpm. BL21(DE3) cultures were induced at OD600 nm ~0.3 with 1 M IPTG solution to a final 1 mM IPTG concentration. Samples for BL21(DE3) were collected 20 hours after induction with IPTG. Samples for DLF_R002 were collected after 24 hours of inoculation. Samples were serially diluted 1000-fold with sterile DI water before analyzing them in a Thermo Attune NXT flow cytometer (ThermoFisher Scientific, MA). Samples were run at a 12.5 pl/min flow rate. Fluorescence measurements were taken from the 620/15 band pass filter after exciting the cells with a yellow laser at 561 nm. Forward scatter vs time plot was monitored during the run to ensure no clogging occurred. The forward scatter height vs forward scatter area plot was also monitored to ensure no cell clumping. Forward scatter height vs side scatter height plots were analyzed using DLF_R002 bearing pSMART-HC-Kan to determine the appropriate gating to exclude small particles from being counted as events. A forward scatter height of 10,000 and a side scatter of 2,500 were used for gating for all samples. Data was analyzed using FlowJo v10.6.1 (BD, NJ).

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. A method of expression of a protein comprising: providing an *E. coli* genetically modified microorganism that is obtained by transforming a microorganism strain with a plasmid, the plasmid comprising a phoB regulated promoter operatively linked to a nucleic acid encoding the expressed protein; and growing the genetically modified microorganism in a batch media to obtain a biomass and express the protein, wherein the batch media enables growth of the genetically modified microorganism in the presence of phosphate in the batch media and autoinduction of protein expression upon depletion of phosphate from the batch media, wherein the batch media contains greater than 5.0 g/L and less than 15.0 g/L of a combination of yeast extract and casamino acids, and the batch media contains from about 15 mM to about 400 mM (NH$_4$)$_2$SO$_4$, ammonium sulfate, wherein the microorganism does not produce the byproduct acetic acid during growth, and wherein the expressed protein is between about 10 and about 55% of the total cellular protein content of the genetically modified microorganism.

2. The method of claim 1, wherein the batch media further comprises iron, calcium, magnesium, ammonium, sulfate and phosphate and trace elements.

3. The method of claim 1, wherein the batch media further comprises thiamine and citric acid.

4. The method of claim 1, wherein the yeast extract and casamino acids is the batch media phosphate source.

5. The method of claim 1, wherein inorganic phosphate is added to the batch media.

6. The method of claim 1, wherein phosphate depletion of the batch media during microorganism growth induces a stationary phase in genetically modified microorganism.

7. The method of claim 1, wherein the amount of expressed protein is greater than 2 g/L.

8. The method of claim 1, wherein the phoB regulated promoter is the yibDp promoter of the *E. coli* yibD (waaH) gene.

9. The method of claim 1, wherein the phoB regulated promoter comprises SEQ ID NO: 1.

10. The method of claim 1, wherein the strain of *E. coli* this is transformed with a plasmid further comprises chromosomal deletion of genes selected from the group consisting of: ackA-pta, pflB, adhE, ldhA, and poxB.

11. The method of claim 1, wherein the strain of *E. coli* this is transformed with a plasmid further comprises a chromosomal deletion of iclR or arcA.

12. The method of claim 1, wherein the genetically modified microorganism reaches a biomass level of about 10 g cell dry weight per liter (CDW/L).

13. The method of claim 1, wherein the ammonium ion is present in an amount from 17 mM to 204 mM.

14. The method of claim 1, wherein the batch media comprises 40.8 mM ammonium sulfate; 6.2 g/L yeast extract, and 3.5 g/L casamino acid.

15. The method of claim 1, wherein the batch media comprises 68 mM ammonium sulfate; 2.5 g/L yeast extract, and 2.5 g/L casamino acid.

* * * * *

SEQUENCE LISTING

<160> NUMBER OF SEQ ID NOS: 34

<210> SEQ ID NO 1
<211> LENGTH: 160
<212> TYPE: DNA

```
<213> ORGANISM: Artificial Sequence
<220> FEATURE:
<223> OTHER INFORMATION: Synthetic

<400> SEQUENCE: 1
gtgcgtaatt gtgctgatct cttatatagc tgctctcatt atctctctac cctgaagtga      60
ctctctcacc tgtaaaaata atatctcaca ggcttaatag tttcttaata caaagcctgt     120
aaaacgtcag gataacttct gtgtaggagg ataatctatg                            160

<210> SEQ ID NO 2
<211> LENGTH: 3527
<212> TYPE: DNA
<213> ORGANISM: Artificial Sequence
<220> FEATURE:
<223> OTHER INFORMATION: Synthetic

<400> SEQUENCE: 2
tcctaatttt tgttgacact ctatcattga tagagttatt ttaccactcc ctatcagtga      60
tagagaaaag tgaaatgaat agttcgacaa agatcgcatt ggtaattacg ttactcgatg     120
ccatggggat tggccttatc atgccagtct tgccaacgtt attacgtgaa tttattgctt     180
cggaagatat cgctaaccac tttggcgtat tgcttgcact ttatgcgtta atgcaggtta     240
tctttgctcc ttggcttgga aaaatgtctg accgatttgg tcggcgccca gtgctgttgt     300
tgtcattaat aggcgcatcg ctggattact tattgctggc ttttttcaagt gcgctttgga    360 tgctgtattt aggccgtttg ctttcaggga tcacaggagc tactggggct gtcgcggcat     420
cggtcattgc cgataccacc tcagcttctc aacgcgtgaa gtggttcggt tggttagggg     480
caagttttgg gcttggttta atagcgggc ctattattgg tggttttgca ggagagattt      540
caccgcatag tccctttttt atcgctgcgt tgctaaatat tgtcactttc cttgtggtta     600
tgttttggtt ccgtgaaacc aaaaatacac gtgataatac agataccgaa gtaggggttg     660
agacgcaatc gaattcggta tacatcactt tatttaaaac gatgcccatt ttgttgatta     720 tttattttc agcgcaattg ataggccaaa ttcccgcaac ggtgtgggtg ctatttaccg      780
aaaatcgttt tggatggaat agcatgatgg ttggctttc attagcgggt cttggtcttt       840
tacactcagt attccaagcc tttgtggcag gaagaatagc cactaaatgg ggcgaaaaaa     900
cggcagtact gctcggattt attgcagata gtagtgcatt tgccttttta gcgtttatat     960
ctgaaggttg gttagttttc cctgttttaa ttttattggc tggtggtggg atcgctttac    1020
ctgcattaca gggagtgatg tctatccaaa caaagagtca tcagcaaggt gctttacagg    1080
gattattggt gagccttacc aatgcaaccg gtgttattgg cccattactg tttgctgtta    1140
tttataatca ttcactacca atttgggatg gctggatttg gattattggt ttagcgtttt    1200
actgtattat tatcctgcta tcgatgacct tcatgttaac ccctcaagct caggggagta    1260
aacaggagac aagtgcttag ttatttcgtc accaaatgat gttattccgc gaaatataat    1320
gaccctcttg ataacccaag agcatcacat atacctgccg ttcactatta tttagtgaaa    1380
tgagatatta tgatattttc tgaattgtga ttaaaaaggc aactttatgc ccatgcaaca    1440
gaaactataa aaaatacaga gaatgaaaag aaacagatag attttttagt tctttaggcc    1500
cgtagtctgc aaatccttttt atgattttct atcaaacaaa agaggaaaat agaccagttg    1560
caatccaaac gagagtctaa tagaatgagg tcgaaaagta aatcgcgcgg gtttgttact    1620
gataaagcag gcaagaccta aaatgtgtaa agggcaaagt gtatactttg gcgtcacccc    1680
ttacatattt taggtctttt tttattgtgc gtaactaact tgccatcttc aaacaggagg    1740
```

-continued

```
gctggaagaa gcagaccgct aacacagtac ataaaaaagg agacatgaac gatgaacatc      1800
aaaaagtttg caaaacaagc aacagtatta acctttacta ccgcactgct ggcaggaggc      1860
gcaactcaag cgtttgcgaa agaaacgaac caaaagccat ataaggaaac atacggcatt      1920
tcccatatta cacgccatga tatgctgcaa atccctgaac agcaaaaaaa tgaaaaatat      1980
caagttcctg agttcgattc gtccacaatt aaaaatatct cttctgcaaa aggcctggac      2040
gtttgggaca gctggccatt acaaaacgct gacggcactg tcgcaaacta tcacggctac      2100
cacatcgtct ttgcattagc cggagatcct aaaaatgcgg atgacacatc gatttacatg      2160
ttctatcaaa aagtcggcga aacttctatt gacagctgga aaaacgctgg ccgcgtcttt      2220
aaagacagcg acaaattcga tgcaaatgat tctatcctaa aagaccaaac acaagaatgg      2280
tcaggttcag ccacatttac atctgacgga aaaatccgtt tattctacac tgatttctcc      2340
ggtaaacatt acggcaaaca aacactgaca actgcacaag ttaacgtatc agcatcagac      2400
agctctttga acatcaacgg tgtagaggat tataaatcaa tctttgacgg tgacggaaaa      2460
acgtatcaaa atgtacagca gttcatcgat gaaggcaact acagctcagg cgacaaccat      2520
acgctgagag atcctcacta cgtagaagat aaaggccaca aatacttagt atttgaagca      2580
aacactggaa ctgaagatgg ctaccaaggc gaagaatctt tatttaacaa agcatactat      2640
ggcaaaagca catcattctt ccgtcaagaa agtcaaaaac ttctgcaaag cgataaaaaa      2700
cgcacggctg agttagcaaa cggcgctctc ggtatgattg agctaaacga tgattacaca      2760
ctgaaaaaag tgatgaaacc gctgattgca tctaacacag taacagatga aattgaacgc      2820
gcgaacgtct ttaaaatgaa cggcaaatgg tacctgttca ctgactcccg cggatcaaaa      2880
atgacgattg acggcattac gtctaacgat atttacatgc ttggttatgt ttctaattct      2940
ttaactggcc catacaagcc gctgaacaaa actggccttg tgttaaaaat ggatcttgat      3000
cctaacgatg taacctttac ttactcacac ttcgctgtac ctcaagcgaa aggaaacaat      3060
gtcgtgatta caagctatat gacaaacaga ggattctacg cagacaaaca atcaacgttt      3120
gcgccaagct tcctgctgaa catcaaaggc aagaaaacat ctgttgtcaa agacagcatc      3180
cttgaacaag acaattaac agttaacaaa taaaaacgca aaagaaatg ccgatattga      3240 ctaccggaag cagtgtgacc gtgtgcttct caaatgcctg attcaggctg tctatgtgtg      3300
actgttgagc tgtaacaagt tgtctcaggt gttcaatttc atgttctagt tgctttgttt      3360
tactggtttc acctgttcta ttaggtgtta catgctgttc atctgttaca ttgtcgatct      3420
gttcatggtg aacagcttta aatgcaccaa aaactcgtaa aagctctgat gtatctatct      3480
tttttacacc gttttcatct gtgcatatgg acagttttcc ctttgat      3527
```

<210> SEQ ID NO 3
<211> LENGTH: 70
<212> TYPE: DNA
<213> ORGANISM: Artificial Sequence
<220> FEATURE:
<223> OTHER INFORMATION: Synthetic

<400> SEQUENCE: 3

```
aaatgatttc cacgatacag aaaaaagaga ctgtcatggg cagaatattg cctctgcccg      60
ccagaaaaag      70
```

<210> SEQ ID NO 4
<211> LENGTH: 70
<212> TYPE: DNA

-continued

```
<213> ORGANISM: Artificial Sequence
<220> FEATURE:
<223> OTHER INFORMATION: Synthetic

<400> SEQUENCE: 4
ctgtttcgat ttagttggca atttaggtag caaactcggc tttaccaccg tcaaaaaaaa      60
cggcgctttt                                                             70

<210> SEQ ID NO 5
<211> LENGTH: 76
<212> TYPE: DNA
<213> ORGANISM: Artificial Sequence
<220> FEATURE:
<223> OTHER INFORMATION: Synthetic

<400> SEQUENCE: 5
taacaataaa aatgaaaatg atttccacga tacagaaaaa agagactgtc atcctaattt      60
ttgttgacac tctatc                                                      76

<210> SEQ ID NO 6
<211> LENGTH: 75
<212> TYPE: DNA
<213> ORGANISM: Artificial Sequence
<220> FEATURE:
<223> OTHER INFORMATION: Synthetic

<400> SEQUENCE: 6
tgccactcag gtatgatggg cagaatattg cctctgcccg ccagaaaaag atcaaaggga      60
aaactgtcca tatgc                                                       75

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
ccgacaggga ttccatctg                                                   19

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
tatgacgacc attttgtcta cagttc                                           26

<210> SEQ ID NO 9
<211> LENGTH: 75
<212> TYPE: DNA
<213> ORGANISM: Artificial Sequence
<220> FEATURE:
<223> OTHER INFORMATION: Synthetic

<400> SEQUENCE: 9
ggacttttgt acttcctgtt tcgatttagt tggcaattta ggtagcaaac tcctaatttt      60
tgttgacact ctatc                                                       75

<210> SEQ ID NO 10
<211> LENGTH: 75
```

```
<212> TYPE: DNA
<213> ORGANISM: Artificial Sequence
<220> FEATURE:
<223> OTHER INFORMATION: Synthetic

<400> SEQUENCE: 10
ataaaaacgg cgctaaaaag cgccgttttt tttgacggtg gtaaagccga atcaaaggga      60
aaactgtcca tatgc                                                       75

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
cctgactgta ctaacggttg ag                                               22

<210> SEQ ID NO 12
<211> LENGTH: 27
<212> TYPE: DNA
<213> ORGANISM: Artificial Sequence
<220> FEATURE:
<223> OTHER INFORMATION: Synthetic

<400> SEQUENCE: 12
tgacttttat ggcgttcttt gtttttg                                          27

<210> SEQ ID NO 13
<211> LENGTH: 71
<212> TYPE: DNA
<213> ORGANISM: Artificial Sequence
<220> FEATURE:
<223> OTHER INFORMATION: Synthetic

<400> SEQUENCE: 13
agatataaaa aatacatatt caatcattaa aacgattgaa tggagaactt ttggctgacg      60
ccgttggata c                                                           71

<210> SEQ ID NO 14
<211> LENGTH: 70
<212> TYPE: DNA
<213> ORGANISM: Artificial Sequence
<220> FEATURE:
<223> OTHER INFORMATION: Synthetic

<400> SEQUENCE: 14
tttaagggtt aattgttaca ttgaaatggc tagttattcc ccgggggcgat tcagccaatc     60 gactggcgag                                                             70

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
cctcatgcta ttttcgctta tatgc                                            25

<210> SEQ ID NO 16
<211> LENGTH: 25
<212> TYPE: DNA
```

-continued

```
<213> ORGANISM: Artificial Sequence
<220> FEATURE:
<223> OTHER INFORMATION: Synthetic

<400> SEQUENCE: 16
gattattatg gtgtcacgcc atctc                                              25

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gtcatcgtgg ccggatcttg                                                    20

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
attaatgcag ctggcacgac ag                                                 22

<210> SEQ ID NO 19
<211> LENGTH: 174
<212> TYPE: DNA
<213> ORGANISM: Artificial Sequence
<220> FEATURE:
<223> OTHER INFORMATION: Synthetic

<400> SEQUENCE: 19
ctgtcgtgcc agctgcatta atcagtccag ttacgctgga gtccagtcca gttacgctgg         60
agtctgaggc tcgtcctgaa tgatatcaag cttgaattcg ttgacgaatt ctctagatat        120
cgctcaatac tgaccattta aatcatacct gaccgtcatc gtggccggat cttg             174

<210> SEQ ID NO 20
<211> LENGTH: 1067
<212> TYPE: DNA
<213> ORGANISM: Artificial Sequence
<220> FEATURE:
<223> OTHER INFORMATION: Synthetic

<400> SEQUENCE: 20
tgaggctcgt cctgaatgat atcaagcttg aattcgttgt gcgtaattgt gctgatctct         60
tatatagctg ctctcattat ctctctaccc tgaagtgact ctctcacctg taaaaataat        120
atctcacagg cttaatagtt tcttaataca aagcctgtaa aacgtcagga taacttcttg        180
taggaggata atctatggct agcaaaggag aagaactttt cactggagtt gtcccaattc        240
ttgttgaatt agatggtgat gttaatgggc acaaattttc tgtcagtgga gagggtgaag        300
gtgatgctac atacggaaag cttacccctta aatttatttg cactactgga aaactacctg       360
ttccatggcc aacacttgtc actactttct cttatggtgt tcaatgcttt tcccgttatc        420
cggatcatat gaaacggcat gactttttca agagtgccat gcccgaaggt tatgtacagg        480
aacgcactat atctttcaaa gatgacggga actacaagac gcgtgctgaa gtcaagtttg        540
aaggtgatac ccttgttaat cgtatcgagt taaaaggtat tgattttaaa gaagatggaa        600
acattctcgg acacaaactc gagtacaact ataactcaca caatgtatac atcacggcag        660
```

-continued

```
acaaacaaaa gaatggaatc aaagctaact tcaaaattcg ccacaacatt gaagatggat      720
ccgttcaact agcagaccat tatcaacaaa atactccaat tggcgatggc cctgtccttt      780
taccagacaa ccattacctg tcgacacaat ctgccctttc gaaagatccc aacgaaaagc      840
gtgaccacat ggtccttctt gagtttgtaa ctgctgctgg gattacacat ggcatggatg      900
agctctacaa ataatgagga tccccggctt atcggtcagt ttcacctgat ttacgtaaaa      960
acccgcttcg gcgggttttt gcttttggag gggcagaaag atgaatgact gtccacgacg     1020
ctatacccaa aagaaagacg aattctctag atatcgctca atactga                   1067
```

<210> SEQ ID NO 21
<211> LENGTH: 1171
<212> TYPE: DNA
<213> ORGANISM: Artificial Sequence
<220> FEATURE:
<223> OTHER INFORMATION: Synthetic

<400> SEQUENCE: 21

```
gtctgaggct cgtcctgaat gatatcaagc ttgaattcgt tcgtgcgtaa ttgtgctgat       60
ctcttatata gctgctctca ttatctctct accctgaagt gactctctca cctgtaaaaa      120
taatatctca caggcttaat agtttcttaa tacaaagcct gtaaaacgtc aggataactt      180
ctgtgtagga ggataatcta tggtatcaaa aggagaggaa gataacatgg ctattatcaa      240
agaatttatg cgcttcaaag ttcacatgga aggtagcgtg aacggtcacg agttcgagat      300
tgaaggtgaa ggtgaagggc gtccgtacga aggtacacag accgctaaac tgaaggtgac      360
gaaaggtggc cctcttccat ttgcgtggga tattcttagt ccgcaattta tgtatggatc      420
taaggcgtat gtcaagcacc cggctgacat cccagattac ttaaaactta gcttcccaga      480
gggattcaaa tgggagcgcg ttatgaattt cgaggacggc ggtgtagtga ccgtcactca      540
ggattcatca cttcaagatg gcgaatttat ctacaaggtc aagctgcgtg gacaaatttt      600
tccgtcggat gggcctgtca tgcagaagaa gacaatgggc tgggaagcgt cgtcagagcg      660
tatgtatcca gaggacggag cgttaaaagg ggaaattaag cagcgcctga gttgaagga      720 tggcgggcat tatgacgcag aggttaaaac cacttataaa gcgaaaaagc cagtccaatt      780
gccaggagcc tacaatgtca atatcaaatt agatatcaca agtcataacg aggattacac      840
gatcgtcgaa caatatgagc gcgcagaagg tcgccatagt acaggaggaa tggacgaact      900
gtacaaataa tgactcgagt ctggtaaaac tagcattcga cctagcataa ccccgcgggg      960
cctcttcggg ggtctcgcgg ggtttttttgc tgaaagaagc ttcaaataaa acgaaaggct     1020
cagtcgaaag actgggcctt tcgttttatc tgttgtttgt cgctgcggcc gggtcaggta     1080
tgatttaaat ggtcagtaac gggtcttgag gggttttttg caatgggttc atcccgtggg     1140
gacgaattct ctagatatcg ctcaatactg a                                    1171
```

<210> SEQ ID NO 22
<211> LENGTH: 1971
<212> TYPE: DNA
<213> ORGANISM: Artificial Sequence
<220> FEATURE:
<223> OTHER INFORMATION: Synthetic

<400> SEQUENCE: 22

```
tgcccaggca tcaaataaaa cgaaaggctc agtcgaaaga ctgggccttt cgttttatct       60
gttgtttgtc ggtgaacgct ctctactaga gtcacactgg ctcaccttcg ggtgggcctt      120
```

-continued

```
tctgcgttta tacacagcta acaccacgtc gtccctatct gctgccctag gtctatgagt      180
ggttgctgga taacgtgcgt aattgtgctg atctcttata tagctgctct cattatctct      240
ctaccctgaa gtgactctct cacctgtaaa aataatatct cacaggctta atagtttctt      300
aatacaaagc ctgtaaaacg tcaggataac ttctatattc agggagacca caacggtttc      360
cctctacaaa taattttgtt taactttgga aaaaggagat ataccatgca tcatcatcat      420
catcactcca accatttatt cgatgcgatg cgtgccgcgg cgcctgggaa tgcgccgttc      480
atccgcatcg acaatacacg cacctggacc tacgacgatg cctttgcctt gagtggtcgc      540
attgcgtcag ctatggacgc actcggcatt cgcccgggag accgcgtggc cgtgcaggtg      600
gagaaatctg ccgaagcact gattctgtat cttgcgtgtc tgcgtagcgg tgccgtatat      660
ttgccactga acactgctta tacacttgcg gaactggact actttattgg tgatgccgaa      720
ccgcgcctcg ttgttgtagc gtcatccgcc cgtgcaggtg tggaaaccat tgcgaaaccg      780 cgcgggggcca ttgtagaaac tctggatgca gctggcagcg gaagcttgct ggacttggcg      840
cgcgatgagc ctgctgattt cgtggacgct agtcgctcgg cggacgatct ggcggcaatt      900
ctttatacaa gtgggacgac agggcgttct aaggggggcaa tgctgacaca cggcaacctg      960
ctttctaacg cgcttacatt gcgtgatttc tggcgtgtaa ccgcaggcga tcgtctgatt     1020
catgcgttac cgattttttca tacacatggc ctgtttgtcg ctactaatgt cacattactg     1080 gccgggggcct ctatgtttct gttaagcaaa tttgatccgg aagagatcct gtctttgatg     1140
ccgcaggcta ccatgctgat gggcgtaccg accttctatg ttcgcttgct gcaatcaccg     1200
cgcctggata aacaggcagt agcgaatatt cgcctgttta ttagtgggtc cgcaccactg     1260
ctggcagaga cacacactga atttcaagcg cgtaccggcc atgccattct ggaacgctac     1320
ggaatgaccg agaccaacat gaacacctca aatccgtatg agggtaaacg tattgcgggt     1380
actgtgggct ttcctctccc ggatgtcact gttcgtgtta ccgacccggc aaccggtctc     1440
gccttacctc cggaacagac gggaatgatc gaaattaaag gtccgaacgt gtttaagggc     1500
tattggcgca tgcccgagaa gaccgctgcc gaattcaccg ccgatggttt ctttatcagt     1560
ggtgatttag gtaaaatcga tcgcgatgga tacgttcata ttgtgggggcg cgggaaagat     1620 ctggttattt caggaggcta taatatttat ccgaaagaag ttgaggggga aattgaccag     1680
attgaagggg tggttgaatc agcagtgatc ggcgttccgc acccggattt tggtgaaggt     1740
gtcacagcgg ttgtggttcg caaaccaggg gcggctctgg atgaaaaagc gatcgtctct     1800
gctctgcagg accgtctggc tcgttataaa caaccgaaac gcatcatttt tgctgaagat     1860
ctgccgcgta acacaatggg taaagtccag aaaaacatct gcgccagca gtatgcagac     1920 ttatatactc gtacgtagta agacgaattc tctagatatc gctcaatact g            1971
```

<210> SEQ ID NO 23
<211> LENGTH: 1822
<212> TYPE: DNA
<213> ORGANISM: Artificial Sequence
<220> FEATURE:
<223> OTHER INFORMATION: Synthetic

<400> SEQUENCE: 23

```
cctgacgttt tacaggcttt gtattaagaa actattaagc ctgtgagata ttatttttac       60
aggtgagaga gtcacttcag ggtagagaga taatgagagc agctatataa gagatcagca      120
caattacgca cttatttgcc gactaccttg gtgatctcgc ctttcacgta gtggacaaat      180
tcttccaact gatctgcgcg cgaggccaag cgatcttctt cttgtccaag ataagcctgt      240
```

-continued

```
ctagcttcaa gtatgacggg ctgatactgg gccggcaggc gctccattgc ccagtcggca       300
gcgacatcct tcggcgcgat tttgccggtt actgcgctgt accaaatgcg ggacaacgta       360
agcactacat ttcgctcatc gccagcccag tcgggcggcg agttccatag cgttaaggtt       420
tcatttagcg cctcaaatag atcctgttca ggaaccggta caaagagttc ctccgccgct       480
ggacctacca aggcaacgct atgttctctt gcttttgtca gcaagatagc cagatcaatg       540
tcgatcgtgg ctggctcgaa gatacctgca agaatgtcat tgcgctgcca ttctccaaat       600
tgcagttcgc gcttagctgg ataacgccac ggaatgatgt cgtcgtgcac aacaatggtg       660
acttctacag cgcggagaat ctcgctctct ccaggggaag ccgaagtttc caaaaggtcg       720
ttgatcaaag ctcgccgcgt tgtttcatca agccttacgg tcaccgtaac cagcaaatca       780
atatcactgt gtggcttcag gccgccatcc actgcggagc cgtacaaatg tacggccagc       840
aacgtcggtt cgagatggcg ctcgatgacg ccaactacct ctgatagttg agtcgatact       900
tcggcgatca ccgcttccct catactcttc cttttttcaat attattgaag catttatcag       960
ggttattgtc tcatgagcgg atacatattt gaatgtattt agaaaaataa acaaatagct      1020
agctcactcg gtcgctacgc tccgggcgtg agactgcggc gggcgctgcg gacacataca      1080
aagttaccca cagattccgt ggataagcag gggactaaca tgtgaggcaa aacagcaggg      1140
ccgcgccggt ggcgtttttc cataggctcc gccctcctgc cagagttcac ataaacagac      1200 gctttttccgg tgcatctgtg ggagccgtga ggctcaacca tgaatctgac agtacgggcg      1260
aaacccgaca ggacttaaag atccccaccg tttccggcgg gtcgctccct cttgcgctct      1320
cctgttccga ccctgccgtt taccggatac ctgttccgcc tttctccctt acgggaagtg      1380
tggcgctttc tcatagctca cacactggta tctcggctcg gtgtaggtcg ttcgctccaa      1440
gctgggctgt aagcaagaac tccccgttca gcccgactgc tgcgccttat ccggtaactg      1500
ttcacttgag tccaacccgg aaaagcacgg taaaacgcca ctggcagcag ccattggtaa      1560
ctgggagttc gcagaggatt tgtttagcta aacacgcggt tgctcttgaa gtgtgcgcca      1620
aagtccggct acactggaag gacagatttg gttgctgtgc tctgcgaaag ccagttacca      1680
cggttaagca gttccccaac tgacttaacc ttcgatcaaa ccacctcccc aggtggtttt      1740
ttcgtttaca gggcaaaaga ttacgcgcag aaaaaaagga tctcaagaag atcctttgat      1800
cttttctact gaaccgctct gc                                              1822
```

```
<210> SEQ ID NO 24
<211> LENGTH: 1821
<212> TYPE: DNA
<213> ORGANISM: Artificial Sequence
<220> FEATURE:
<223> OTHER INFORMATION: Synthetic

<400> SEQUENCE: 24
agcctgtaaa acgtcaggat aacttctata ttcagggaga ccacaacggt ttccctctac        60
aaataatttt gtttaacttt cgtgtgtagg aggataatct atgtatacgg tggggggacta       120 cttgcttgat cgcctgcacg agttaggcat cgaggaaatt tttggtgtac ccggggacta       180
taacctgcag ttccttgatc agatcatttc acgtgaggat atgaaatgga ttgggaacgc       240
caatgaactt aacgcatcat atatggcgga tggatatgct cgcacaaaaa aagccgcggc       300
ttttcttaca actttcggcg tgggggagtt aagtgctatc aatggattgg ccggctcgta       360
tgctgaaaat ctgcccgttg tagaaatcgt aggtagccca acctccaagg tccagaacga       420
```

-continued

```
cggtaaattc gtccaccaca ctttagcaga tggcgatttt aagcacttca tgaagatgca    480
tgaaccggtg acagctgccc gcactctttt gaccgccgag aatgcgactt atgaaattga    540
tcgtgtctta agtcaactgc tgaaggaacg taaaccagtt tacattaact tacccgtcga    600
tgtcgcggca gctaaggcag agaaaccagc cttgagtttg gagaaggaaa gttcaaccac    660
aaacaccacc gagcaagtta ttctttcaaa gattgaagag tccttgaaga acgcccaaaa    720
accagtcgtt attgccggtc atgaggttat cagtttcggg cttgagaaaa cagtcacgca    780
attcgtctcc gagaccaaac ttccaatcac aacgctgaat ttcggcaagt ctgcggtcga    840
tgaatcatta ccttcgtttt tggggatcta taatggtaaa ctgagtgaga tctctcttaa    900
aaactttgtc gaatcagccg attttatctt aatgcttggc gtgaaattaa cggactcatc    960
tactggcgct tttacccatc atttggatga aaataaaatg atttctctta atatcgatga   1020
gggtattatt ttcaataagg tggtagagga tttcgatttt cgcgcagttg tctcgtcatt   1080
atcagaactt aaaggtattg agtacgaagg acaatatatc gataaacagt acgaagagtt   1140
tatcccgagc agcgcaccac tttctcaaga tcgcttatgg caagcagtgg agagcctgac   1200
tcagtcaaat gaaactattg tcgctgaaca aggaacgtct ttttttggtg cctctactat   1260
cttccttaaa agcaactcgc gtttcatcgg ccaaccactg tggggtcaa  tcgggtacac   1320 gttccccgct gctcttgggt ctcagattgc cgacaaggag agtcgccatc tgttattcat   1380
tggtgacggg tcccttcaac tgactgttca ggagttaggc ctgtctatcc gcgaaaaatt   1440
gaatccaatc tgtttttatca ttaataatga cggttatacc gtggagcgcg agatccatgg   1500
gccaacacaa agctacaacg acattcccat gtggaattat tcgaagcttc cggaaacttt   1560
tggagcaaca gaggaccgtg ttgtaagcaa gatcgttcgc acggagaatg agttcgtatc   1620
cgttatgaag gaagctcaag cggacgttaa ccgtatgtat tggattgaac tggttttgga   1680
aaaagaggat gcccccaagt tattgaaaaa aatgggaaaa ttgttcgcgg agcagaataa   1740
gcatcatcac caccaccact gatgttgacc gcaaaaaacc ccgcttcggc ggggtttttt   1800
cgcagagcgg ttcagtagaa a                                             1821
```

<210> SEQ ID NO 25
<211> LENGTH: 1161
<212> TYPE: DNA
<213> ORGANISM: Artificial Sequence
<220> FEATURE:
<223> OTHER INFORMATION: Synthetic

<400> SEQUENCE: 25

```
tgaggctcgt cctgaatgat atcaagcttg aattcgtttg cccaggcatc aaataaaacg     60
aaaggctcag tcgaaagact gggcctttcg ttttatctgt tgtttgtcgg tgaacgctct    120
ctactagagt cacactggct caccttcggg tgggcctttc tgcgtttata cacagctaac    180
accacgtcgt ccctatctgc tgccctaggt ctatgagtgg ttgctggata acgtgcgtaa    240
ttgtgctgat ctcttatata gctgctctca ttatctctct accctgaagt gactctctca    300
cctgtaaaaa taatatctca caggcttaat agtttcttaa tacaaagcct gtaaaacgtc    360
aggataactt ctatattcag ggagaccaca acggtttccc tctacaaata attttgttta    420
actttaaaga ggagaaatac tagatgggga acgcagcatc tgcgcgccgc atgtccccga    480
tcctgggtta ctggaaaatc aaagggttag tgcagccaac ccgtctgtta ttagaatacc    540
tggaggaaaa atacgaggaa cacctgtacg agcgcgatga aggcgataaa tggcgcaata    600 aaaaaattcga actcgggctg gaattcccaa acttacccta ttatattgat ggagatgtta    660
```

-continued

```
aattgaccca gtctatggca atcattcgct atattgcaga taaacataac atgttgggcg        720
gctgtcctaa ggagcgcgcg gaaattagta tgctggaagg cgcggtgctg gatatccgct        780
atggtgttag ccgcattgcg tactcgaaag attttgagac gctcaaagtt gattttctga        840
gtaaactgcc tgaaatgtta aagatgtttg aagatcgctt gtgtcacaaa acgtatttaa        900
atggtgatca tgtcacccat ccagacttta tgctgtatga tgcgcttgat gtggttttgt        960
acatggatcc gatgtgcctg gatgcctttc cgaagctggt ctgtttcaaa aaacgcatcg       1020
aggctattcc gcaaatcgac aaatatctca atctagtaa atacatcgcg tggcctctgc       1080
agggctggca agcgaccttt ggtgggggcg atcatccgcc aaaatgataa gacgaattct       1140
ctagatatcg ctcaatactg a                                                 1161
```

<210> SEQ ID NO 26
<211> LENGTH: 1212
<212> TYPE: DNA
<213> ORGANISM: Artificial Sequence
<220> FEATURE:
<223> OTHER INFORMATION: Synthetic

<400> SEQUENCE: 26

```
cattgcataa tacgactcac tatagggaga ccacaacggt ttcccactag aaataatttt         60
gtttaacttt aagaaggaga tatacataaa gaggagaaat actagatgac aaatcctggt        120
gtaagtgcct ggcaagttaa taccgcatat accgctgggc agttagtcac ttataacggc        180
aagacctaca agtgcttgca gcctcacaca tccttggcag gttgggaacc gtccaatgta        240
cccgcccttt ggcaacttca gggctctgcc ggtagtgcgg cgggttccgg tgaatttatg        300
ctggttctgc acaacagcca aaaactgcaa attctgtaca aatctctgga aaaatctatt        360
cctgaaagca ttaaagttta tggtgcgatc ttcaacatca aggataaaaa ccctttcaat        420
atggaggtgc tggtcgacgc gtggcctgat taccaaatcg tcatcacccg tccgcagaag        480
caagaaatga aagatgacca ggaccactat actaacacct accacatctt cactaaagcg        540
ccggacaaac tggaagaagt tctgagctac tccaatgtta tctcctggga acaaacgctg        600
cagattcaag gttgccagga aggtctggat gaggcgattc gtaaggtcgc tacctctaag        660
tccgttcaag tcgattacat gaaaaaccatc ctgtttatcc cggagctgcc gaagaaacac        720
aaaacctcct ctaacgacaa gatggagctg ttcgaagtag acgatgacaa caaagagggt        780 aactttttcca atatgttcct ggacgcctcc cacgccggtc tggttaatga gcactgggcg        840
ttcggtaaaa acgaacgctc cctgaagtac attgagcgtt gtctgcagga ttttctgggt        900
tttggtgtcc tgggtccaga gggtcaactg gtctcttgga tcgttatgga acagtcttgt        960
gaactgcgta tgggttatac tgtgccaaaa taccgtcacc aaggtaatat gctgcaaatc       1020
ggttatcatc tggagaagta cctgagccag aaggaaatcc cgttctattt ccatgttgcc       1080
gataataacg aaaagagcct gcaagccctg aacaatctgg gcttcaagat ctgcccttgc       1140
ggttggcacc agtggaagtg cacgcctaaa aagtactgtg gcggtggcca tcatcaccat       1200
caccattaat ga                                                          1212
```

<210> SEQ ID NO 27
<211> LENGTH: 20
<212> TYPE: DNA
<213> ORGANISM: Artificial Sequence
<220> FEATURE:
<223> OTHER INFORMATION: Synthetic

```
<400> SEQUENCE: 27
actccagcgt aactggactg                                    20

<210> SEQ ID NO 28
<211> LENGTH: 26
<212> TYPE: DNA
<213> ORGANISM: Artificial Sequence
<220> FEATURE:
<223> OTHER INFORMATION: Synthetic

<400> SEQUENCE: 28
actgaccatt taaatcatac ctgacc                             26

<210> SEQ ID NO 29
<211> LENGTH: 16
<212> TYPE: DNA
<213> ORGANISM: Artificial Sequence
<220> FEATURE:
<223> OTHER INFORMATION: Synthetic

<400> SEQUENCE: 29
agcagccatc accatc                                        16

<210> SEQ ID NO 30
<211> LENGTH: 27
<212> TYPE: DNA
<213> ORGANISM: Artificial Sequence
<220> FEATURE:
<223> OTHER INFORMATION: Synthetic

<400> SEQUENCE: 30
gcccatatgt atatctcctt cttaaag                             27

<210> SEQ ID NO 31
<211> LENGTH: 44
<212> TYPE: DNA
<213> ORGANISM: Artificial Sequence
<220> FEATURE:
<223> OTHER INFORMATION: Synthetic

<400> SEQUENCE: 31
ctggaaaaag gagatatacc atgacaaatc ctggtgtaag tgcc          44

<210> SEQ ID NO 32
<211> LENGTH: 46
<212> TYPE: DNA
<213> ORGANISM: Artificial Sequence
<220> FEATURE:
<223> OTHER INFORMATION: Synthetic

<400> SEQUENCE: 32
gtgagtcgta ttagaagagc tcattaatgg tgatggtgat gatggc        46

<210> SEQ ID NO 33
<211> LENGTH: 33
<212> TYPE: DNA
<213> ORGANISM: Artificial Sequence
<220> FEATURE:
<223> OTHER INFORMATION: Synthetic

<400> SEQUENCE: 33
taatgagctc ttctaatacg actcactata ggg                      33

<210> SEQ ID NO 34
<211> LENGTH: 28
```

-continued

```
<212> TYPE: DNA
<213> ORGANISM: Artificial Sequence
<220> FEATURE:
<223> OTHER INFORMATION: Synthetic

<400> SEQUENCE: 34
catggtatat ctcctttttc cagaagtg                                        28
```